(12) United States Patent
Guan et al.

(10) Patent No.: US 11,077,205 B2
(45) Date of Patent: Aug. 3, 2021

(54) SYNTHETIC COMPOUND FOR IMPROVING EFFICIENCY OF TRANSFECTION

(71) Applicant: Klinikum der Universität München, Munich (DE)

(72) Inventors: Shan Guan, Munich (DE); Joseph Rosenecker, Muensing (DE)

(73) Assignee: Klinikum der Universität München, Munich (DE)

( * ) Notice: Subject to any disclaimer, the term of this patent is extended or adjusted under 35 U.S.C. 154(b) by 0 days.

(21) Appl. No.: 16/088,730

(22) PCT Filed: Mar. 30, 2017

(86) PCT No.: PCT/EP2017/057530
§ 371 (c)(1),
(2) Date: Sep. 26, 2018

(87) PCT Pub. No.: WO2017/167870
PCT Pub. Date: Oct. 5, 2017

(65) Prior Publication Data
US 2019/0083654 A1 Mar. 21, 2019

(30) Foreign Application Priority Data
Mar. 31, 2016 (EP) ..................... 16163326

(51) Int. Cl.
| *A61K 38/04* | (2006.01) |
| *A61K 48/00* | (2006.01) |
| *C12N 15/87* | (2006.01) |
| *C07K 7/08* | (2006.01) |
| *C07K 19/00* | (2006.01) |

(52) U.S. Cl.
CPC .......... *A61K 48/0041* (2013.01); *C07K 7/08* (2013.01); *C07K 19/00* (2013.01); *C12N 15/87* (2013.01); *C07K 2319/01* (2013.01); *C07K 2319/09* (2013.01); *C07K 2319/80* (2013.01); *C07K 2319/85* (2013.01)

(58) Field of Classification Search
None
See application file for complete search history.

(56) References Cited

U.S. PATENT DOCUMENTS

| 6,881,577 B2 * | 4/2005 | Cartier ................. C07K 14/001 435/458 |
| 7,060,291 B1 | 6/2006 | Meers et al. |
| 8,058,068 B2 | 11/2011 | Hawley-Nelson et al. |
| 9,399,016 B2 * | 7/2016 | Hart ....................... A61K 47/64 |
| 2009/0098652 A1 | 4/2009 | Stupp et al. |
| 2009/0253206 A1 | 10/2009 | Siebenkotten et al. |
| 2010/0179212 A1 | 7/2010 | Pitard |

FOREIGN PATENT DOCUMENTS

| EP | 1294908 A1 * | 3/2003 | ........... C07K 14/001 |
| EP | 1 294 908 B1 | 3/2006 | |
| WO | 2010/118213 A2 | 10/2010 | |

OTHER PUBLICATIONS

Zhang, J Gene Med. 2013 ; 15(0): 271-281 (Year: 2013).*
Dailey, Journal of Controlled Release 100 (2004) 425-436 (Year: 2004).*
Evans et al., "Characterization and Biological Evaluation of a Microparticle Adjuvant Formulation for Plasmid DNA Vaccines," Journal of Pharmaceutical Sciences, vol. 93, No. 7, pp. 1924-1939 (Jul. 2004).
International Search Report, International Application No. PCT/EP2017/057530 (published under WO 2017/167870), 3 pages (May 29, 2017).
Letchford et al, "A review of the formation and classification of amphiphilic block copolymer nanoparticulate structures: micelles, nanospheres, nanocapsules and polymersomes," European Journal of Pharmaceutics and Biopharmaceutics, vol. 65, No. 3, pp. 259-269 (Feb. 28, 2007).
Monera et al., "Relationship of Sidechain Hydrophobicity and α-Helical Propensity on the Stability of the Single-stranded Amphipathic α-Helix," Journal of Peptide Science, vol. 1, pp. 319-329 (1995).
Richard-Fiardo et al., "Evaluation of tetrafunctional block copolymers as synthetic vectors for lung gene transfer," Biomaterials, vol. 45, pp. 10-17 (Mar. 2015).

(Continued)

*Primary Examiner* — Satyanarayana R Gudibande
(74) *Attorney, Agent, or Firm* — Prismatic Law Group, PLLC

(57) ABSTRACT

The invention concerns a synthetic compound for enabling transfection of eukaryotic cells by means of an amphiphilic block copolymer which synthetic compound comprises a peptide residue having at least one targeting sequence and a nucleic acid binding sequence which nucleic acid binding sequence comprises or consists of at least four consecutive amino acid residues which are positively charged at pH 7.4, wherein the targeting sequence is any sequence that causes a direction of the sequence to a position or a structure inside or on the surface of eukaryotic cells, characterized in that the synthetic compound further comprises a hydrophobic moiety covalently linked to the peptide residue, wherein the hydrophobic moiety comprises or consists of lipoic acid residue, lipoamide residue, a tetradecyl residue, a cholesteryl residue, or a further peptide residue having a sequence with more than 40% amino acid residues with hydrophobic side chains.

16 Claims, 39 Drawing Sheets

Specification includes a Sequence Listing.

(56) References Cited

OTHER PUBLICATIONS

Sereda et al., "Reversed-phase chromatography of synthetic amphipathic α-helical peptides as a model for ligand/receptor interactions effect of changing hydrophobic environment on the relative hydrophilicity/hydrophobicity of amino acid side-chains," Journal of Chromatography A, vol. 676, pp. 139-153 (1994).
Written Opinion, International Application No. PCT/EP2017/057530 (published under WO 2017/167870), 6 pages (May 29, 2017).
Zaslaysky et al., "Relative Hydrophobicity of Synthetic Macromolecules I. Polyethylene Glycol, Polyacrylamide and Polyvinylpyrrolidone," Journal of Chromatography, vol. 285, pp. 63-68 (Jan. 1, 1984).
Zhang et al., "Efficacy and mechanism of poloxamine-assisted polyplex transfection," J. Gene Med., vol. 15, pp. 271-281 J. Gene Med. 2013.

\* cited by examiner

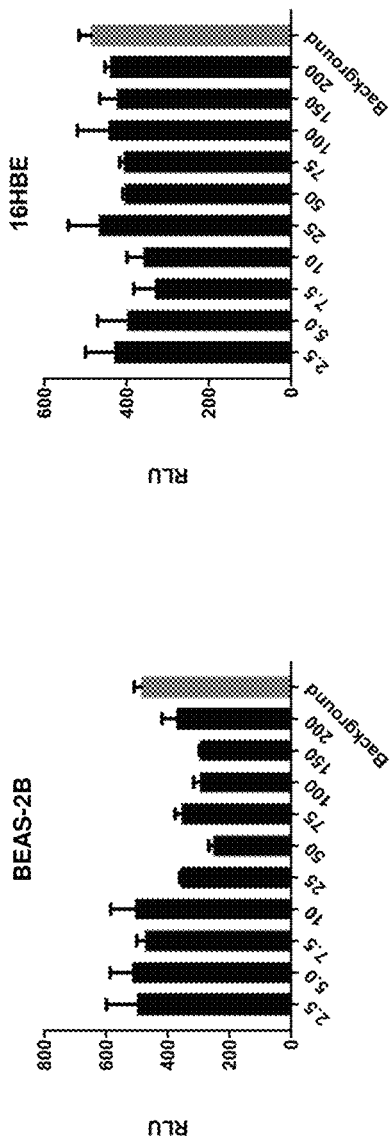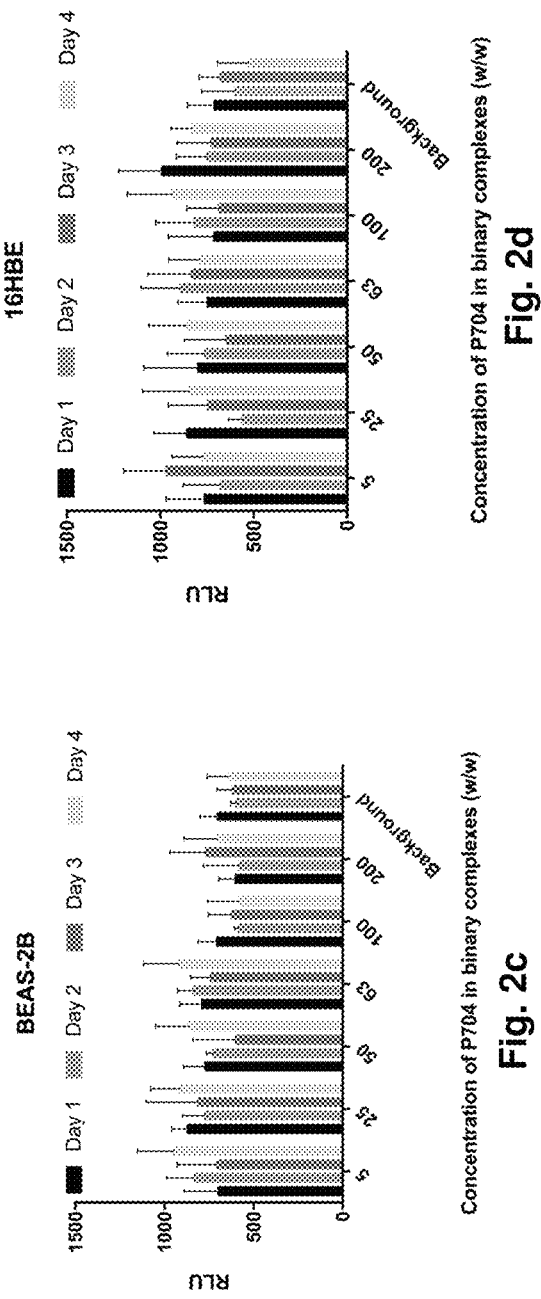

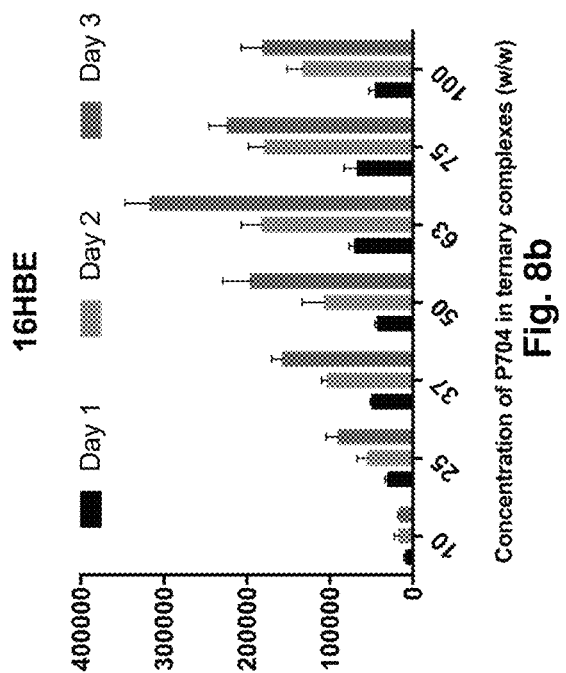
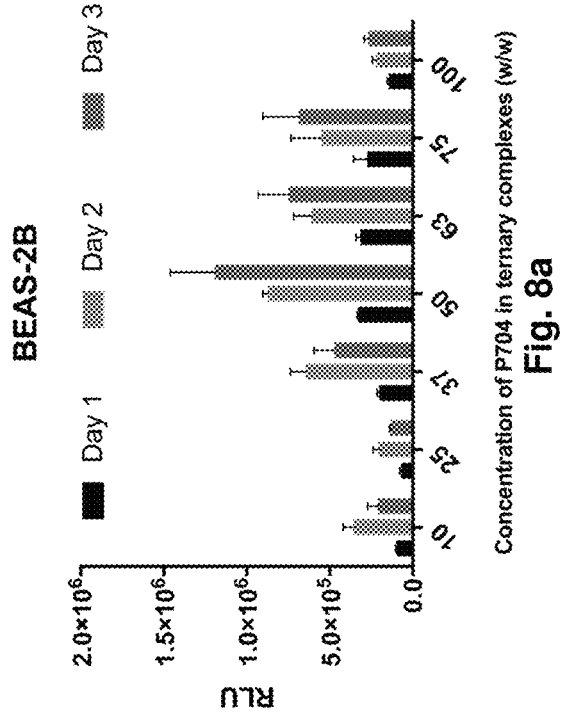
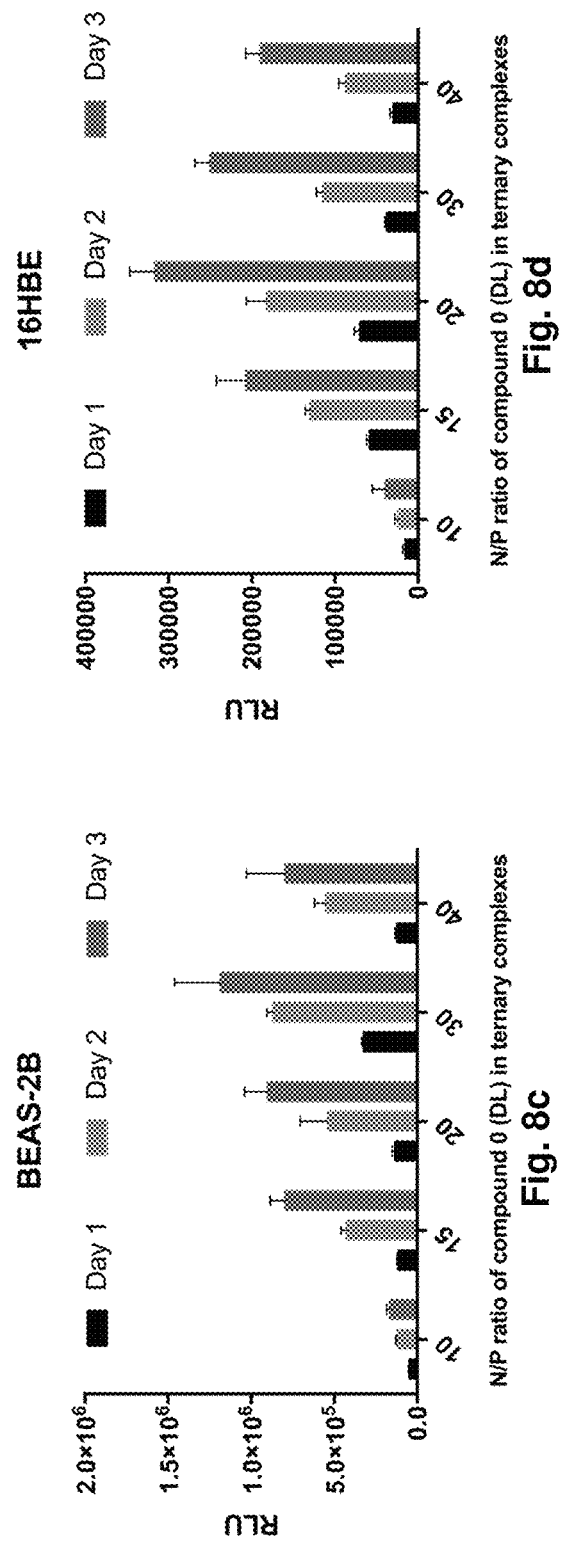

Concentration of mRNA in ternary complexes ( ng/well )

Different media used in complex preparation

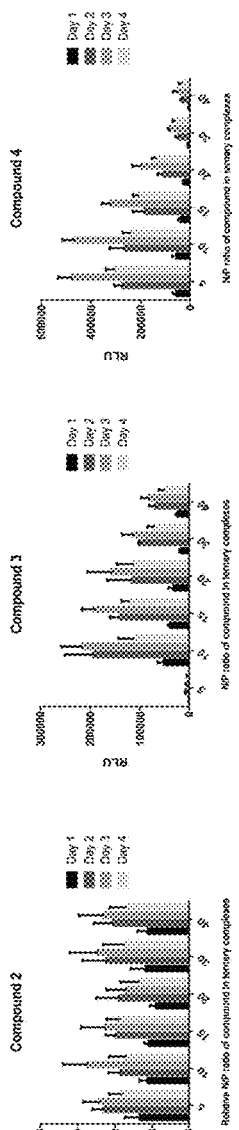
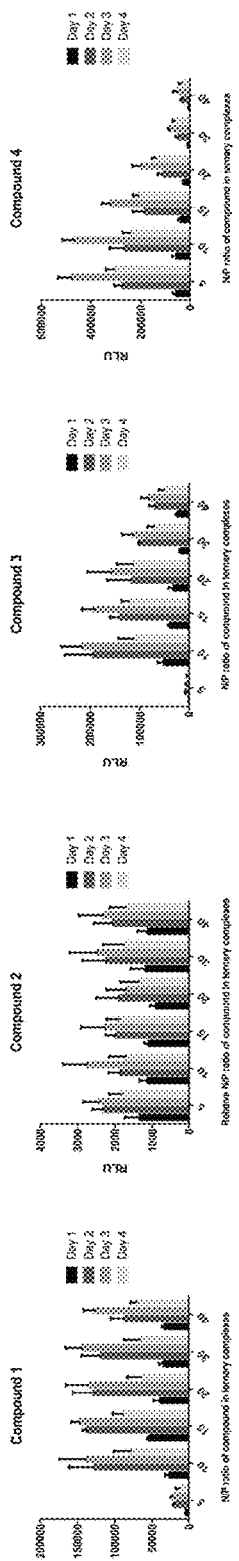
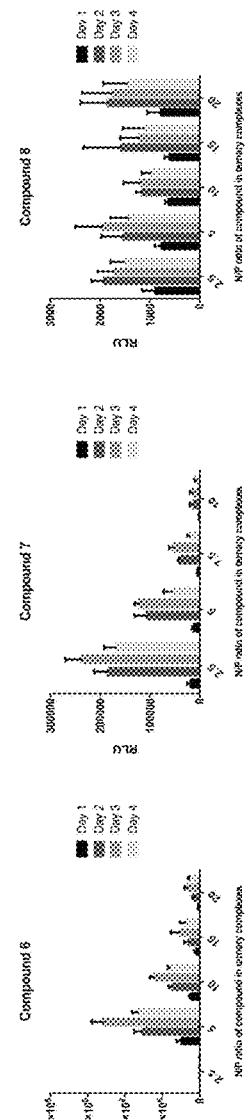
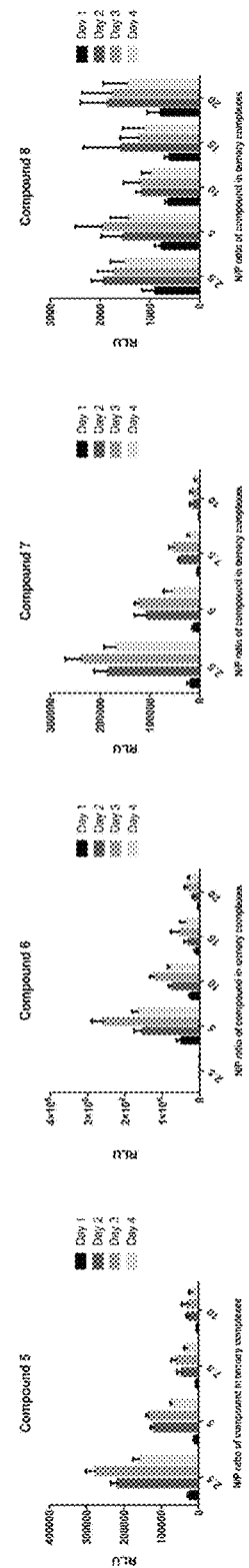
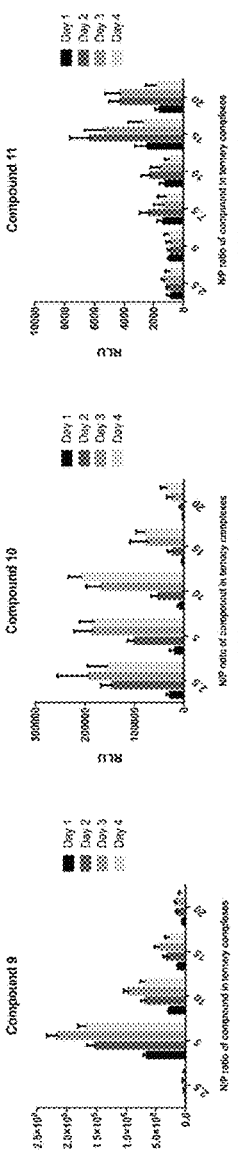
Fig. 13a, Fig. 13b, Fig. 13c, Fig. 13d, Fig. 13e, Fig. 13f, Fig. 13g, Fig. 13h, Fig. 13i, Fig. 13j, Fig. 13k

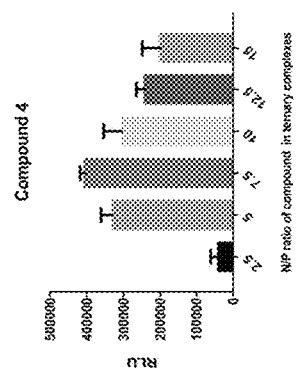
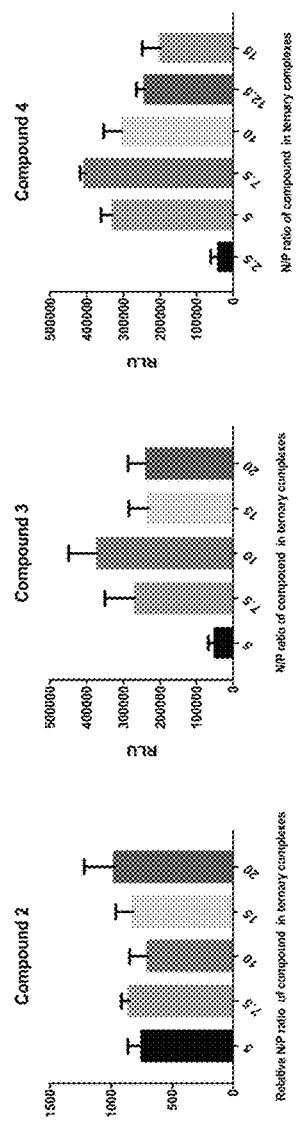
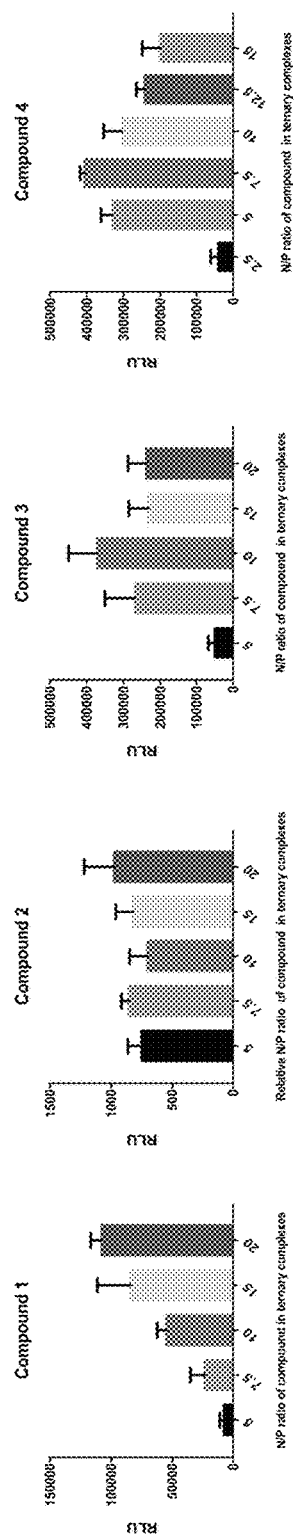
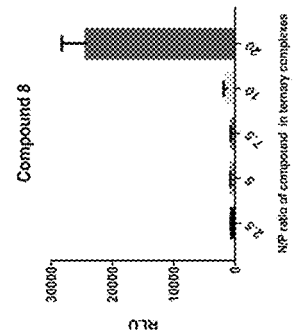
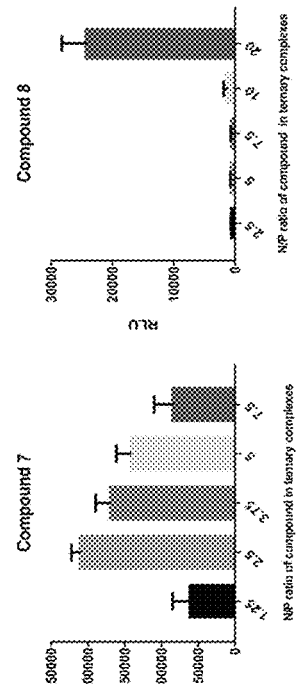
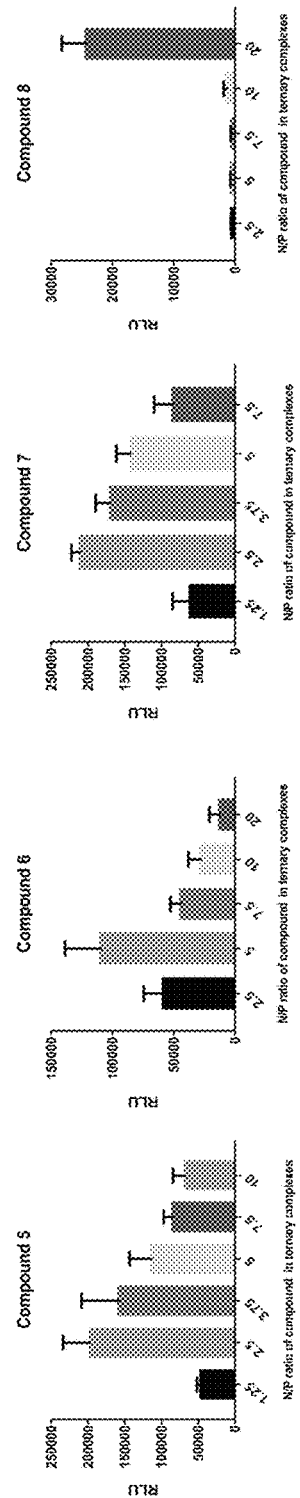
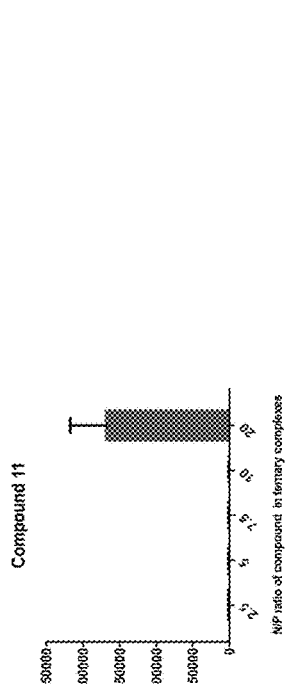
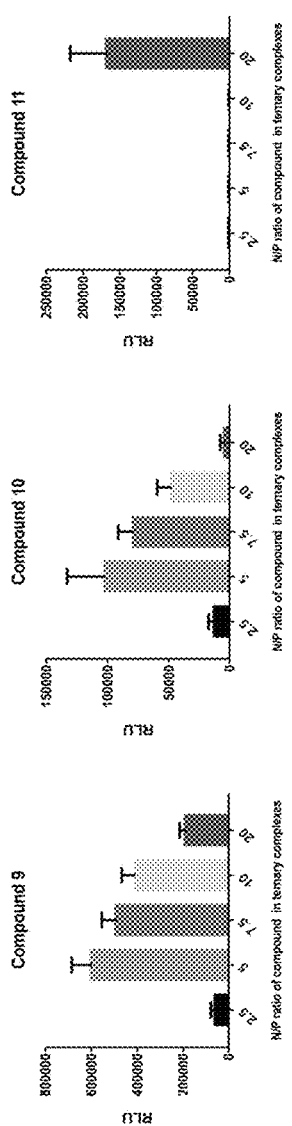
Fig. 15a, Fig. 15b, Fig. 15c, Fig. 15d, Fig. 15e, Fig. 15f, Fig. 15g, Fig. 15h, Fig. 15i, Fig. 15j, Fig. 15k

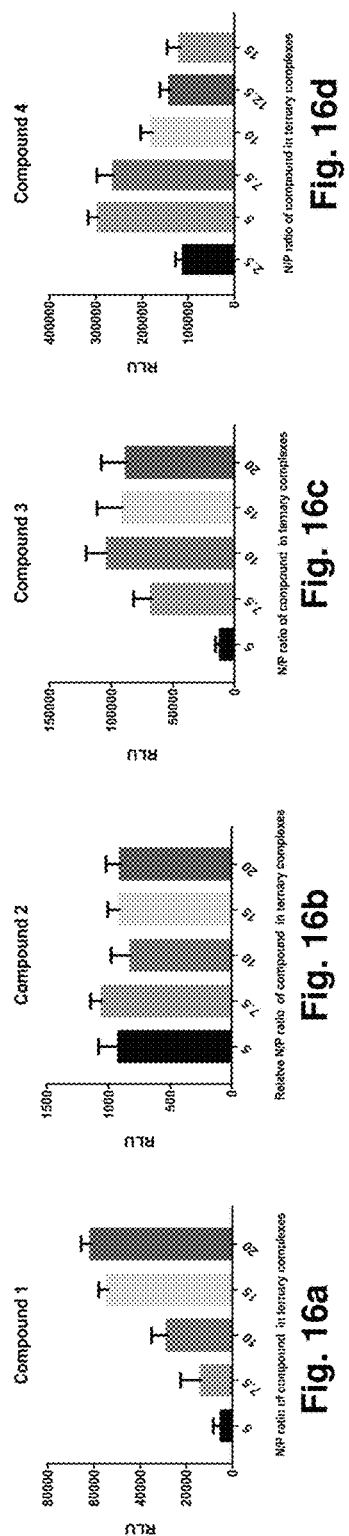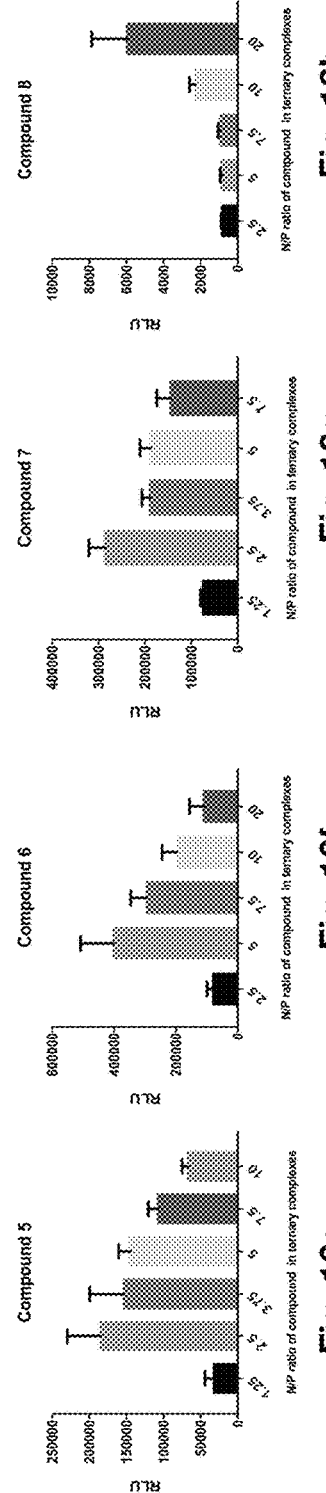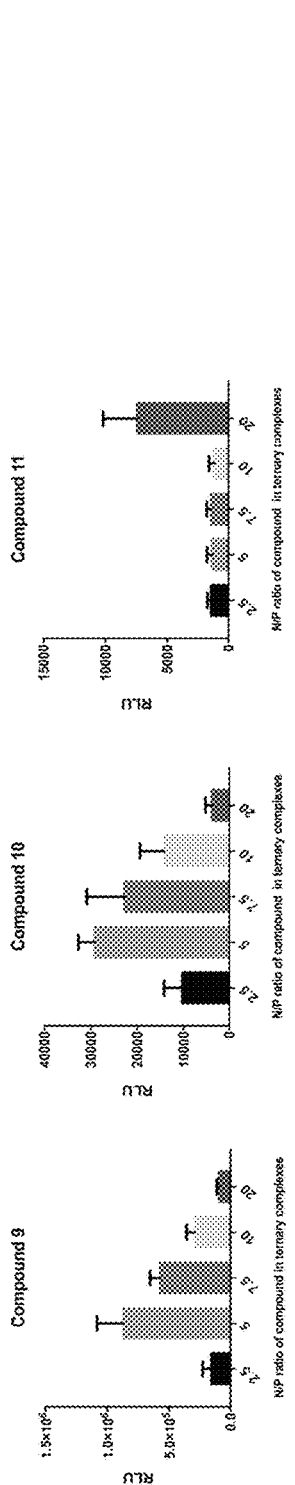
Fig. 16a – Fig. 16k

In vivo luminascence measurement

SYNTHETIC COMPOUND FOR IMPROVING EFFICIENCY OF TRANSFECTION

This application is a 371 national phase of International Patent Application No. PCT/EP2017/057530 filed Mar. 30, 2017, which claims priority to European Patent Application No. 16163326.8 filed Mar. 31, 2016, the contents of each of which applications is incorporated herein by reference.

This application contains a sequence listing submitted electronically via EFS-web, which serves as both the paper copy and the computer readable form (CRF) and consists of a file entitled "DGP-KUM-PAT1 NP_seqlist.txt", which was created on Sep. 23, 2018, which is 4,390 bytes in size, and which is herein incorporated by reference in its entirety.

The present invention concerns a synthetic compound for improving efficiency of transfection of eukaryotic cells by means of an amphiphilic block copolymer, the synthetic compound for use in the treatment of a genetically caused disease of a human being or an animal by gene therapy, a use of the synthetic compound and a method for an in vitro transfection of eukaryotic cells in cell culture.

Gene transfer to the eukaryotic cells has many potential applications in inherited and acquired diseases, such as cystic fibrosis and cancer. At the heart of a successful gene therapy approach lies a gene delivery vector that is relevant to the pathology and compatible with the therapeutic schedule. Viral vectors are usually very efficient at promoting gene transfer into eukaryotic cells, but they are very immunogenic and not suitable for repeated dosing. Non-viral gene delivery vectors are much less efficient in terms of transfection efficiency but usually less likely induce a strong inflammatory response than viral gene delivery vectors. Thus non-viral gene delivery vectors may be relevant in pathologies that require repeated administrations. Among the current non-viral vectors, cationic lipids and cationic polymers are extensively studied and have clearly demonstrated their transfection efficiency in vitro. However, aggregation in tissue fluids, toxicity and low in vivo efficiency have thus far hampered their clinical use. Poloxamine-based block copolymers, comprising poly(ethylene oxide) and poly(propylene oxide) blocks, represent an attractive class of new non-viral gene delivery vectors.

US 2010/0179212 A1 discloses a pharmaceutical composition which combines a tetrafunctional copolymer with a nucleic acid. The copolymer is a poloxamine. The poloxamine may be in the form of one of the cationic mineral or organic salts thereof. The composition can be used to improve in vivo gene transfer.

From Evans, R. K., et al., Journal of Pharmaceutical Sciences, Vol. 93, No. 7, July 2004, pages 1924 to 1939 and from Hartikka, J., et al., J. Gene Med. 2008, 10, pages 770 to 782 plasmid DNA vaccine formulations containing the nonionic triblock copolymer adjuvant CRL1005 together or without the cationic surfactant benzalkonium chloride (BAK) are known.

From Zhang, J., et al., J. Gene Med. 2013, 15(0), pages 271 to 281 the use of the poloxamine Tetronic® T904, a 4-arm polyethylene oxide/polypropylene oxide block copolymer for support of polycationic polymer/DNA complexes (polyplexes) based transfection is known. T904 significantly increased transfection efficiency of polyplexes based on 25 kDa branched polyethylenimine in a dose-dependent manner in the presence of serum in C6 glioma cells, human fibroblasts and mesenchymal stem cells.

Richard-Fiardo, P., et al., Biomaterials 2015 March, 45, pages 10 to 17 concerns the efficiency of the tetrafunctional block copolymer 704 as a non-viral gene delivery vector to the lungs of mice. The data obtained showed that the formulation 704 resulted in higher levels of reporter gene expression than the GL67A formulation currently being used in a clinical trial in cystic fibrosis patients. The inflammatory response associated with this gene transfer was lower than that induced by the GL67A formulation and the 704 formulation was amenable to repeated administrations.

From U.S. Pat. No. 8,058,068 B2 transfection compositions in which a peptide is covalently linked to a transfection agent such as a lipid, cationic lipid or dendrimer are known. The peptide-lipid conjugate may be combined in a mixture of non-conjugated cationic and/or neutral lipids and then combined with the nucleic acid to form a peptide-lipid-nucleic acid lipid aggregate which facilitates introduction of the anionic nucleic acid through the cell membranes. Peptides useful in transfection compositions include functional portions that are fusagenic, function for nuclear or other sub-cellular localization, function for transport or trafficking or are receptor ligands. The methods disclosed in U.S. Pat. No. 8,058,068 B2 involve contacting any cell, preferably a eukaryotic cell, with a transfection composition comprising a peptide including a fusagenic, membrane-permeabilizing, transport or trafficking sub-cellular-localization, or receptor ligand peptide, optionally conjugated to a nucleic acid-binding group, or optionally conjugated to the transfection agent (lipid or dendrimer) wherein said peptide is non-covalently associated with the nucleic acid. In one embodiment, a peptide-nucleic acid complex (where the peptide can be conjugated to a nucleic acid binding group) is formed and then combined with a cationic lipid for transfection.

EP 1 294 908 B1 discloses a synthetic peptide consisting of an oligo-lysine-DNA-binding sequence and an SV40-nuclear localization sequence for improvement of transfection.

WO 2010/118213 A2 discloses peptides including a nucleic acid binding domain and a nuclear localization domain in order to form a peptide-nucleic acid delivery construct.

The problem to be solved by the present invention is to provide an improved synthetic compound for improving efficiency of transfection and for use in the treatment of a disease, a use of such a compound and an improved method for an in vitro transfection of eukaryotic cells in cell culture. Furthermore, a pharmaceutical composition shall be provided.

The problem of the present invention is solved by the subject-matter of claims 1, 8, 9, 12 and 14. Embodiments of the invention are subject-matter of claims 2 to 7, 10, 11, 13 and 15.

According to the invention a synthetic compound for enabling transfection of eukaryotic cells by means of an amphiphilic block copolymer is provided. In particular, the synthetic compound may improve efficiency of transfection of eukaryotic cells by means of the amphiphilic block copolymer. The given purpose of enabling transfection of eukaryotic cells is achieved when in vitro transfection of eukaryotic cells in cell culture is enabled by use of the synthetic compound and the purpose of improving efficiency of transfection of eukaryotic cells is achieved when efficiency of in vitro transfection of eukaryotic cells in cell culture is improved by use of the synthetic compound vis-à-vis use of 25 kDa branched polyethylenimine (brPEI). The cell culture can be any cell culture system described in the embodiments, e. g. a cell culture system comprising human bronchial epithelial cells such as BEAS-2B cells or 16HBE cells.

The synthetic compound comprises a peptide residue having at least one targeting sequence and in addition a nucleic acid binding sequence which nucleic acid binding sequence comprises or consists of at least of four, in particular at least five, in particular at least six, in particular at least seven, in particular at least eight, in particular at least nine, consecutive amino acid residues which are positively charged at pH 7.4. The synthetic compound further comprises a hydrophobic moiety covalently linked to the peptide residue. The hydrophobic moiety comprises or consists of lipoic acid residue, lipoamide residue, a tetradecyl residue, a cholesteryl residue, or a further peptide residue having a sequence with more than 40% amino acid residues with hydrophobic side chains. This further peptide residue may comprise or consist of at least of four, in particular at least five, in particular at least six, in particular at least seven, in particular at least eight, in particular at least nine, amino acid residues with hydrophobic side chains. The amino acid residues with hydrophobic side chains may be consecutive amino acid residues.

The targeting sequence is any sequence that causes a direction of the sequence to a position or a structure inside or on the surface of eukaryotic cells. The targeting sequence may be a ligand for a specific receptor on the surface of specific cells, such as a Fc receptor, or a sequence which specifically binds to a structure on the surface of or inside specific cells. In particular the targeting sequence comprises or consists of a nuclear localization signal (NLS) sequence, a skeletal muscle cell ligand, a myocardium ligand, and/or an epithelium ligand sequence, in particular a human airway epithelium ligand sequence. The targeting sequence(s) allow(s) it to specifically direct the nucleic acid to be transfected to the cells that should be transfected and/or to a specific compartment inside of cells in which compartment the nucleic acid shall exert its effect. The synthetic compound according to the invention may comprise two or more targeting sequences, e. g. an epithelium ligand sequence for directing the nucleic acid to be transfected to epithelium cells and a NLS for directing the nucleic acid to the nucleus of these epithelium cells.

The synthetic compound according to the invention may be modified for preventing a degradation inside an organism, e. g. by PEGylation, i. e. a covalent or non-covalent attachment of polyethylene glycol to the synthetic compound.

Even though poloxamine-based block copolymers are promising non-viral gene delivery vectors for in vivo application, the inventors of the present invention recognized that they are rather poor transfection agents in delivering nucleic acids into cultured cells. Data obtained from in vitro transfection study on airway epithelium cells revealed that transfection efficiency of complexes formed by in vitro transcribed (IVT) messenger RNA expressing Luciferase (MetLuc mRNA) and a broad range of concentrations of poloxamine 704 were all lower than 600 relative light units (RLU) per mg of cellular protein, which is similar to the intensity of background signal.

The inventors found that an improvement of the in vitro efficiency of transfection by means of an amphiphilic block copolymer also improves the in vivo efficiency of transfection by means of the amphiphilic block copolymer. They also found that the synthetic compound according to the invention drastically improved efficiency of transfection by means of an amphiphilic block copolymer. They further found that the synthetic compound, the nucleic acid to be transfected and the amphiphilic block copolymer form a ternary complex which ternary complex very efficiently effects transfection of the nucleic acid. The nucleic acid may be an RNA, for example an mRNA, in particular an in vitro transcribed messenger RNA (IVT-mRNA) or an siRNA, or a DNA and it may be present as a plasmid (pDNA or pRNA), a single strand or a double strand.

The inventors revealed that the highest transfection of MetLuc mRNA containing ternary complexes on cultured airway epithelium cells could reach around 870,000 RLU/mg cellular protein which is more than 35 times higher than that that could be reached with branched-polyethylenimine (brPEI, 25 kDa) based polymers which are considered as the "gold standard" in the art. In addition, the synthetic compound of the present invention also greatly supported poloxamine 704 mediated transfection of pDNA expressing Luciferase (MetLuc). After adding a synthetic compound according to the invention, in vitro transfection efficiency of poloxamine 704/MetLuc pDNA significantly enhanced from background level to 2,163,410 RLU/mg cellular protein in airway epithelium cells after 3 days of incubation. The transfection efficiency was even significantly higher than a corresponding transfection efficiency achieved by use of Lipofectamine® 2000. Lipofectamine is a mixture of DOSPA:DOPE at a weight ratio of 3:1. DOSPA is 2,3-dioleyloxy-N-(2-(sperminecarboxamido)ethyl)-N,N-dimethyl-1-propanaminium trifluoroacetate ($C_{54}H_{107}N_6O_5^+$). DOPE is Dioleoylphosphatidylethanolamine ($C_{41}H_{78}NO_8P$).

The effect of the nucleic acid binding sequence is that it causes a condensation of nucleic acids and facilitates an efficient cytoplasmic localization. The number and sequence of amino acid residues positively charged at pH 7.4 can vary. The positively charged amino acid residues may comprise or consist of histidine residue(s), arginine residue(s), lysine residue(s) and/or positively charged analog(s) of amino acid residue(s) and in particular only comprise or consist of arginine residue(s) and/or lysine residue(s). The amino acid residue(s) may be L-isomer(s) or D-isomer(s). The histidine residues(s) may be alpha-histidine or beta-histidine residue(s), the arginine residues(s) may be alpha-arginine or beta-arginine residue(s) and the lysine residues(s) may be alpha-lysine or beta-lysine residue(s). Different numbers and combinations of lysine residue(s), arginine residue(s), histidine residue(s), and positively charged analog(s) of amino acid residue(s) result in different condensing profiles and endosome/lysosome escaping ability. The positively charged analog of the amino acid residue may be an analog of an aspartic acid residue such as a residue of an N-substituted aspartamide, d-aspartamide, or beta-aspartamide, or an analog of a glutamatic acid residue such as a residue of an N-substituted glutamide, d-glutamide, or beta-glutamide. "N-substituted" means that the carboxyl group on the side chain of aspartic acid residue or glutamic acid residue is modified with a chemical group containing primary, secondary and/or tertiary amine(s). For example, an N-substituted aspartamide may be

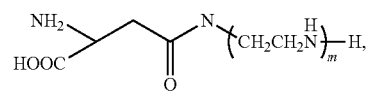

wherein m≥1 and an N-substituted glutamide may be

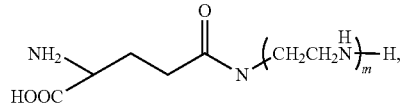

wherein m≥1.

The hydrophobic moiety can be covalently linked to any part of the peptide residue. In one embodiment of the invention the hydrophobic moiety is covalently linked to the amino terminus or to the carboxy terminus or to any side chain, in particular the side chain of lysine, of any amino acid residue of the peptide residue. The further peptide residue may have a sequence with more than 50% amino acid residues with hydrophobic side chains. Side chains of amino acids are considered as hydrophobic if the hydrophobicity index at pH 2 and pH 7 according to the following table disclosed in www.sigmaaldrich.com is above 40:

| At pH 2* | | At pH 7** | |
|---|---|---|---|
| Very Hydrophobic | | | |
| Leucine (leu) | 100 | Phenylalanine (phe) | 100 |
| Isoleucine (ile) | 100 | Isoleucine (ile) | 99 |
| Phenylalanine (phe) | 92 | Tryptophan (trp) | 97 |
| Tryptophan (trp) | 84 | Leucine (leu) | 97 |
| Valine (val) | 79 | Valine (val) | 76 |
| Methionine (met) | 74 | Methionine (met) | 74 |
| Hydrophobic | | | |
| Cysteine (cys) | 52 | Tyrosine (tyr) | 63 |
| Tyrosine (tyr) | 49 | Cysteine (cys) | 49 |
| Alanine (ala) | 47 | Alanine (ala) | 41 |
| Neutral | | | |
| Threonine (thr) | 13 | Threonine (thr) | 13 |
| Glutamic acid (glu) | 8 | Histidine (his) | 8 |
| Glycine (gly) | 0 | Glycine (gly) | 0 |
| Serine (ser) | −7 | Serine (ser) | −5 |
| Glutamine (gln) | −18 | Glutamine (gln) | −10 |
| Aspartic acid (asp) | −18 | | |
| Hydrophilic | | | |
| Arginine (arg) | −26 | Arginine (arg) | −14 |
| Lysine (lys) | −37 | Lysine (lys) | −23 |
| Asparagine (asn) | −41 | Asparagine (asn) | −28 |
| Histidine (his) | −42 | Glutamic acid (glu) | −31 |
| Proline (pro) | −46 | Proline (pro) | −46 (used pH 2) |
| | | Aspartic acid (asp) | −55 |

*pH 2 values: Normalized from Sereda et al., J. Chrom. 676: 139-153 (1994).
**pH 7 values: Monera et al., J. Protein Sci. 1: 319-329 (1995).

The hydrophobicity index indicates relative hydrophobicity and therewith how soluble an amino acid is in water. Values in the table are normalized by giving the most hydrophobic residue a value of 100 relative to glycine, which is considered neutral (0 value). The scales were extrapolated to residues which are more hydrophilic than glycine.

Amino acid residues with hydrophobic side chains are in particular amino acid residues of leucine, isoleucine, phenylalanine, tryptophan, valine, methionine, cysteine, tyrosine, alanine and their derivatives, in particular amino acid residues of phenylalanine, tyrosine and tryptophan.

An advantage of the lipoic acid residue is that lipoic acid is produced naturally in the human body and commonly used as an antioxidant drug for treating diseases such as diabetes and HIV.

Hydrophobicity and therewith efficiency of transfection can further be increased by amidation of the carboxy terminus of the peptide residue such that the C-terminus of the peptide residue is formed by a —$CONH_2$ moiety.

The lipoic acid residue and the lipoamide residue can firmly interact with the hydrophobic part of the amphiphilic block copolymer. The disulfide bond localized in the dithiolane of the lipoic acid residue and the lipoamide residue can be specifically cleaved by glutathione (GSH) which exists in high level in the cytoplasm of eukaryotic cells. As a result hydrophobicity of the lipoic acid residue or the lipoamide residue is decreased and its interaction with the amphiphilic block copolymer is weakened. This is followed by release of the synthetic compound according to the invention from the amphiphilic block copolymer and an enhanced release of the nucleic acid from the delivery system. As a result a higher transfection rate is achieved.

The peptide residue may consist of the targeting sequence and the nucleic acid binding sequence. The peptide residue, optionally together with the further peptide residue, may comprise or consist of amino acid sequence SEQ ID NO: 1, SEQ ID NO: 2, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

The maximal length of the peptide residue, optionally together with the further peptide residue, may be 45, in particular 41, in particular 30, in particular 26, in particular 20, in particular 17, in particular 15, in particular 12, in particular 11, amino acid residues. The shorter the peptide residue, optionally together with the further peptide residue, is the lesser is the probability that it exerts an antigenic effect. This may be particular important if repeated administration is intended.

The synthetic compound may consist of the peptide residue and the hydrophobic moiety.

The invention also concerns the synthetic compound according to the invention for use in the treatment of a genetically caused disease of a human being or an animal by gene therapy or by an immunotherapy or for use in preventing an infection by vaccination, wherein the synthetic compound is used together with the amphiphilic block copolymer and a nucleic acid to be transferred in cells of the human being or the animal. The synthetic compound can be present in a nebulized form. The animal may be a mammal. The genetically caused disease may be cystic fibrosis or a cancer. In case of an immunotherapy of a genetically caused disease, such as a cancer, the nucleic acid may code for a specific antigen, in particular a surface antigen, specifically expressed by cells effected by a genetic alteration causing the genetically caused disease. In case of use in preventing an infection by vaccination the infection may be an infection by a virus or a pathogen such as a pathogenic microorganism. In this case the nucleic acid may code for a specific antigen, in particular a surface antigen, specifically expressed by cells infected with the virus or the pathogen or a surface antigen of the virus or the pathogen. In both cases, the immunotherapy and the prevention of an infection by vaccination, the expression of the transfected nucleic acid results in the generation of peptides or proteins causing an immunoreaction of the treated human being or animal. In cases of the immunotherapy or the vaccination the synthetic compound according to the invention may be subcutaneously injected together with the amphiphilic block copolymer and the nucleic acid in the human being or animal. The nucleic acid may be a DNA, in particular a DNA present in a plasmid (pDNA) or an mRNA, in particular an IVT-mRNA.

The invention also concerns a pharmaceutical composition comprising any synthetic compound according to the invention together with a pharmaceutically acceptable carrier. The pharmaceutically acceptable carrier may comprise or consist of water or a salt solution, in particular a physiologic salt solution, Tyrode's solution, an Eagle's Minimum Essential Medium such as Opti-MEM® (purchased from ThermoFisher Scientific), a sodium chloride solution or a calcium chloride solution. The pharmaceutical composition may also be prepared as a dry powder formulation. In this case the pharmaceutically acceptable carrier can comprise or consist of an albumin, a polyethylene glycol (PEG), or a saccharide such as trehalose, mannose or mannitol. The pharmaceutical composition may also comprise the previously described nucleic acid and the previously described amphiphilic block copolymer. The pharmaceutical composition may be for use in the treatment of a genetically caused disease of a human being or an animal by gene therapy.

The invention further concerns the use of the synthetic compound according to the invention together with an amphiphilic block copolymer and a nucleic acid to be transferred in eukaryotic cells for an in vitro transfection of the eukaryotic cells in cell culture.

The invention also concerns a method for an in vitro transfection of eukaryotic cells in cell culture comprising the following steps:

a1) Mixing a plurality of molecules of the synthetic compound according to the invention with a plurality of molecules of an amphiphilic block copolymer to allow the formation of binary complexes, b1) mixing the formed complexes with a plurality of molecules of a nucleic acid to be transferred into the cells to allow the formation of ternary complexes, or a2) mixing a plurality of molecules of a nucleic acid to be transferred into the cells with a plurality of molecules of an amphiphilic block copolymer to allow the formation of binary complexes, b2) mixing the formed complexes with a plurality of molecules of the synthetic compound according to the invention to allow the formation of ternary complexes and c) contacting the ternary complexes with the cells to be transfected.

In each case of the synthetic compound for use in the treatment of a genetically caused disease, the use of the synthetic compound and the method for the in vitro transfection, the amphiphilic block copolymer may be a poloxamer, in particular poloxamer 184 (designated L64) or a poloxamine, in particular an ethylene oxide-propylene oxide copolymer with tetraether with (1,2-ethanedinitrilo)tetrakis (propanol), in particular poloxamine 304 (designated P304), 704 (designated P704), 904 (designated P904) or 90R4 (designated P90R4).

The invention is further illustrated on basis of the following embodiments.

FIGS. 2a to 2d show in vitro transfection profiles of MetLuc mRNA or pDNA containing poloxamine 704 (P704) based binary complexes in BEAS-2B and 16HBE cells.

Figure 1:
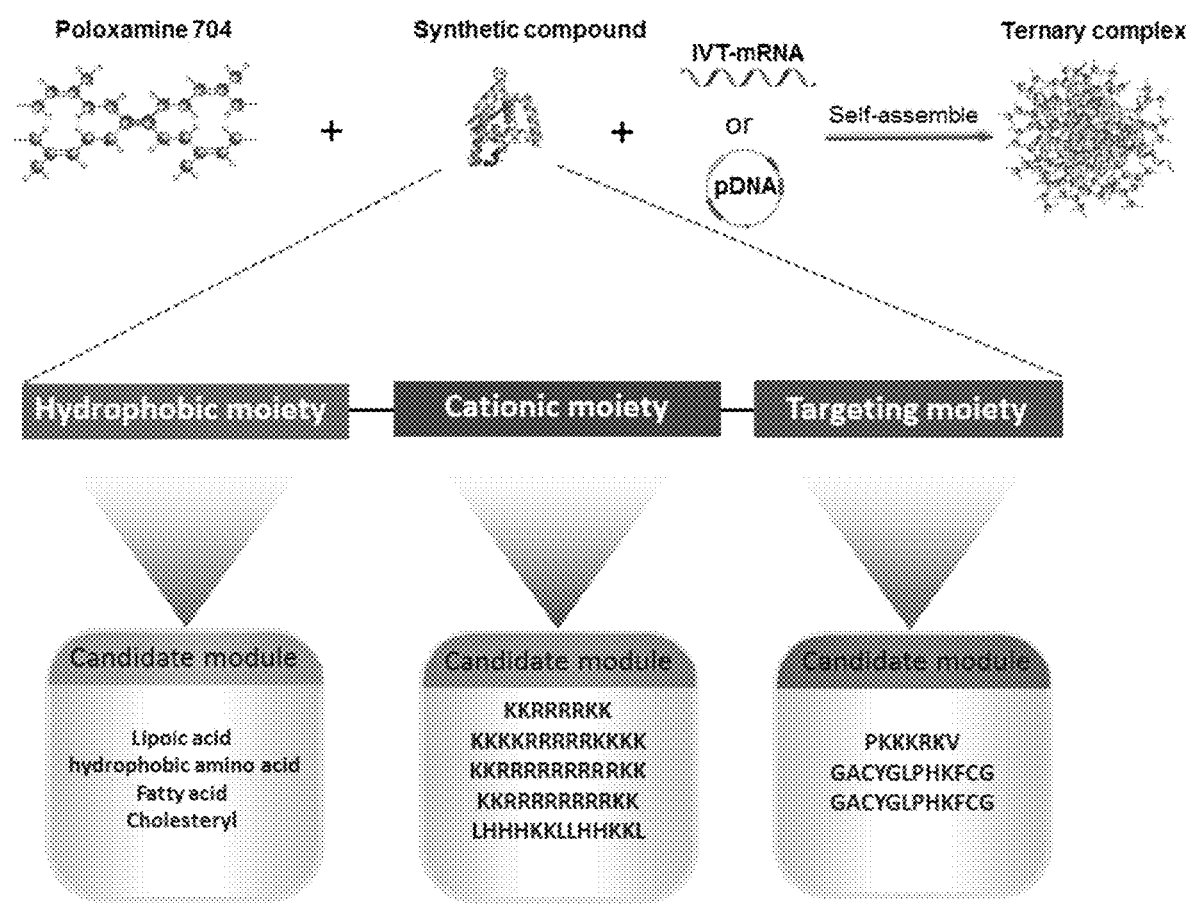
FIG. 1 shows schematically a use of synthetic compounds according to the invention together with P704 and IVT-mRNA or pDNA.
Figure 3A:
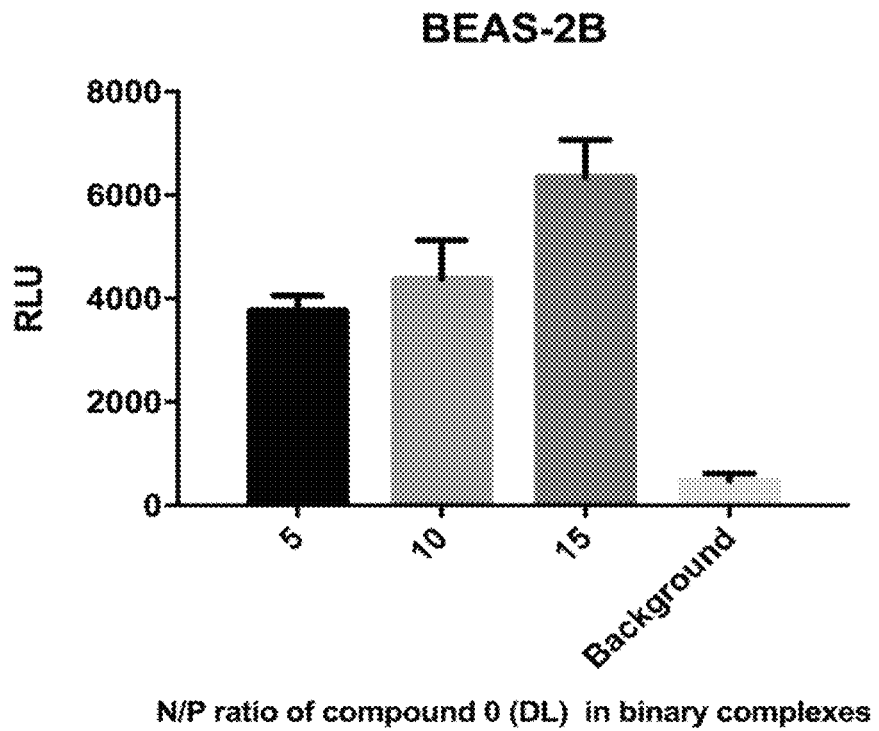
FIGS. 3a to 3d show in vitro transfection profiles of binary complexes (compound 0 (DL)+IVT-mRNA or pDNA) in cultured human bronchial cells (BEAS-2B and 16HBE cells).
Figure 3B:
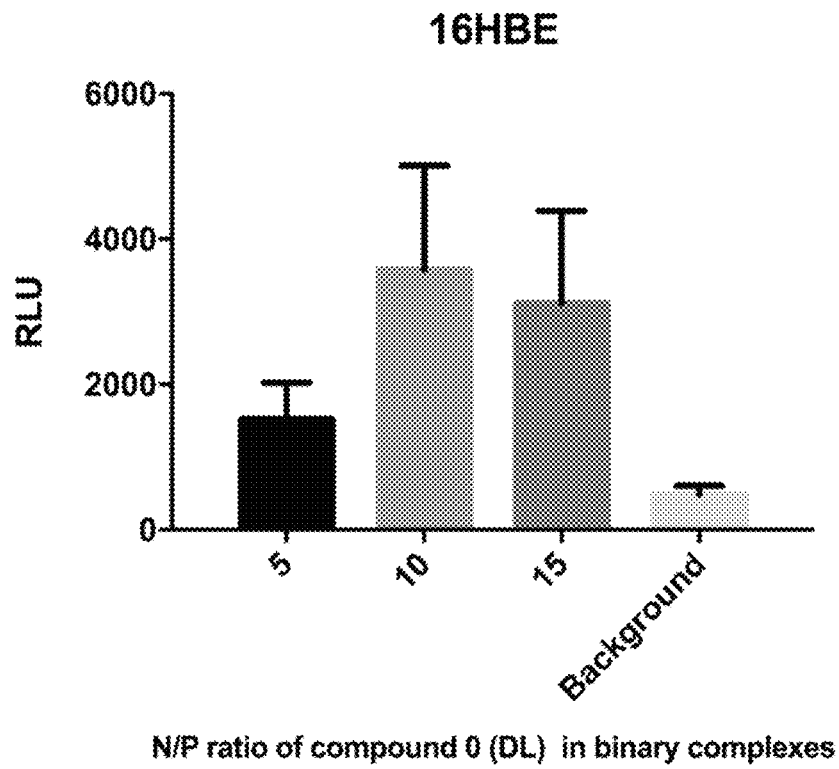
Figure 3C:
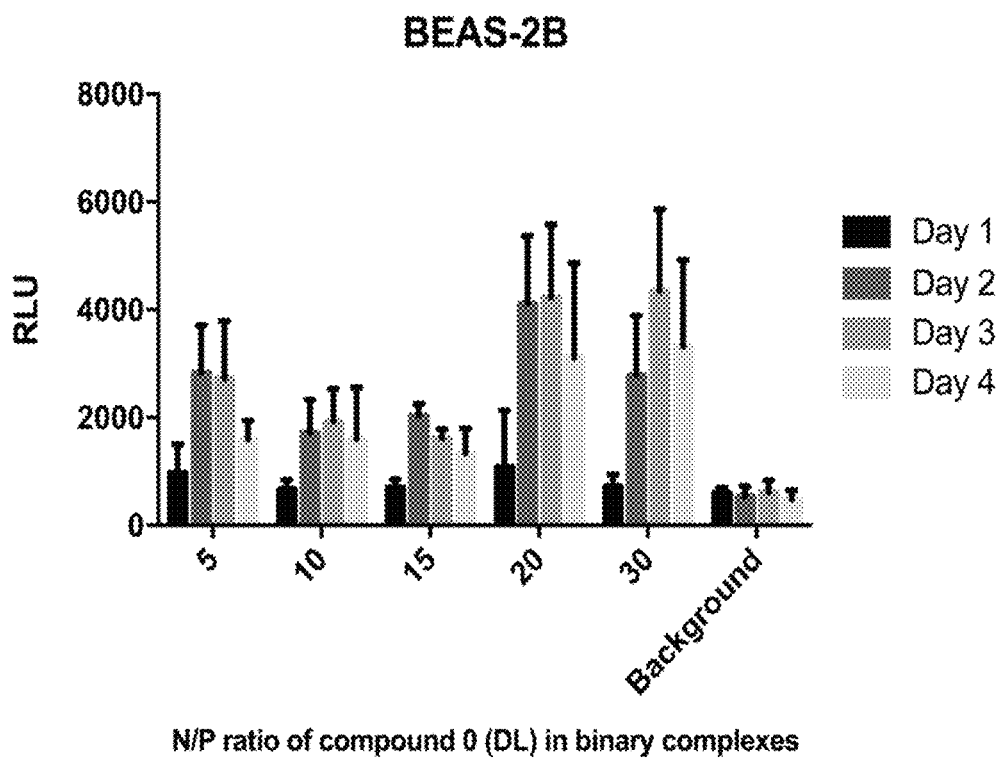
Figure 3D:
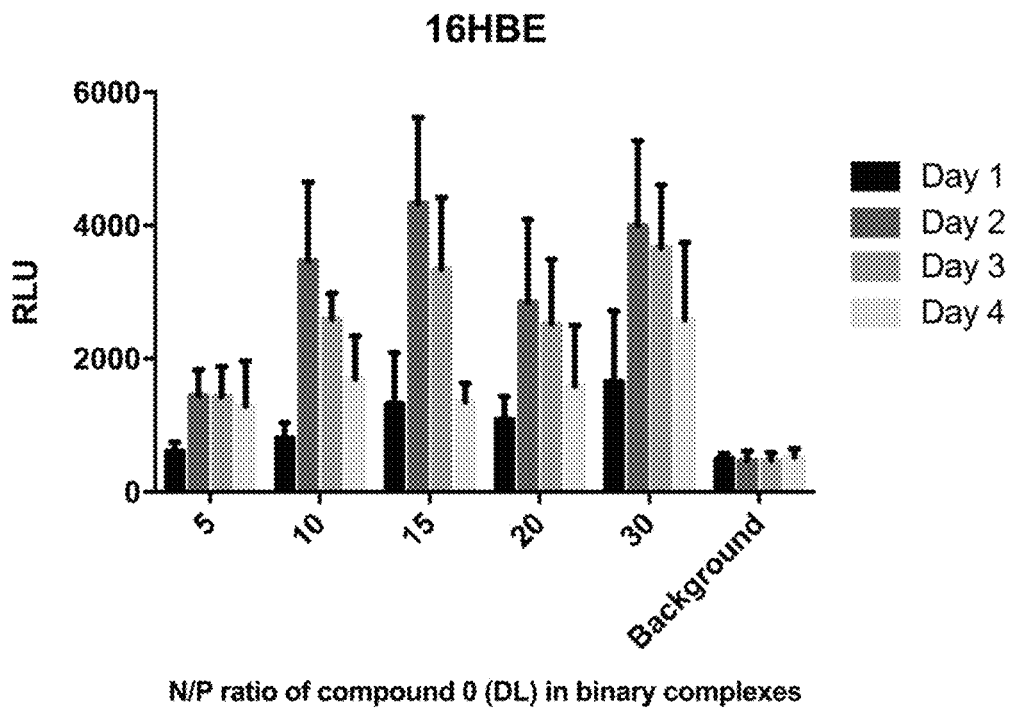
Figure 4A:
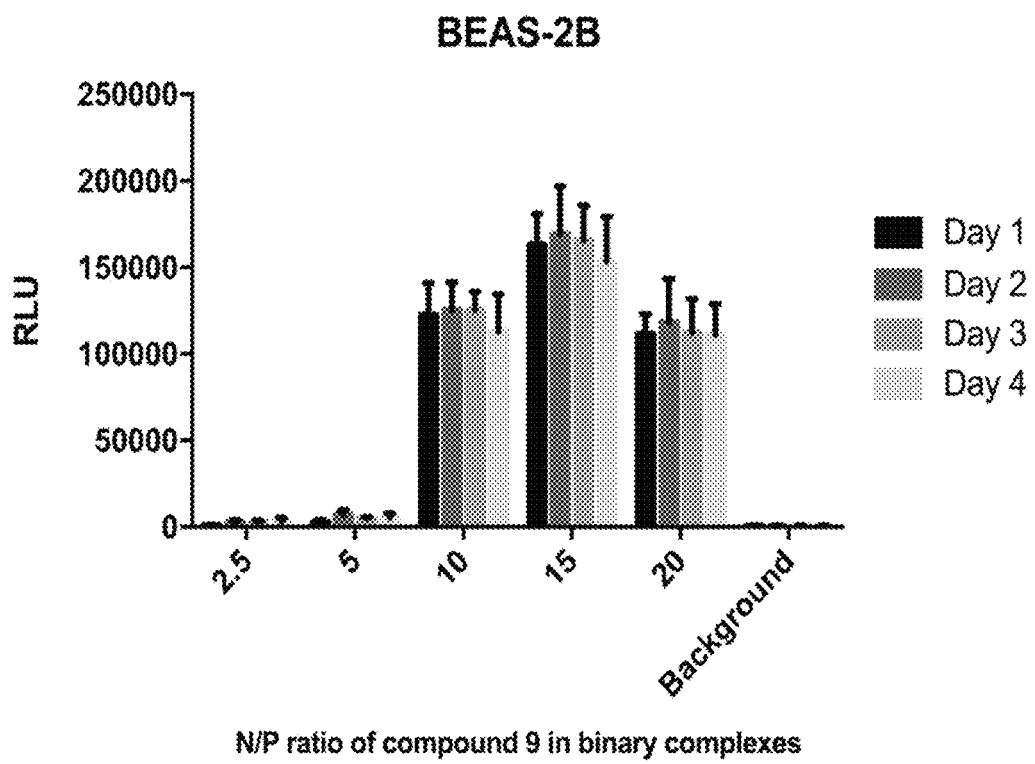
FIGS. 4a and 4b show in vitro transfection profiles of binary complexes (compound 9+pDNA) in cultured human bronchial cells.
Figure 4B:
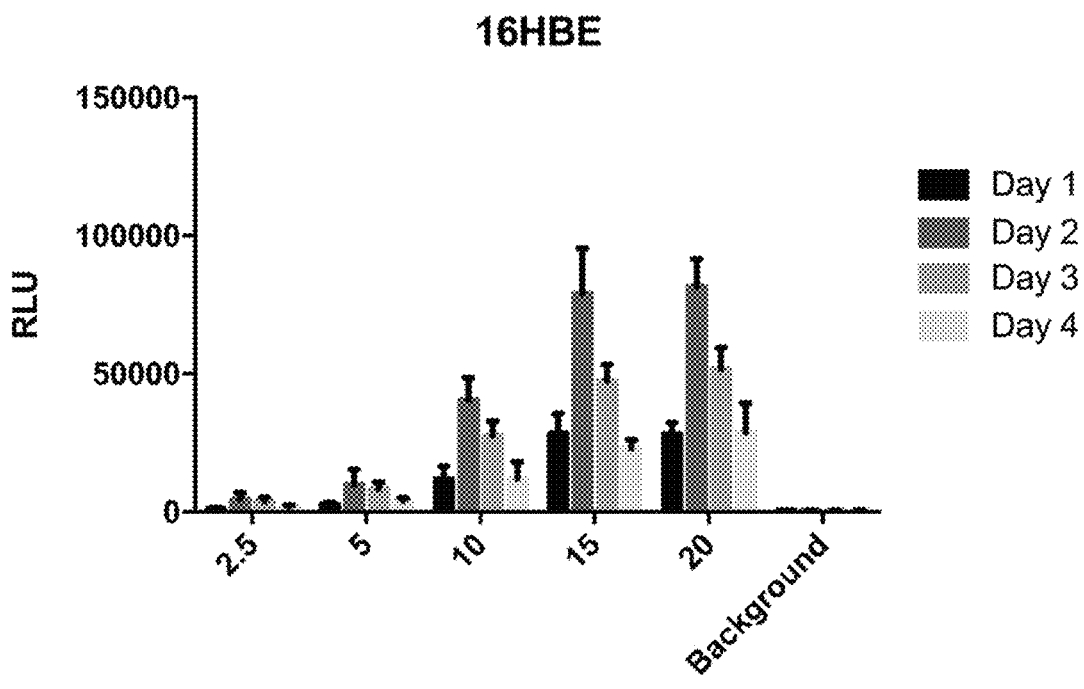
Figure 5A:
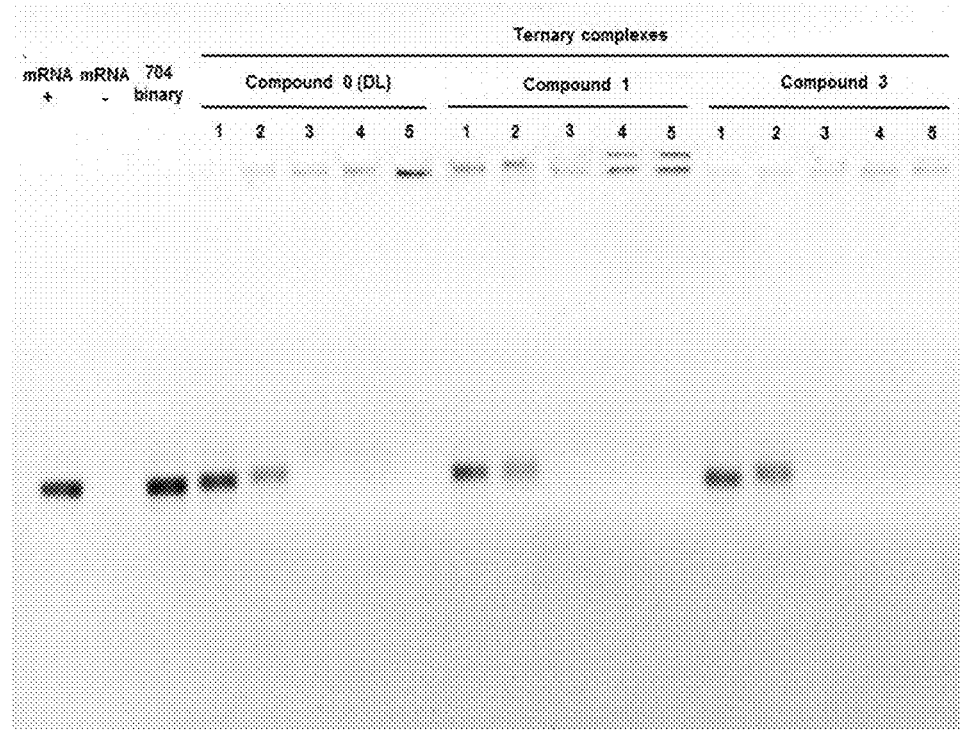
Figure 5B:
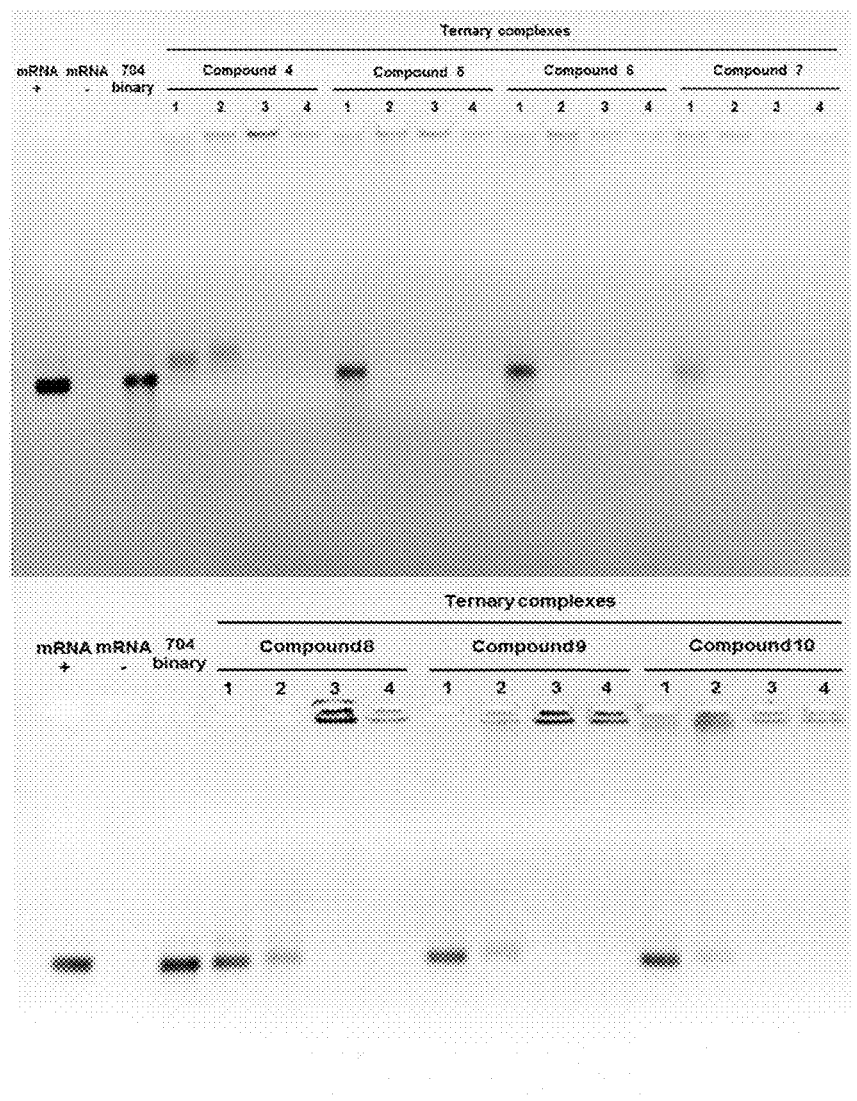
Figure 5C:
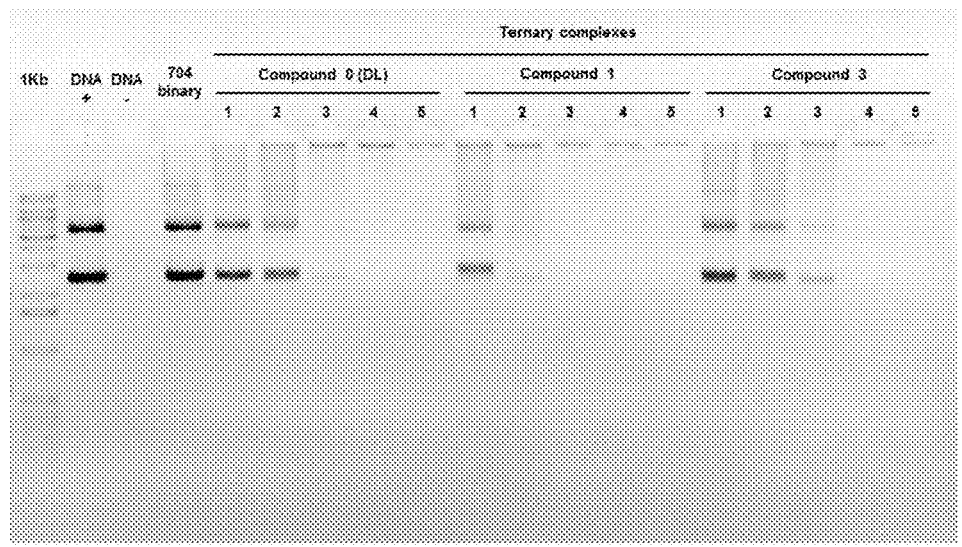
Figure 5D:
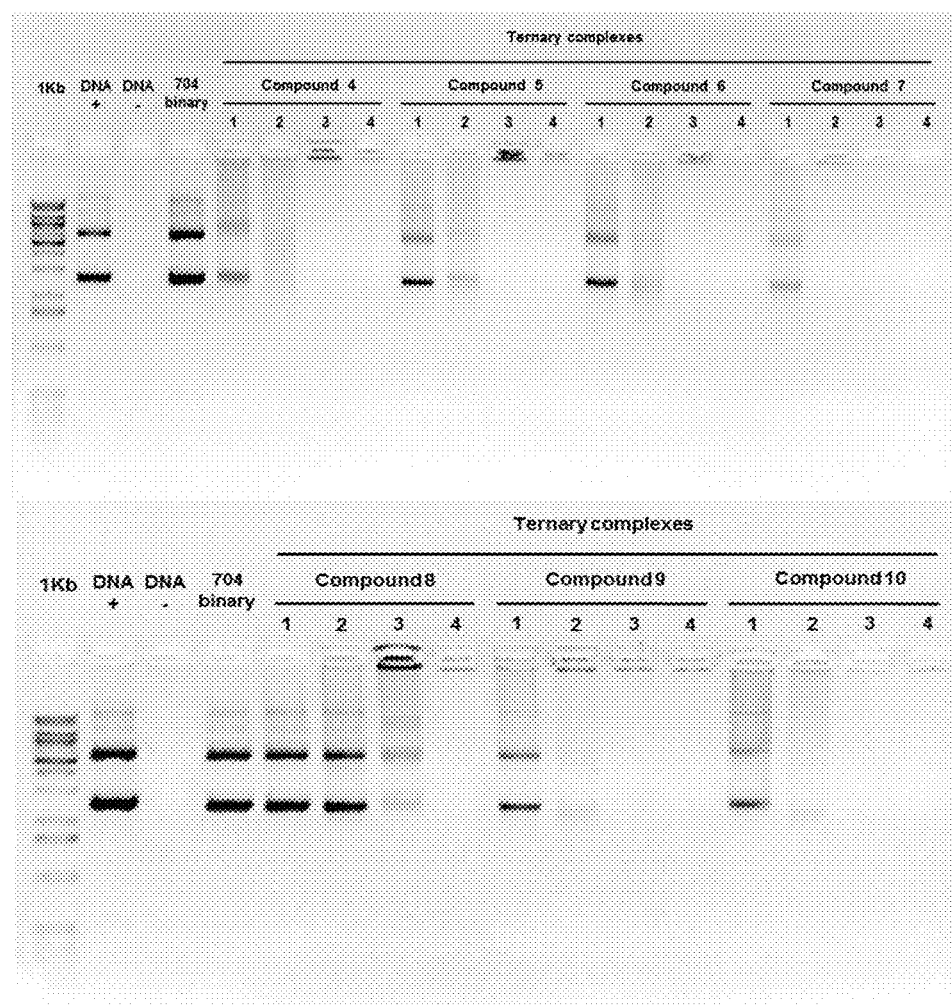
Figure 5E:
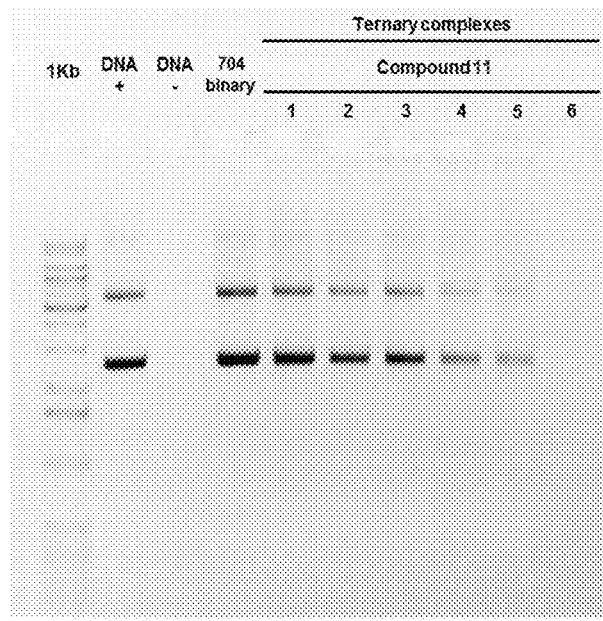
Figure 5F:
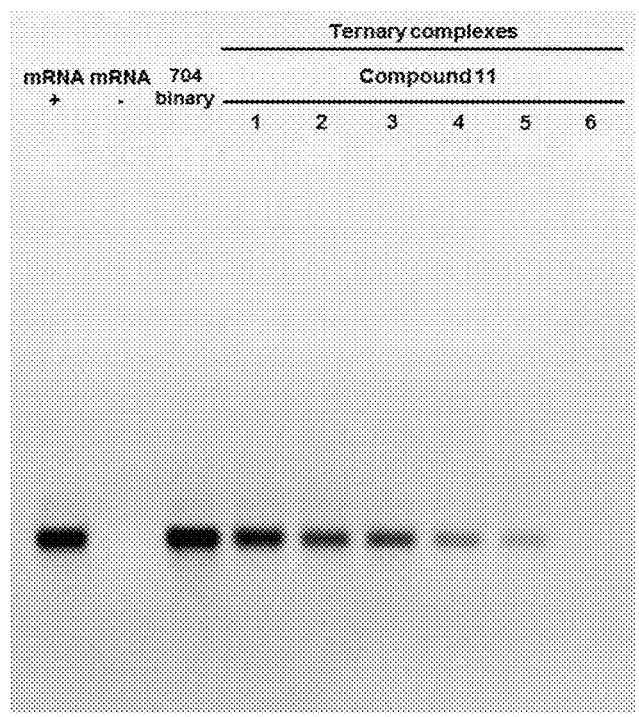
Figure 5G:
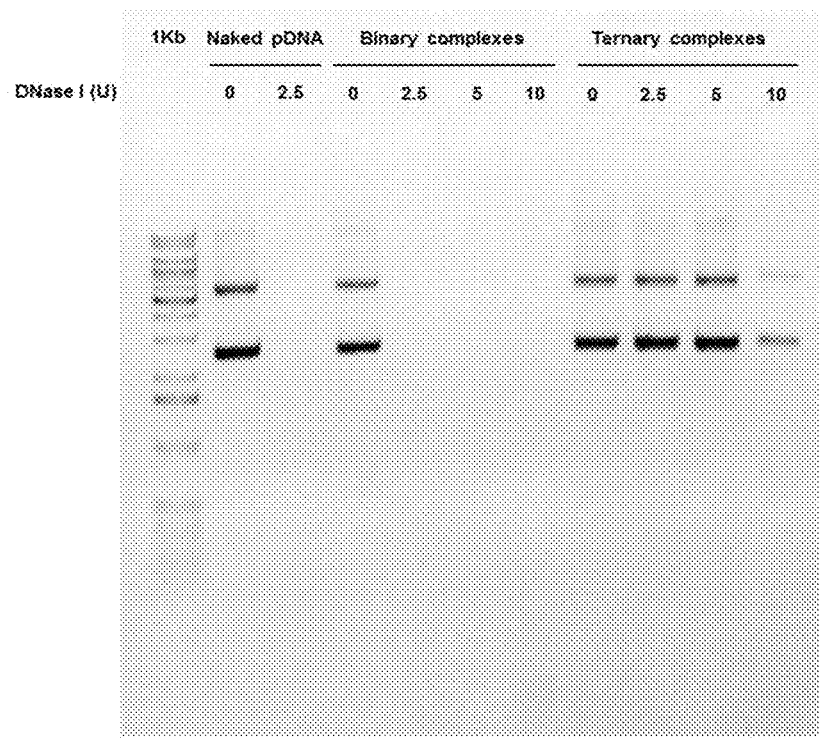
Figure 6A:
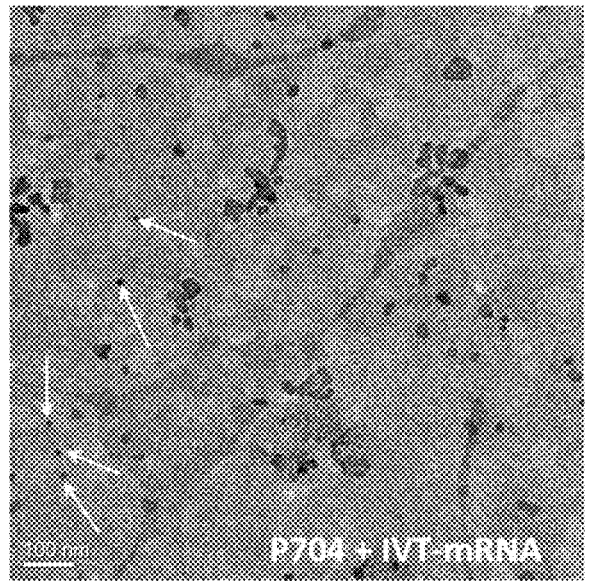
Figure 6B:
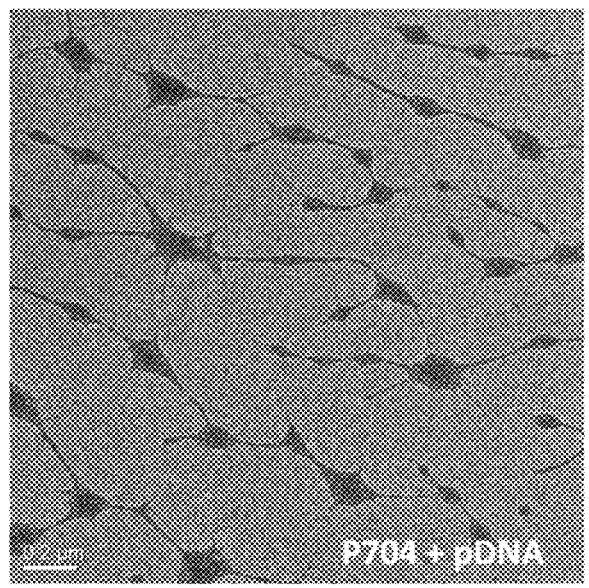
Figure 6C:
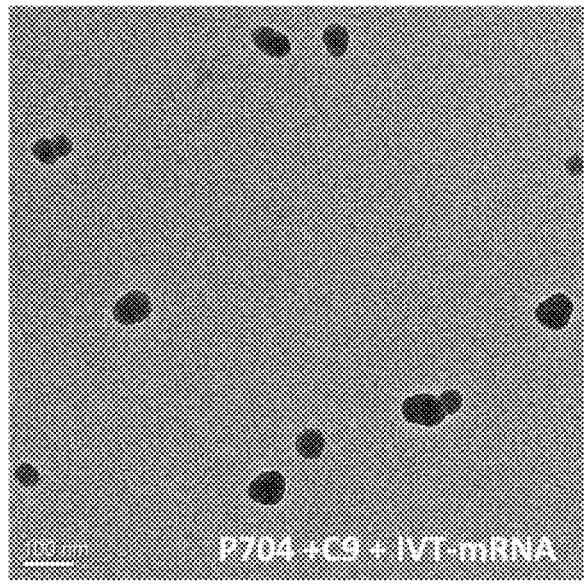
Figure 6D:
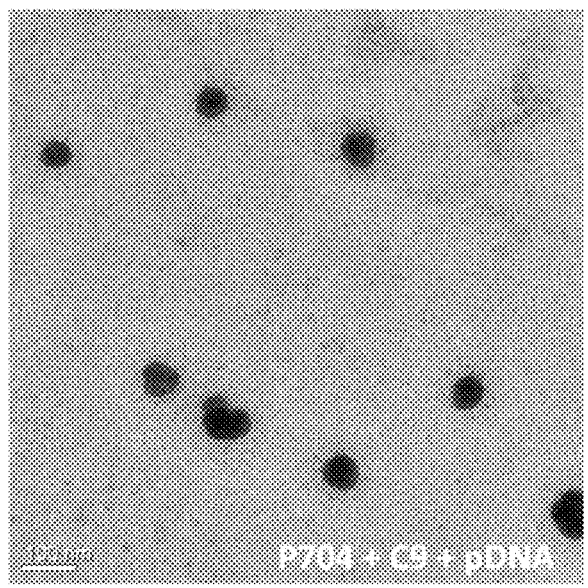
Figure 7B:
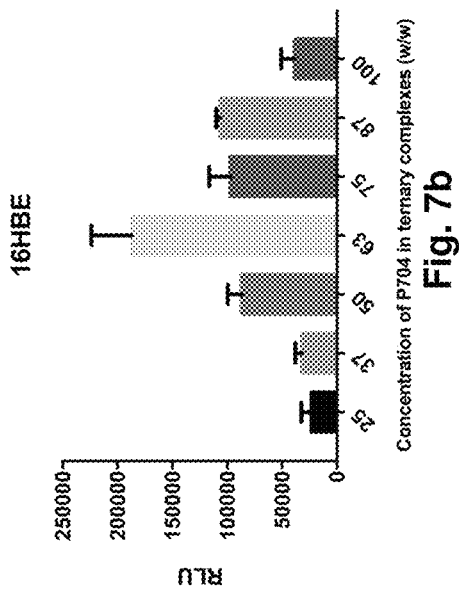
Figure 7D:
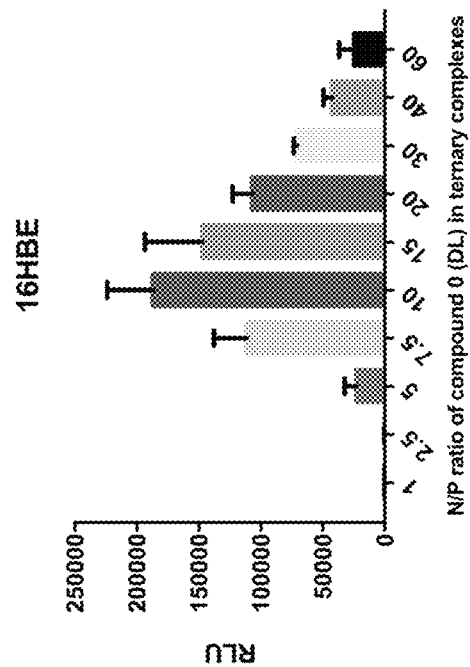
Figure 7A:
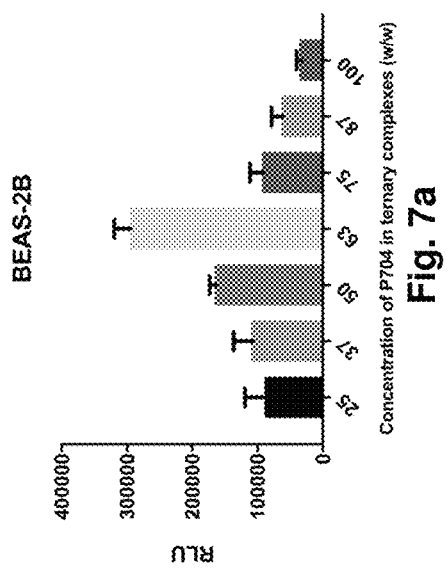
Figure 7C:
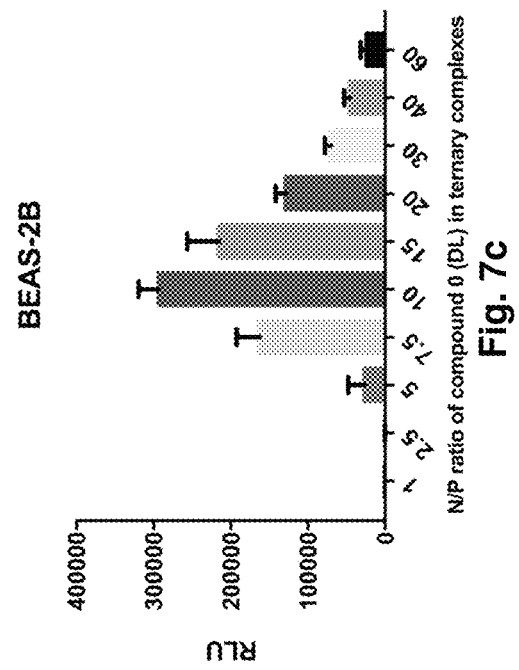

FIGS. 5a to 5g FIGS. 5a to 5f show agarose gel electrophoresis of IVT-mRNA and pDNA containing P704 based binary and ternary complexes. FIG. 5g shows the result of an experiment concerning the stability of pDNA containing P704 based binary and ternary complexes containing compound 9 in presence of increasing DNase I activity (2.5 U to 10 U).

FIGS. 6a to 6d show TEM micrographs of P704-based binary complexes and ternary complexes. Noncomplexed IVT-mRNA was marked with arrow in FIG. 6a.

FIGS. 7a to 7d show in vitro transfection efficiencies of MetLuc mRNA containing ternary complexes in human epithelial cells depending on the concentration of P704 and compound 0 (DL).

FIGS. 8a to 8d show in vitro transfection efficiencies of MetLuc pDNA containing ternary complexes in human epithelial cells depending on the concentration of P704 and compound 0 (DL).

FIGS. 9a to 9d show results of assays for optimisation of parameters influencing in vitro transfection of P704 based ternary complexes using IVT-mRNA.

Figure 10:
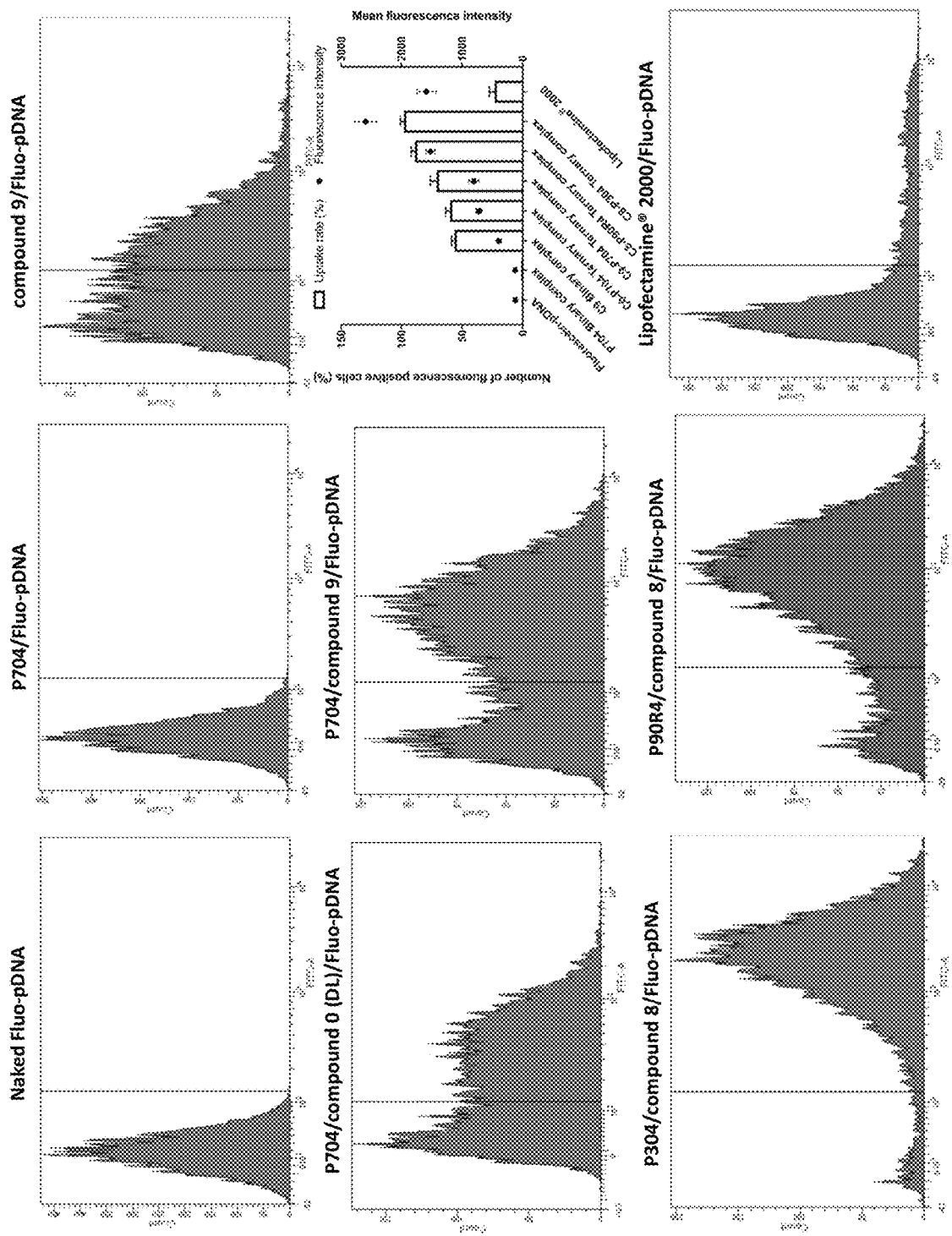

FIG. 10 shows the result of flow cytometry analysis of endocytic uptake of fluorescein labled pDNA (Fluo-pDNA), P704/Fluo-pDNA binary complexes, compound 9/Fluo-pDNA binary complexes, Lipofectamine® 2000 based lipoplex and compound 0 (DL) (C0), compound 8 (C8), or compound 9 (C9) containing ternary complexes in 16HBE cells.

FIGS. 11a to 11d show the influence of low temperature and different inhibitors on the endocytosis of Fluo-pDNA containing P704 based ternary complexes in 16HBE cells. The cellular uptake of non-inhibited compound 9 containing ternary complexes were used as control for FIGS. 11a, 11b and 11c, while the cellular uptake of non-inhibited compound 0 (DL) containing ternary complexes were set as control for FIG. 11d.

FIGS. 12a to 12k show transfection efficiencies of MetLuc pDNA containing P704 based ternary complexes comprising different synthetic compositions according to the invention in BEAS-2B cells.

FIGS. 13a to 13k show transfection efficiencies of MetLuc pDNA containing P704 based ternary complexes comprising different synthetic compositions according to the invention in 16HBE cells.

Figure 14A:
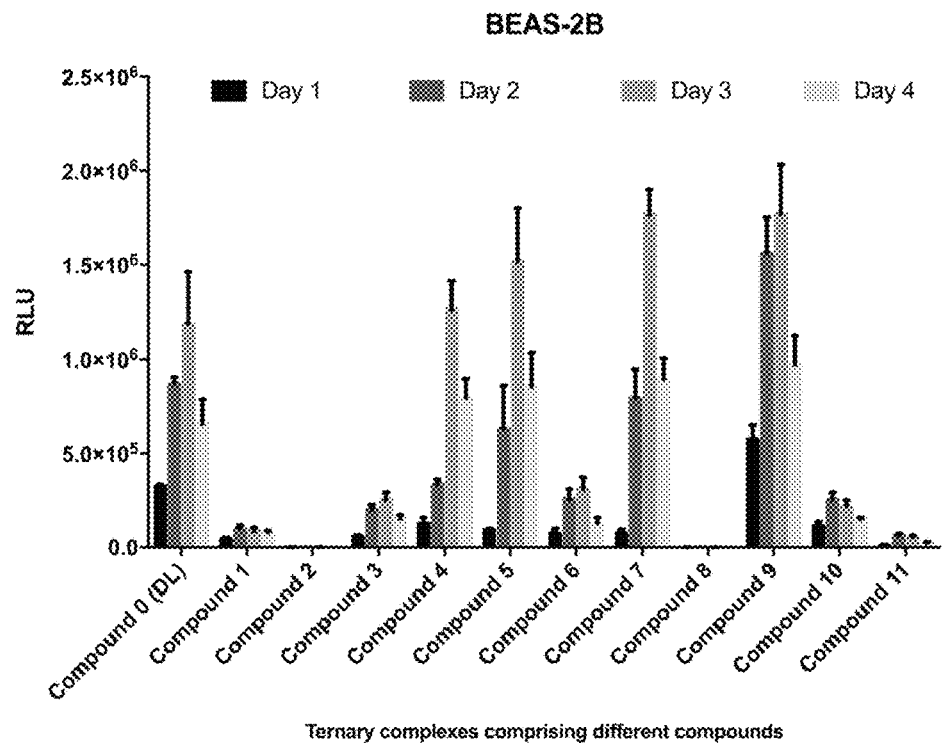
Figure 14B:
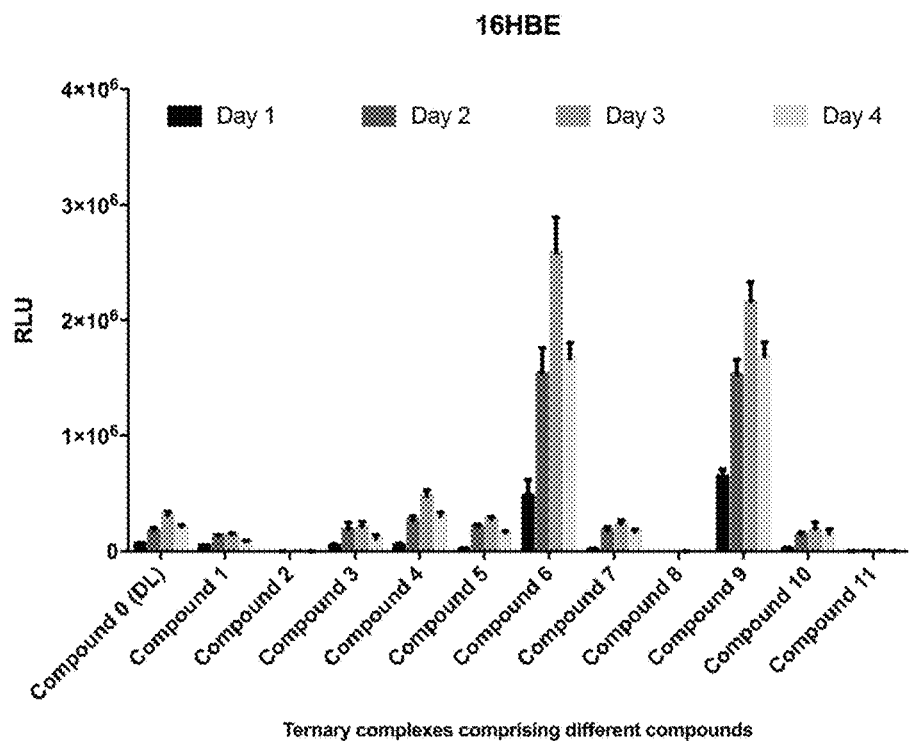

FIGS. 14a and 14b show comparisons of transfection efficiencies of different pDNA containing P704 based ternary complexes comprising different synthetic compositions according to the invention.

FIGS. 15a to 15k show comparisons of in vitro transfection efficiencies of IVT-mRNA containing P704 based ternary complexes comprising different synthetic compositions according to the invention in BEAS-2B cells.

FIGS. 16a to 16k show comparisons of in vitro transfection efficiencies of IVT-mRNA containing P704 based ternary complexes comprising different synthetic compositions according to the invention in 16HBE cells.

Figure 17A:
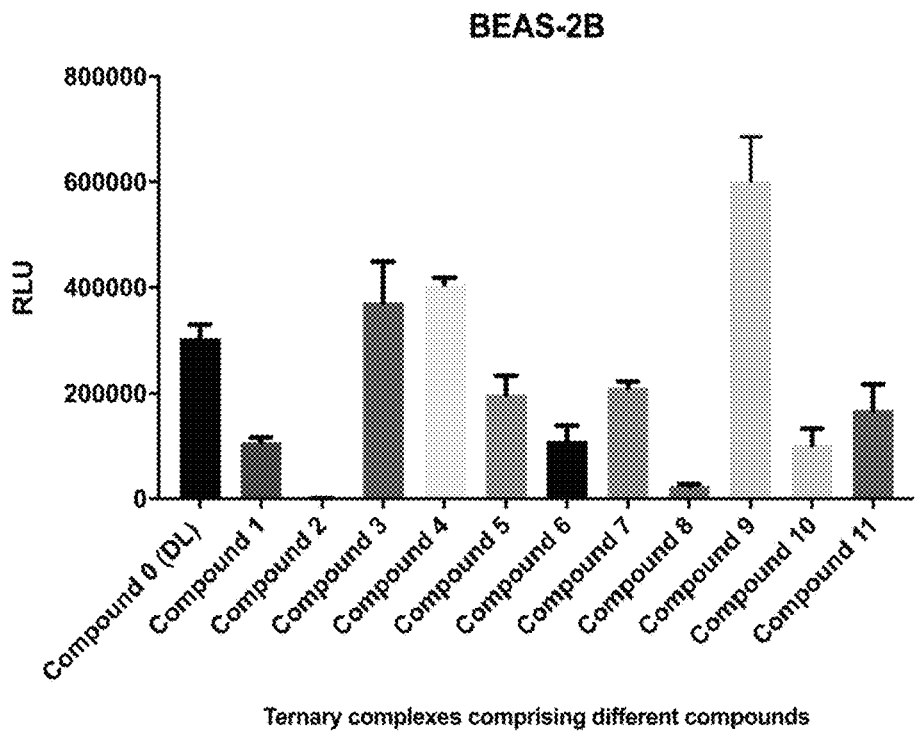
Figure 17B:
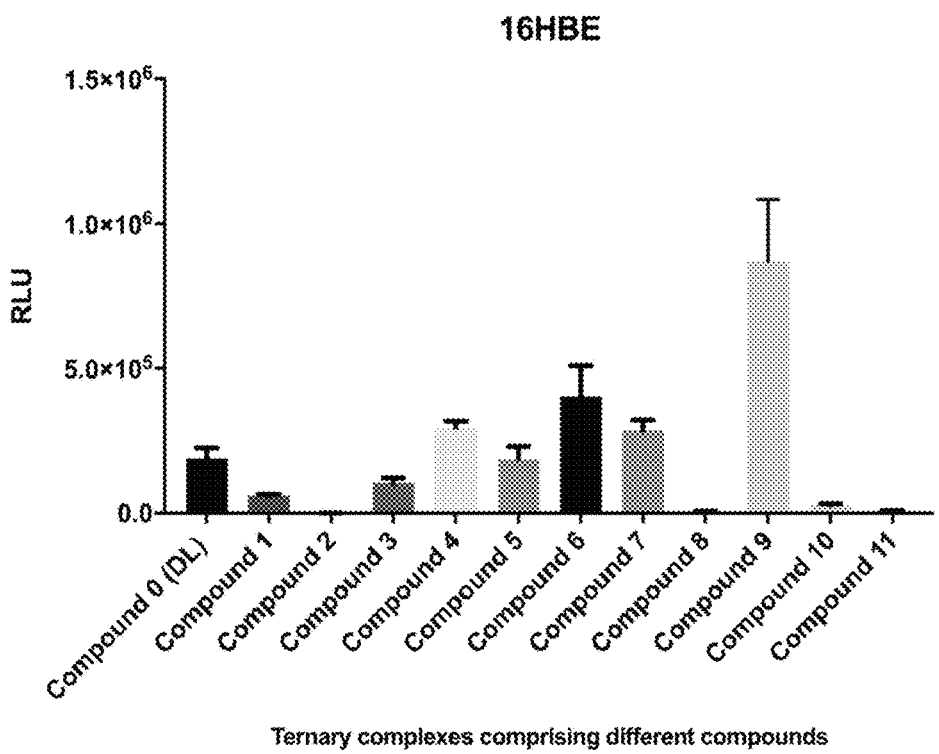
Figure 18A:
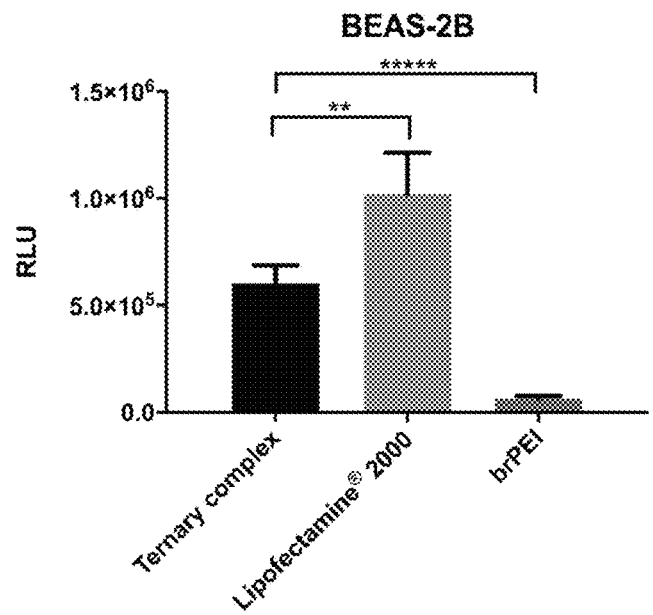
Figure 18B:
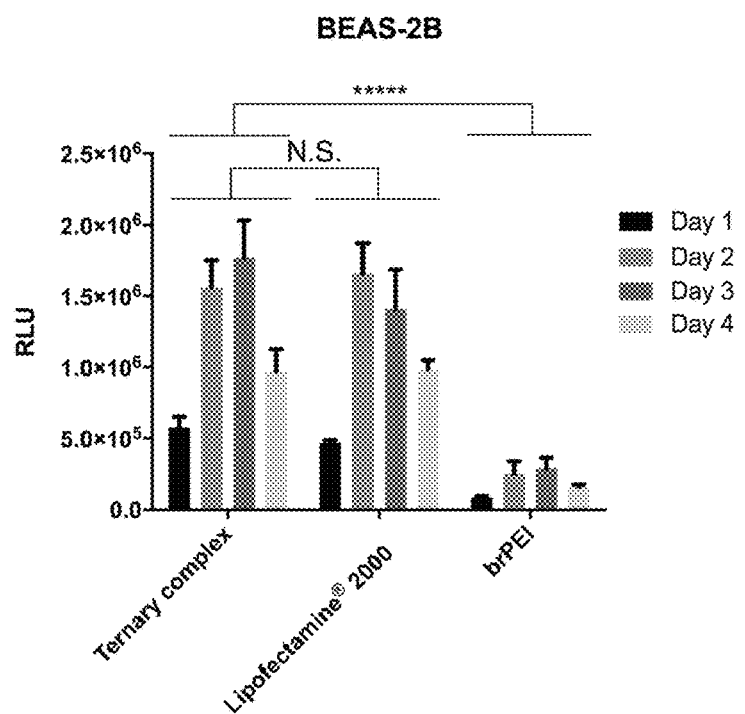
Figure 18C:
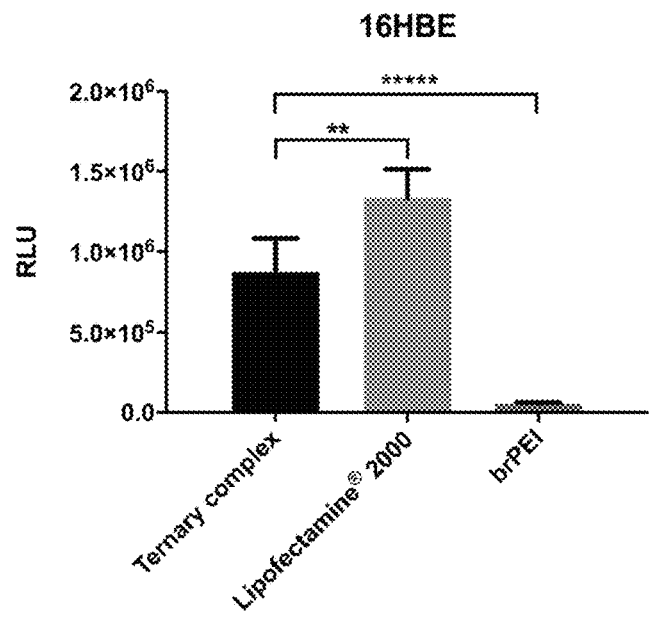
Figure 18D:
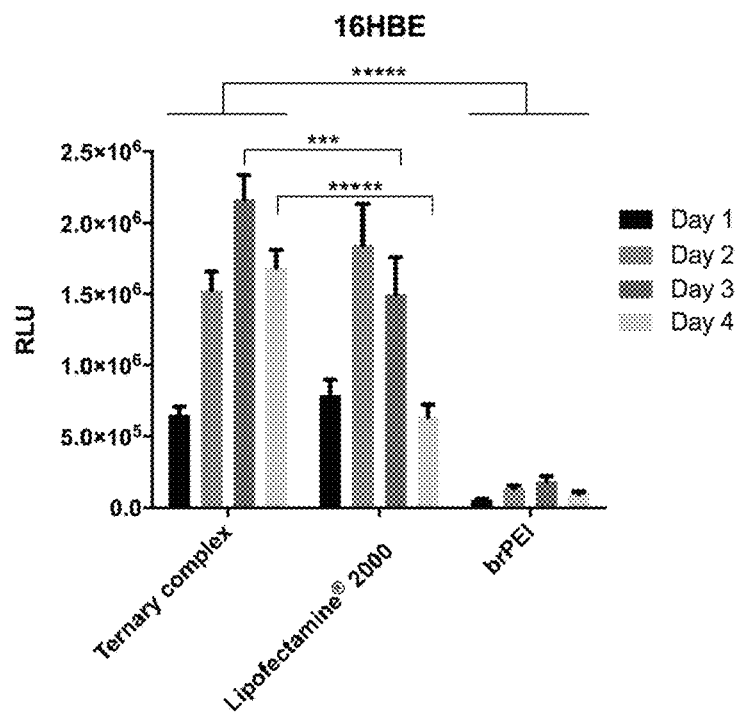

FIGS. 17a and 17b show comparisons of optimum transfection efficiencies of different IVT-mRNA containing ternary complexes comprising different synthetic compositions according to the invention.

FIGS. 18a to 18d show comparisons of in vitro transfection efficiencies of P704 based ternary complexes (P704+compound 9+IVT-mRNA or pDNA) with that of other non-viral vectors.

Figure 19A:
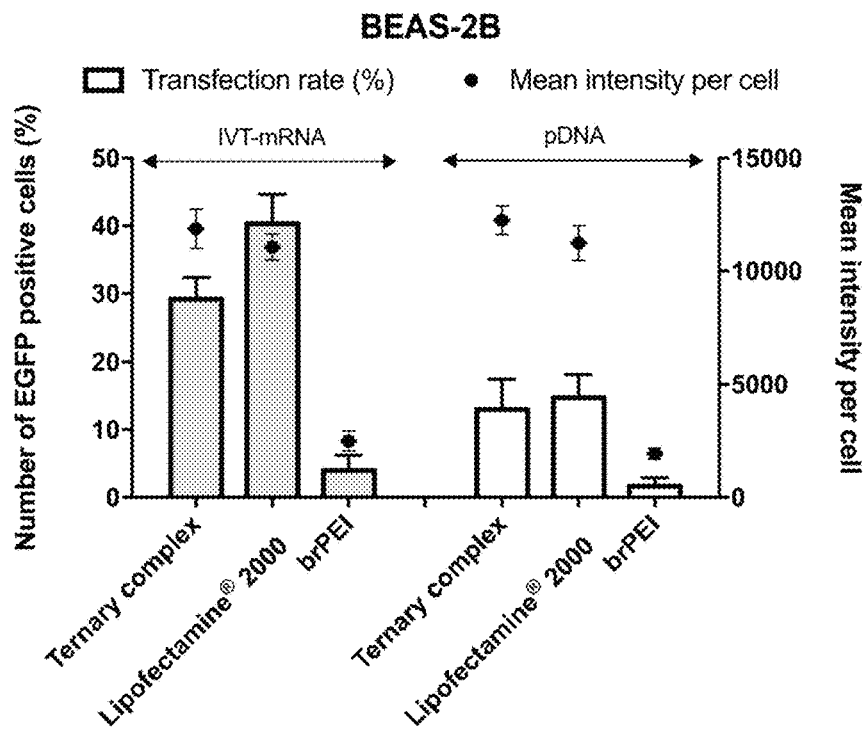
Figure 19B:
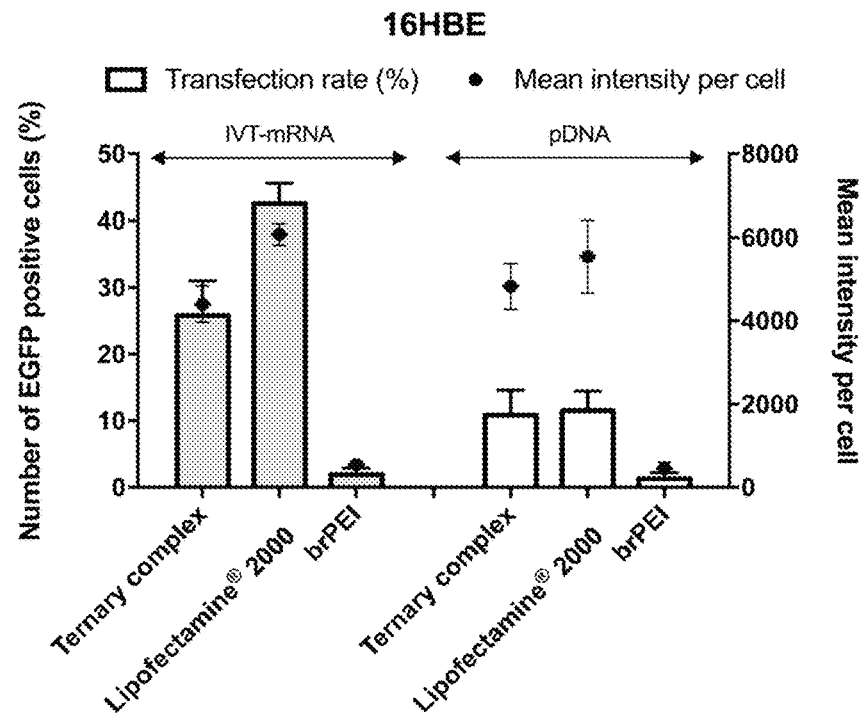
Figure 20A:
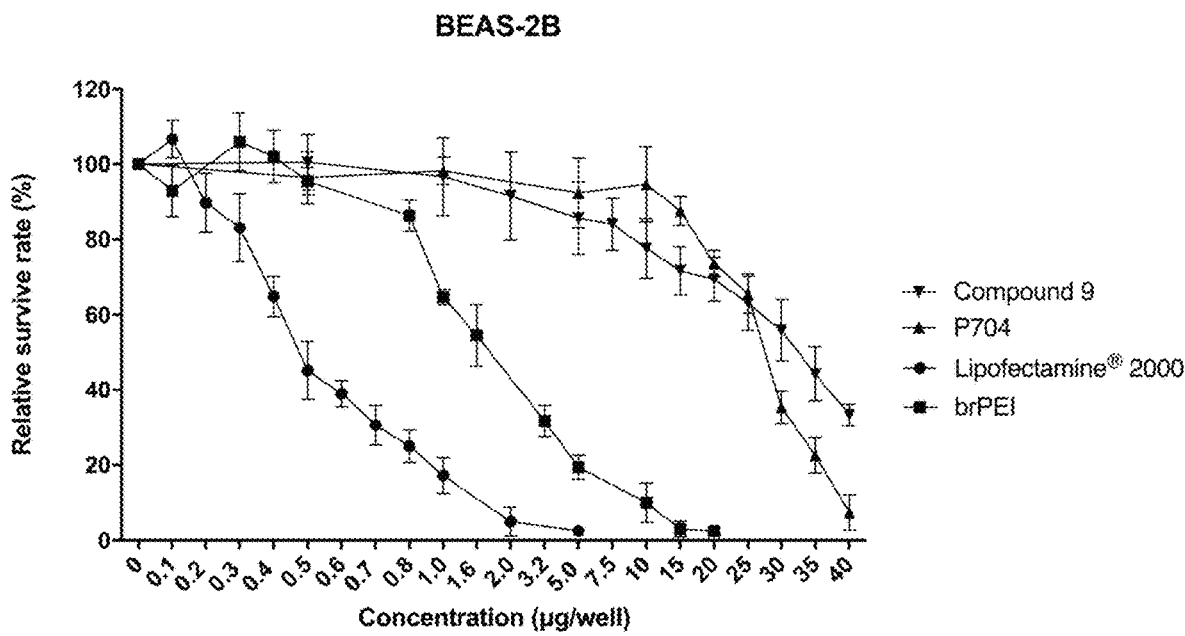
Figure 20B:
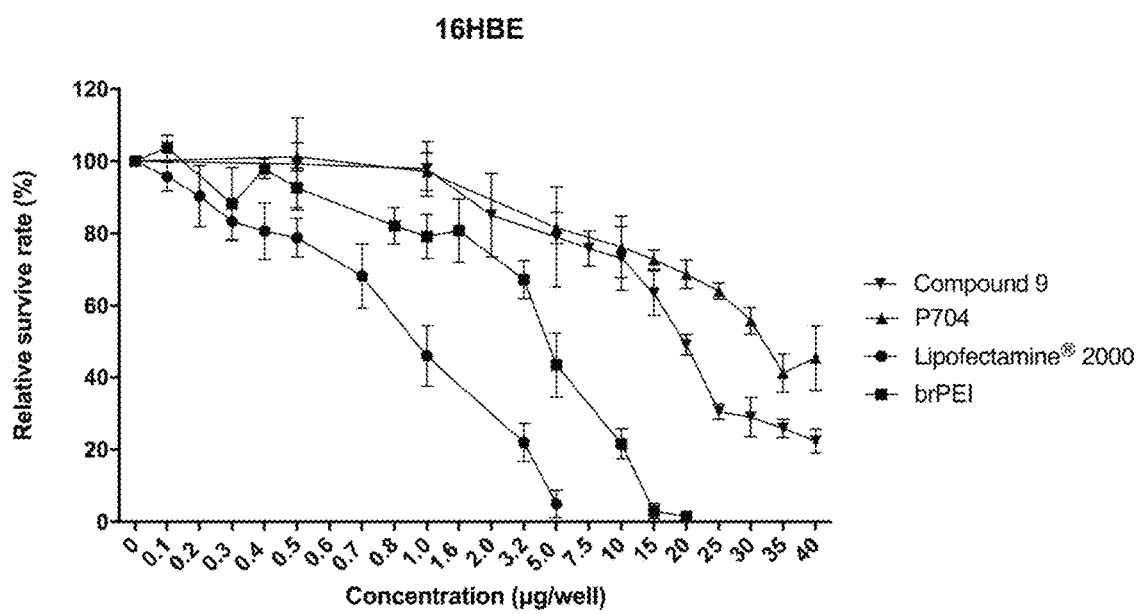
Figure 20C:
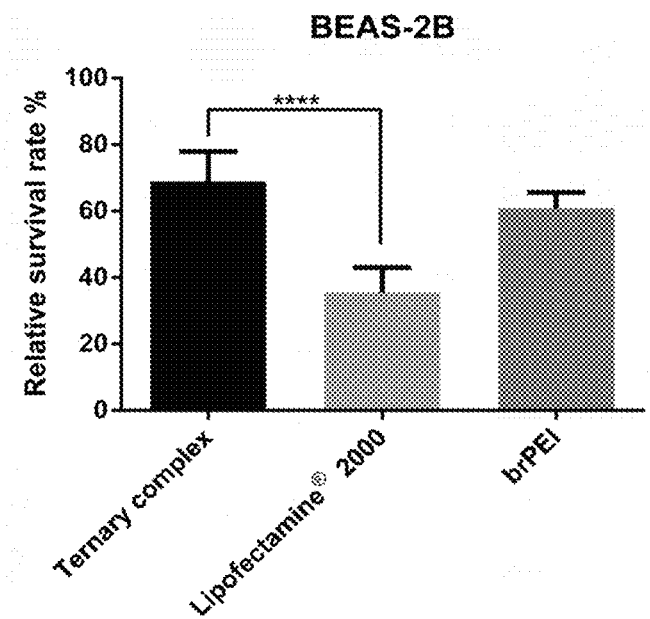
Figure 20D:
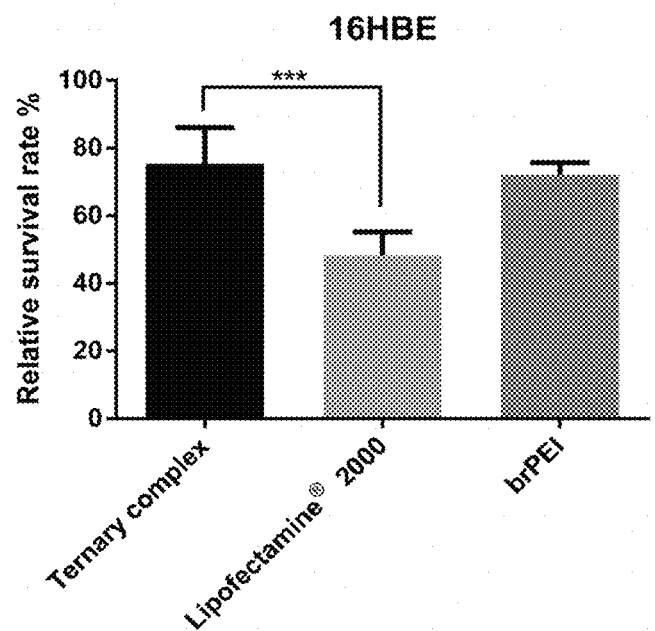

FIGS. 19a and 19b show transfection rates of EGFP mRNA or EGFP pDNA containing ternary complexes (P704+compound 9+nucleic acids) in BEAS-2B and 16HBE cells.

FIGS. 20a to 20d show comparisons of toxicities of P704, compound 9, Lipofectamine® 2000 and brPEI and their pDNA containing formulations.

Figure 21A:
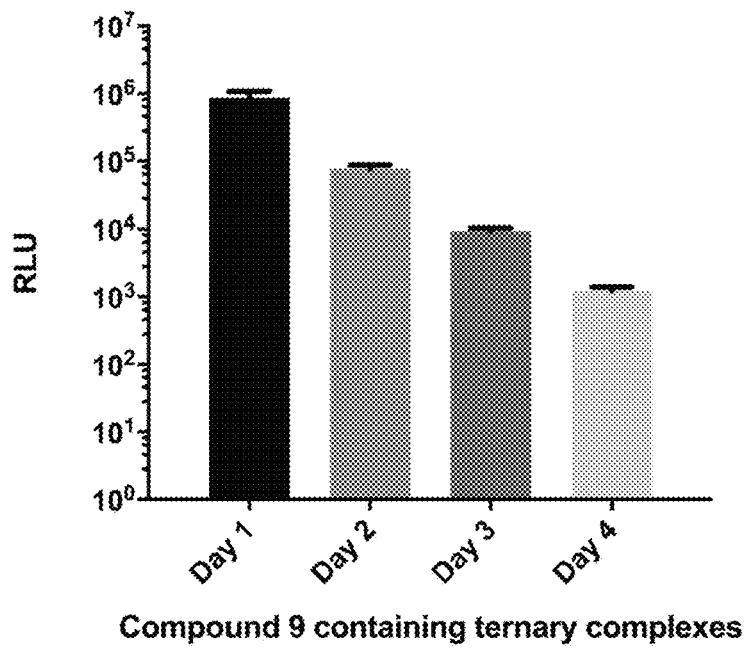
Figure 21B:
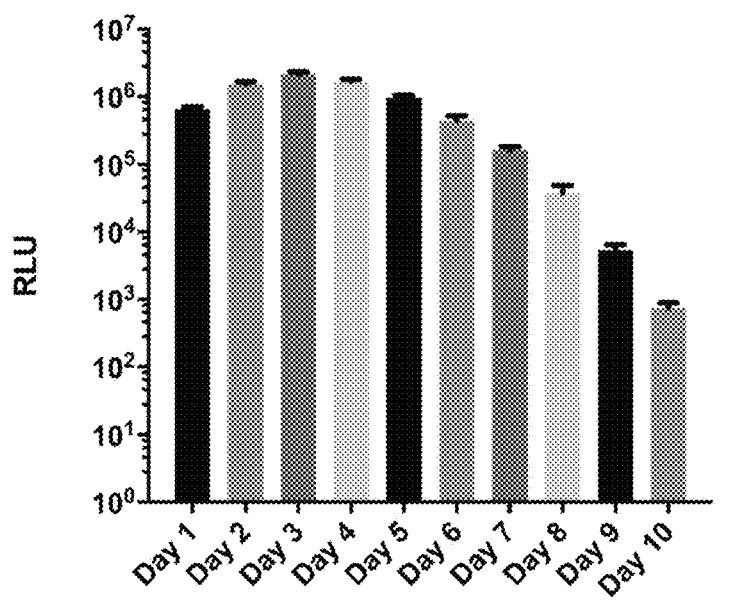

FIGS. 21a and 21b show expression kinetics of MetLuc mRNA or pDNA containing P704 based ternary complexes.

Figure 22A:
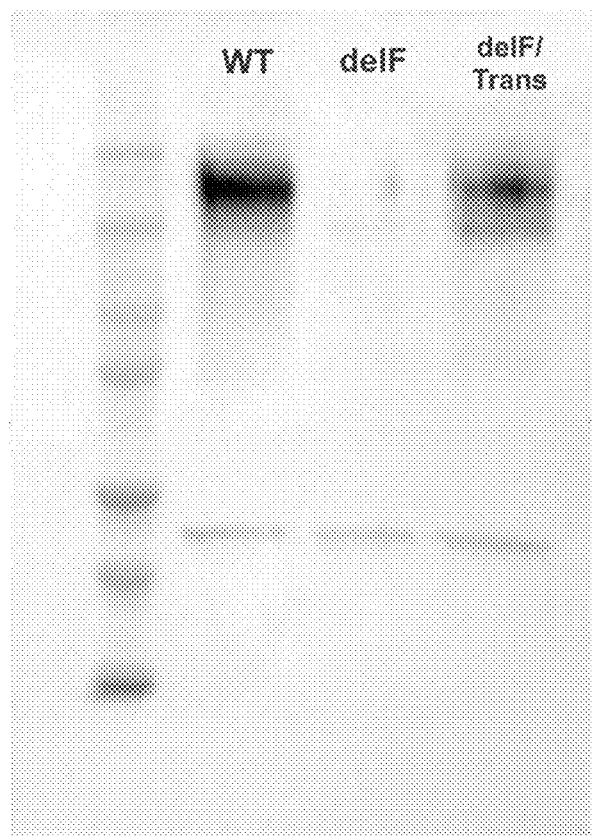
Figure 22B:
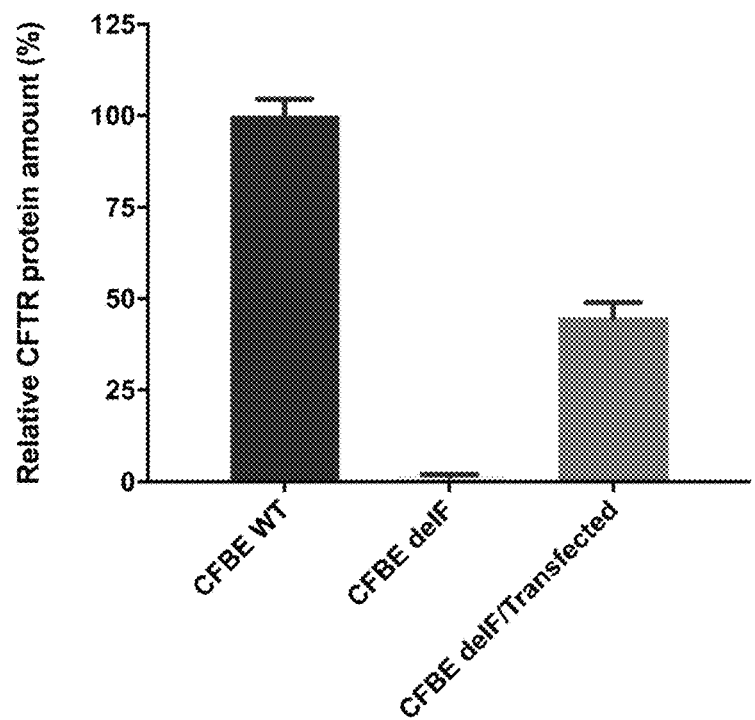
Figure 23A:
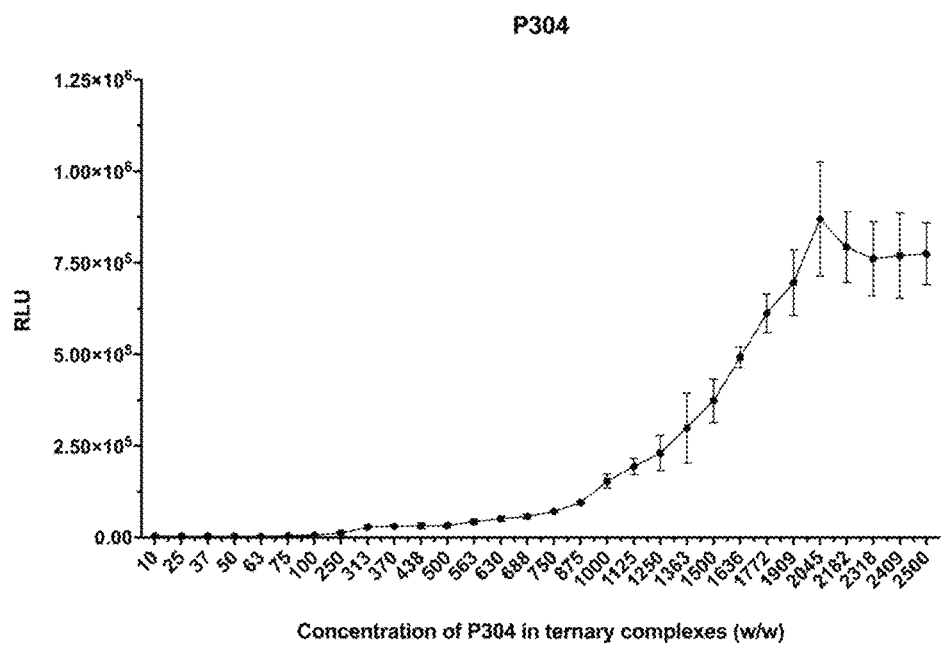
Figure 23B:
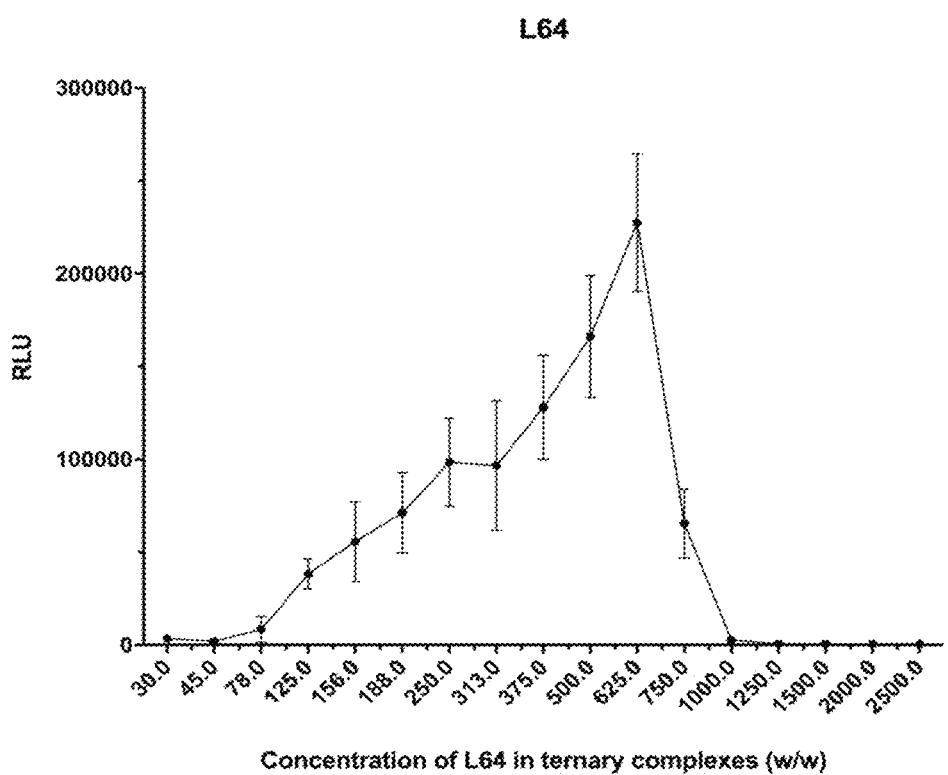
Figure 23C:
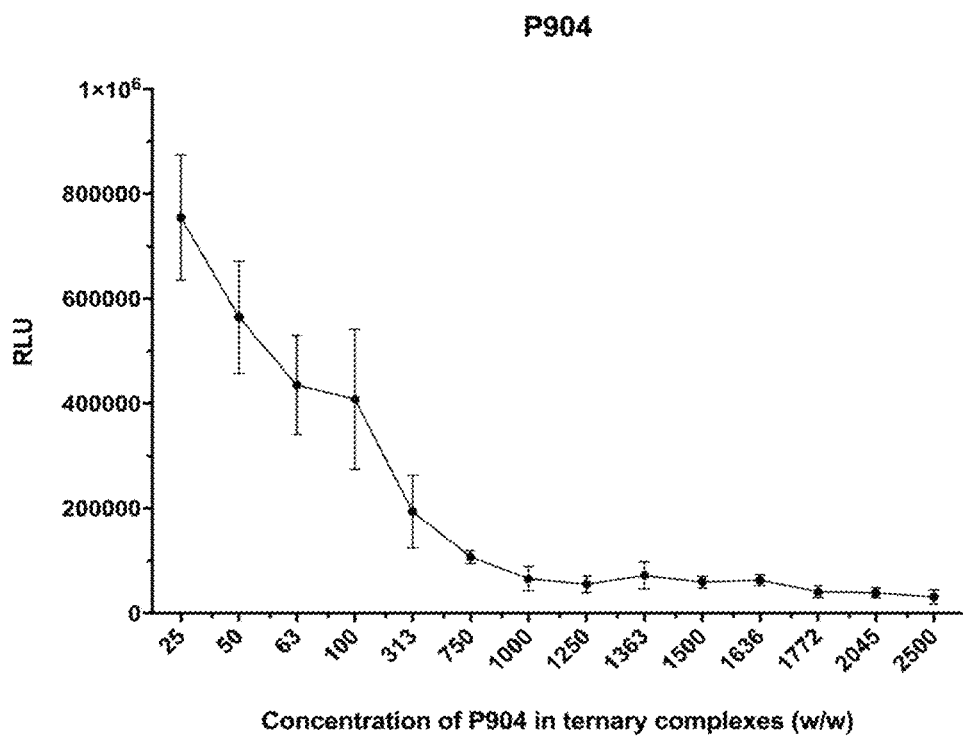
Figure 23D:
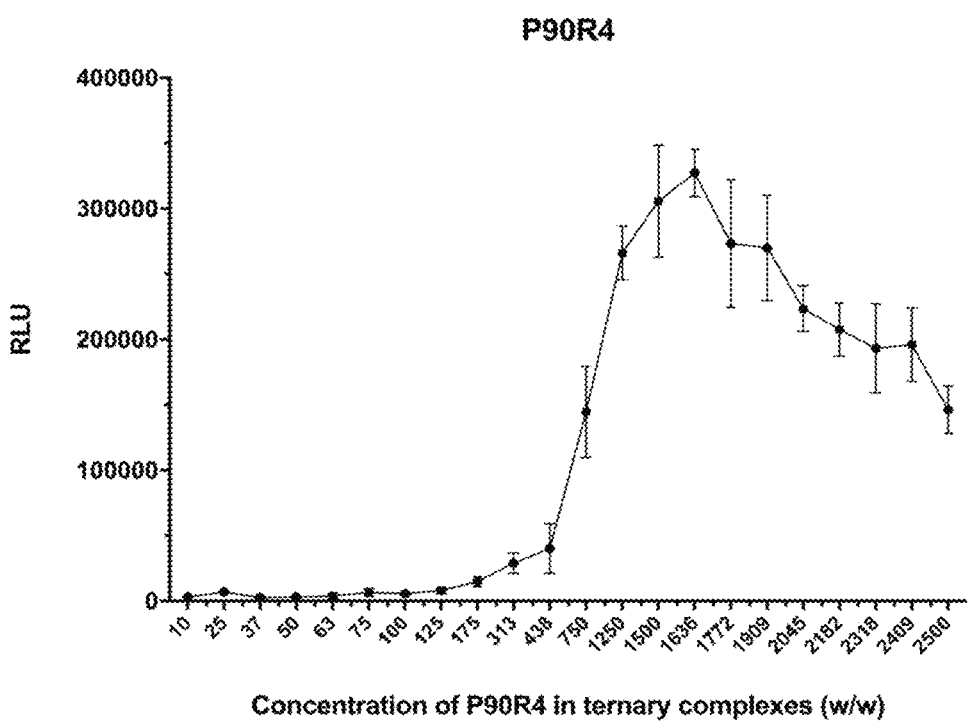

FIGS. 22a and 22b show the result of western blot analysis of membrane proteins of CFBE cells.

FIGS. 23a to 23d show comparisons of transfection efficiencies of MetLuc mRNA containing ternary complexes comprising other poloxamines or a poloxamer at different concentrations in 16HBE cells.

Figure 24A:
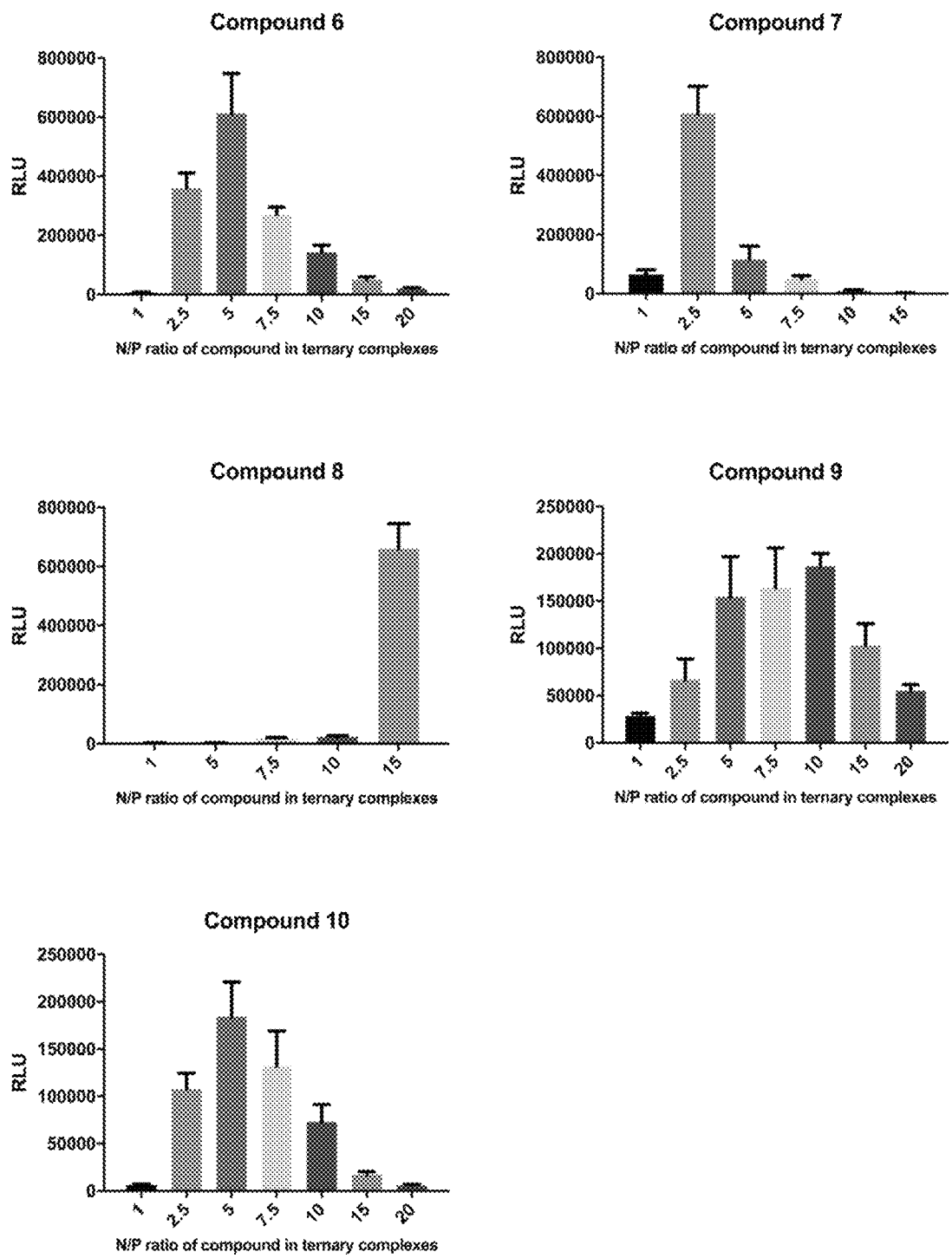
Figure 24B:
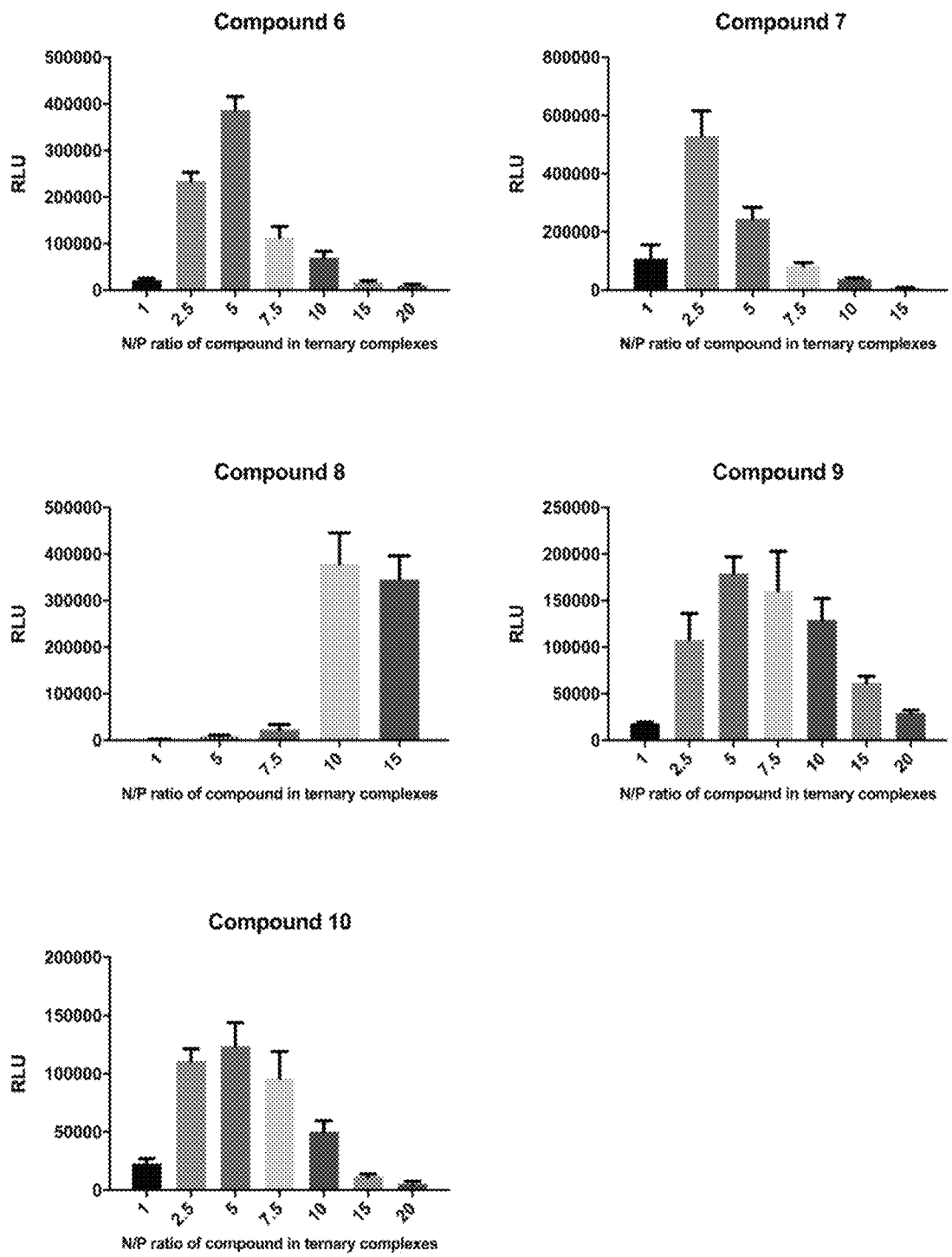

FIGS. 24a and 24b show comparisons of transfection efficiencies of MetLuc mRNA containing P304 or P90R4 based ternary complexes comprising different compounds in 16HBE cells.

Figure 25A:
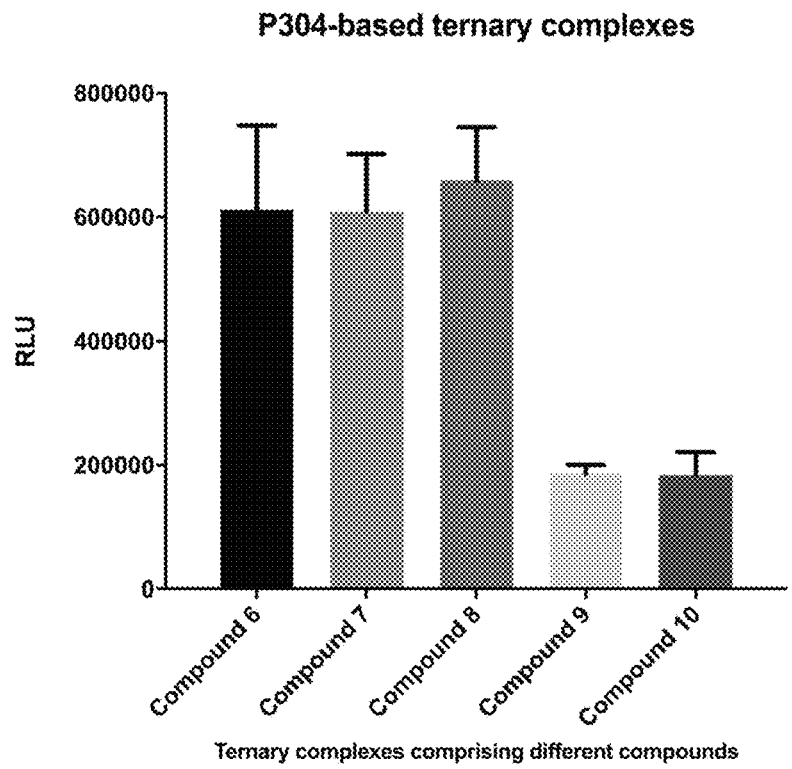
Figure 25B:
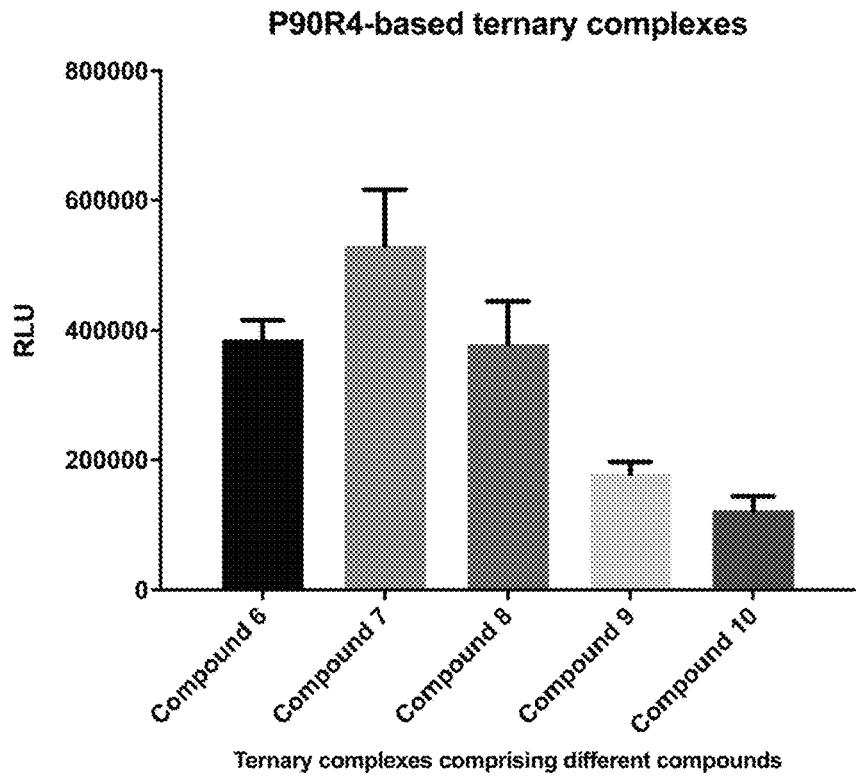

FIGS. 25a and 25b show comparisons of optimum transfection efficiencies of different MetLuc mRNA containing P304 or P90R4 based ternary complexes comprising different compounds in 16HBE cells.

Figure 26A:
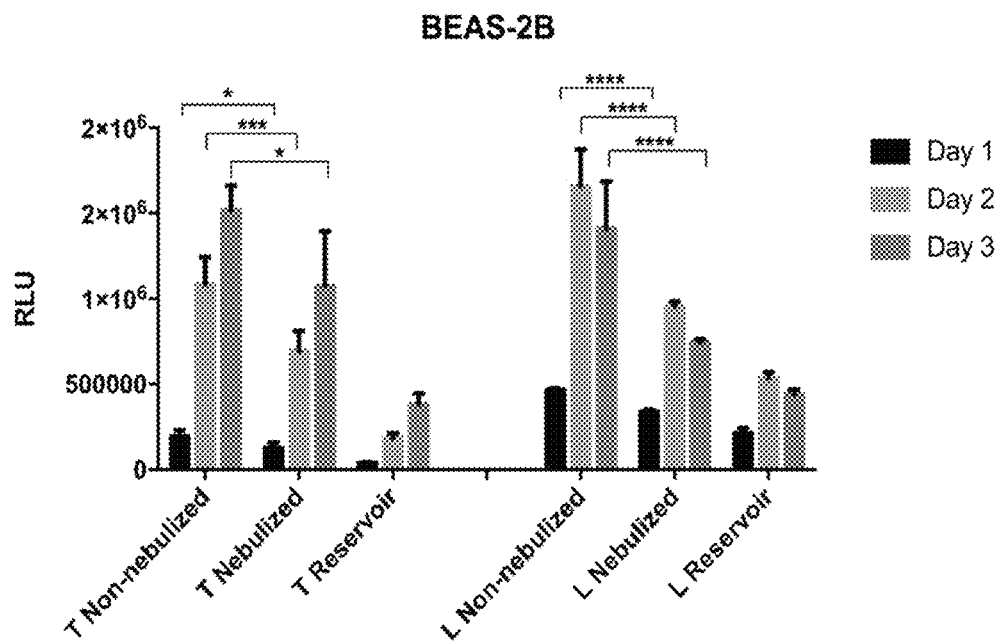
Figure 26B:
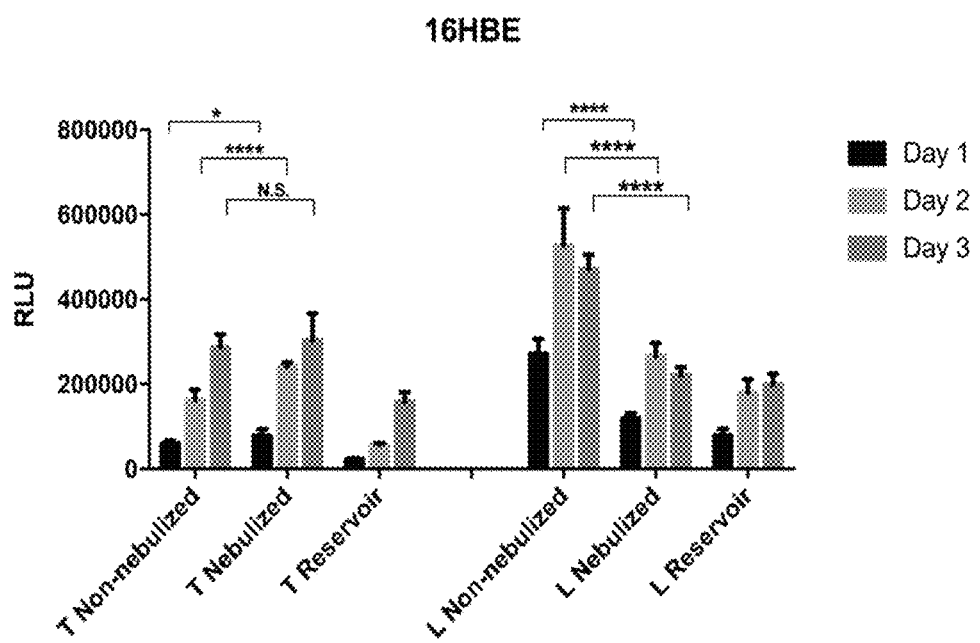

FIGS. 26a and 26b show transfection efficiencies of P704 based ternary complexes and Lipofectamine® 2000 based formulations before and after nebulization.

Figure 27:
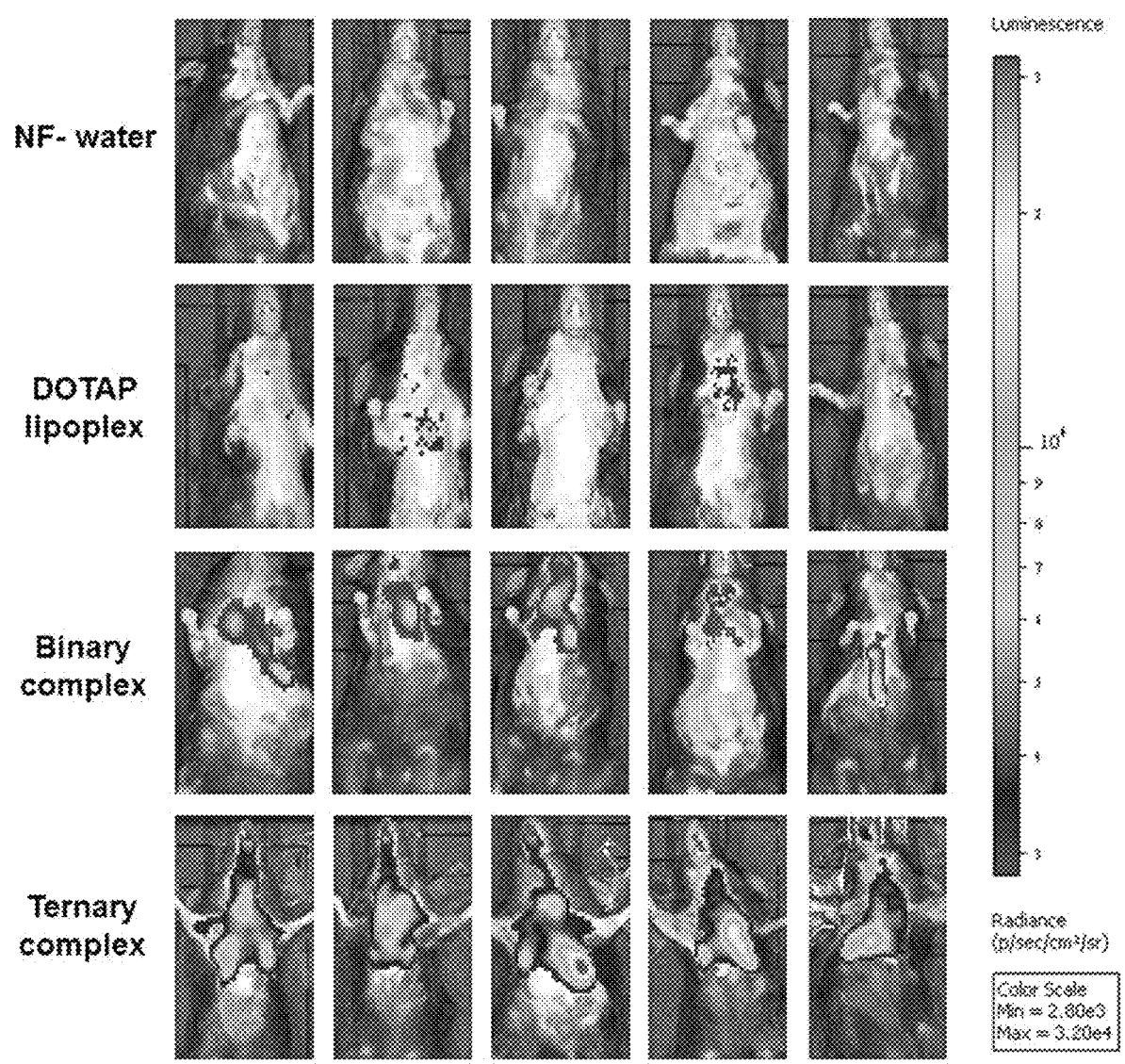

FIG. 27 shows the bioluminescence results of in vivo transfection assays in mice.

Figure 28A:
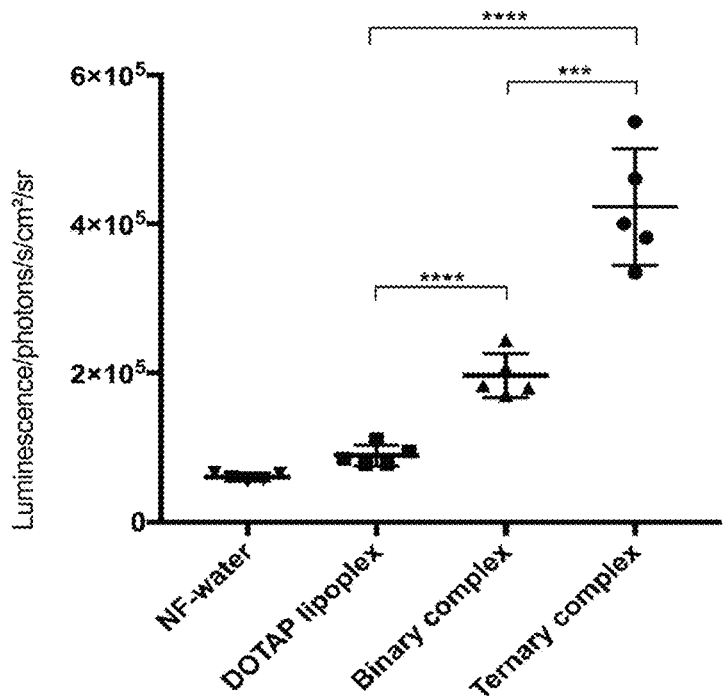
Figure 28B:
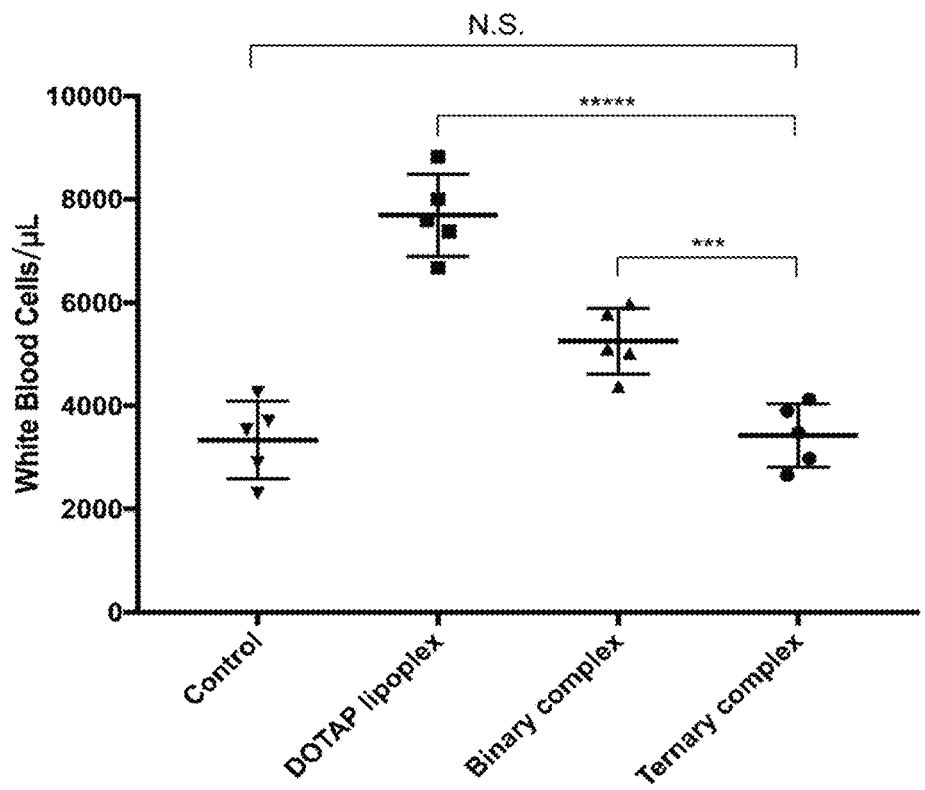

FIGS. 28a and 28b FIG. 28a shows the statistical analysis of the results of in vivo transfection assays according to FIG. 27. FIG. 28b shows the statistical analysis of white blood cells count from mice tested in FIG. 27.

MATERIALS AND METHODS

Reagents: Tetrafunctional block copolymers 704 (P704) were kindly provided by In-Cell-Art (Nantes, France). Poloxamine 304 (P304) and poloxamine 904 (P904) were kindly provided by BASF GmbH (Ludwigshafen, Germany). Poloxamine 90R4 and poloxamer 184 (L64) were purchased from Sigma-Aldrich Chemie GmbH (Munich, Germany). Lipofectamine® 2000 was purchased from Invitrogen (Schwerte, Germany). A mixture (molar ratio 1:1 in chloroform) of 1,2-dioleoyl-3-trimethylammoniumpropane (DOTAP) and 1,2-dioleoyl-sn-glycero-3-phosphoethanolamine (DOPE) was purchased from Avanti Polar Lipids (Alabaster, Ala., USA). LysoTracker® Red DND-99 and 4,6-diamidino-2-phenylindole (DAPI) were purchased from life technologies GmbH (Karlsruhe, Germany). Branched polyethyleneimine (brPEI, average MW=25 kDa), lipoic acid residue, myristic acid and cholesteryl chloroformate, 3-(4,5-Dimethyl-2-tetrazolyl)-2,5-diphenyl-2Htetrazolium bromide (MTT) were all purchased from Sigma-Aldrich (Munich, Germany). CFTR antibodies were obtained from Dr. John Riordan (University of North Carolina at Chapel Hill).

Nucleic acids: Stabilized, non-immunogenic messenger RNA (SNIM mRNA) encoding Metridia luciferase (MetLuc) as well as SNIM mRNA encoding enhanced green fluorescent protein (EGFP) were kindly provided by ethris GmbH (Planegg, Germany). Plasmid DNA encoding Metridia luciferase (MetLuc pDNA) was a generous gift from Prof. Dr. Christian Plank (Technical University of Munich, Germany). Plasmid DNA encoding both firefly luciferase and cyctic fibrosis regulator protein (fLUC-CFTR pDNA) and EGFP pDNA were purchased from Plasmid Factory (Bielefeld, Germany). Fluorescein labeled plasmid DNA (Fluo-pDNA) was obtained from Mirus (Goettingen, Germany).

Synthesis of peptide based compounds: All compounds were manually synthesized by Fmoc solid-phase peptide synthesis method. Briefly, 2-Chlorotrityl resin was used as the solid phase for the peptide synthesis. N,N-diisopropylethylamine (DIPEA) was used as the base and 2-(6-chloro-1H-benzotriazole-1-yl)-1,1,3,3-tetramethylaminium hexafluorophosphate (HCTU) was served as the coupling reagent. Lipoic acid, myristic acid or cholesterol was coupled to the —$NH_2$ end of the peptides before cleaving the peptides from the resin and deprotection. The peptides were then cleaved from the resin by acetic acid/trifluoroethanol/DCM (v/v/v, 10/20/70) at room temperature for 2 h. The resin was removed by filtration and the solvent was evaporated. After deprotection in cocktails (TFA/phenol/water/TIPS, 88:5:5:2) at room temperature for 2 h, the solution was concentrated and added into ice-cold diethyl ether for precipitation. The final products were purified by reverse phase HPLC. The molecular weight was confirmed by LC/MS.

Cell culture: BEAS-2B (human bronchial epithelia cell line) cells were obtained from the ATCC (American Type Culture Collection, Wesel, Germany) to culture in RPMI 1640 medium (Gibco, Germany) supplemented with 10% heat-inactivated fetal bovine serum (FBS, Gibco, Germany) and 1% (v/v) penicillin/streptomycin (Gibco, Germany). 16HBE (human bronchial epithelial cell line) cells were generously provided by Prof. Dr. Dieter C. Gruenert (University of California at San Francisco, Calif., USA) and were cultured in Eagle's Minimal Essential Medium (Gibco, Germany) with 10% heat-inactivated FBS (Gibco, Germany) and 1% (v/v) penicillin/streptomycin (Gibco, Germany) at 37° C. and 5% $CO_2$. CFBE-WT cells expressing wild type CFTR and CFBE-delF cells which contain the most common CF phenotype causing mutation (Phe508del) were obtained from Gregory Fleming James Cystic Fibrosis Research Center (University of Alabama at Birmingham) and were cultured in the same Eagle's Minimal Essential Medium as described above. All experiments were performed on cells in the logarithmic growth phase.

Preparation of IVT-mRNA/pDNA containing binary and ternary complexes: Stock solutions of P704 (5 mg/ml) and synthetic compound (1 mg/ml) were prepared in nuclease-free water (NF water) and stored at 4° C. P704 based binary complexes (P704/IVT-mRNA or P704/pDNA) were prepared by mixing equal volumes of diluted P704 stock solution with IVT-mRNA or pDNA solution at the desired concentration in 2× Tyrode's solution. Ternary complexes were generated via two-steps incubation. Briefly, P704 solutions at certain concentration (defined as weight/weight (w/w) ratio between P704 and nucleic acids) in NF-water were mixed with equal volume of synthetic compound solution at specific concentration (defined as N/P ratio, namely the w/w ratio between nitrogen residues in synthetic compound and nucleic acids phosphate groups). After 20 min incubation at room temperature (RT), same volumes of nucleic acid (IVT-mRNA or pDNA) solution in NF-water were added to the above P704/synthetic compound solution and mixed gently by pipetting up and down several times. Subsequently, complexes were incubated for another 20 min at RT prior to further use. IVT-mRNA or pDNA solutions in NF-water were complexed with brPEI (25 kDa) at an optimum N/P ratio, the resulting complexes were served as a control polyplex. As for control lipoplex, Lipofectamine® 2000 complexes were prepared according to the manufacturer's instructions using optimum concentration. In order to prepare DOTAP/DOPE liposomes, a lipid film was formed by removing the chloroform solvent in DOTAP/DOPE mixture solution under nitrogen atmosphere. The lipid film is hydrated with NF-water to make the final concentration 10 mM DOTAP/DOPE. The DOTAP/DOPE liposome formulation was formed by mixing 250 µl of pDNA encoding for firefly luciferase and cystic fibrosis transmembrane conductance regulator (fLUC-CFTR pDNA) (150 µg) containing solution and 250 µl diluted DOTAP/DOPE solution (190 µl of 10 mM DOTAP/DOPE liposome and 60 µl NF-water). The mix solution was incubated at RT for 20 min prior to further use.

Size and zeta potential measurements: Particle size and zeta potential measurements of P704 based binary and ternary complexes were measured using a Zetasizer Nano ZS (Malvern Instruments Ltd.) at 25° C. Binary complexes were prepared in Tyrode's solution at a weight/weight ratio (P704/IVT-mRNA or pDNA) of 63:1. Ternary complexes were prepared in NF-water with P704 at a weight/weight ratio of 63:1 and the compound at N/P ratio of 10:1 (compound 0 (DL) and compound 8) or 5:1 (compound 4 and compound 9) using methods described above. The IVT-mRNA and pDNA concentration in both binary and ternary complexes was fixed at 10 µg/ml.

Transmission electron microscopy: Transmission electron microscopy (TEM, FEI Tecnai G2 F20 STWIN) was used to observe morphology of both binary and ternary complexes. The complexes were freshly prepared in NF-water using methods described above and dropped onto Quantifoil holey carbon foil (Micro Tools GmbH, Germany) to obtain the images. The concentration of P704 and nucleic acids (IVT-mRNA or pDNA) were fixed at 0.25% (w/v) and 0.2 µg/µl in both binary and ternary complexes. Compound 9 at N/P ratio of 5 was applied in ternary complexes.

Agarose gel retardation assay: The extent of IVT-mRNA and pDNA condensation in binary and ternary complexes was investigated by electrophoresis on a 1% agarose gel containing 1 µg/ml ethidium bromide. Briefly, P704 at the concentration of 63 (w/w, relative to nucleic acids) and IVT-mRNA or pDNA in Tyrode's solution were used to prepare binary complexes. Compounds at varying N/P ratios (1 to 6) were used to form ternary complexes with P704 at the concentration of 63 (w/w) and IVT-mRNA or pDNA in NF-water. 200 ng IVT-mRNA or pDNA were added per well. To all samples, 3 µl of 6× loading buffer (0.25% w/v bromphenol blue, 0.25% xylene cyanol FF, 30% glycerol in water) was added before loading the samples onto the gel in Tris-acetate-EDTA (TAE) buffer at 120 V for 60 min.

In vitro transfection: For the luciferase assay, cells were seeded at a density of $1.8 \times 10^4$/well (BEAS-2B) or $3.5 \times 10^4$/well (16HBE) in 96-well plates 24 h before transfection to reach 60-80% confluence. Following removal of growth medium, cells were rinsed with DPBS (Gibco, Germany). 170 µl of fresh serum-free OptiMEM (Gibco, Germany) were added per well, and subsequently 30 µl of IVT-mRNA or pDNA containing complexes prepared, as described above, corresponding to 400 ng IVT-mRNA or pDNA per well, were added in replicates of five. After 4 h of incubation at 37° C. in a humidified 5% $CO_2$-containing atmosphere, the transfection medium was replaced with culture medium supplemented with 10% FBS and 1% (v/v) penicillin/streptomycin. Luciferase activity in 50 µl supernatants from transfected cells was assayed with Metridia luciferase substrate (coelenterazine, Invivogen, France) after 24 h using a FLUOstar microplate reader (BMG Labtech, Germany) and its activity is expressed in relative light units (RLU). In all cases each sample was measured on at least two other occasions to ensure the reproducibility of the data.

For enhanced green fluorescent protein (EGFP) expression, cells were seeded at a density of $6.8 \times 10^4$/well (BEAS-2B) or $7.0 \times 10^4$/well (16HBE) in 8-well slides (ibidi GmbH, Munich, Germany) 48 h before transfection to reach a monolayer (90-100% confluence). EGFP mRNA at the dose of 600 ng/well was used to prepare complexes for transfection. The transfection procedure was the same as described above. 24 h after transfection, cells were evaluated by means of fluorescence microscopy (Zeiss Axiovert 200 M, Carl Zeiss Microscopy GmbH, Germany).

Flow cytometry: To quantitatively determine the percentage of transfected cells expressing EGFP, EGFP mRNA or EGFP pDNA was complexed with P704 at the concentration of 63 (w/w) and compound 9 at the N/P ratio of 5 to form ternary complexes. Lipofectamine® 2000 at concentration of 6.7 µl/well and brPEI at N/P ratio of 20 were used as lipoplex and polyplex control. The amount of EGFP mRNA or EGFP pDNA in each sample was 4 µg/well. Then the complexes were incubated for 4 h with BEAS-2B cells ($6 \times 10^5$/well) or 16 HBE cells ($7.5 \times 10^5$/well) which were pre-seeded in 6-well plate 24 h before transfection. Cells were harvest 24 h (EGFP mRNA transfection) or 48 h (EGFP mRNA transfection) after transfection and suspended in a flow buffer (PBS with 2% FCS, 2 mM EDTA, 0.005% $NaN_3$; Sigma-Aldrich, Munich, Germany). Dead cells were excluded based on 7-AAD staining (eBioscience, Germany). 10 000 live cells per sample were analysed by flow cytometry (FACSCanto, BD Bioscience, Germany). Data were analysed with FCS Express 4 Flow Cytometry software (De Novo Software, USA).

In order to study the cellular uptake different binary and ternary complexes, 16 HBE cells ($7 \times 10^5$/well) were seeded in 6-well plate 24 h before investigation. P704 based binary complexes were prepared by mixing P704 at the concentration of 63 (w/w) with Fluo-pDNA in Tyrode's solution. Compound 9 based binary complexes were prepared by mixing compound 9 at the N/P ratio of 5 with Fluo-pDNA in NF-water. P704 based ternary complexes consisted of P704 at the concentration of 63 (w/w), compound 0 (DL) or compound 9 at optimum N/P ratio and Fluo-pDNA. P304 based ternary complexes consisted of P304 at the concentration of 2000 (w/w), compound 8 at N/P ratio of 20 and Fluo-pDNA. P90R4 based ternary complexes consisted of P90R4 at the concentration of 1600 (w/w), compound 8 at N/P ratio of 15 and Fluo-pDNA. The amount of Fluo-pDNA in each sample was 4 µg/well. Naked Fluo-pDNA was served as a negative control. After 4 h incubation, medium was removed. The cells were harvested and rinsed with cold PBS for three times followed immediately by flow cytometry analysis. The amount of 10 000 live cells was collected for each sample.

With the purpose of identifying possible internalization mechanisms of ternary complexes by human bronchial epithelium cells, 16 HBE cells were pre-incubated at different temperatures or treated with specific agents at 37° C. for 1 h, then incubated with P704 based ternary complexes in the same conditions as described above. (I, II) To examine the effects of chlorpromazine and filipin, which were the clathrin- and caveolae-dependent endocytosis inhibitors, 10 µg/ml chlorpromazine or 1 µg/ml filipin in OptiMEM were used. (III) To study the effect of amiloride (macropinocytosis inhibitor), 0.3 mg/ml amiloride was adopted. (IV) To investigate the effect of protamine, an adsorptive-mediated endocytosis inhibitor, 1 mM protamine sulfate was added. (V) To examine the effect of desulfurization, cells were pre-incubated with 35 mM sodium chlorate in cell culture medium for 24 h (VI) To test the effect of sodium azide, an active transport inhibitor, sodium azide dissolved in OptiMEM at the concentration of 1 mg/ml was incubated with cells. (VII) To investigate the effect of temperature on cellular uptake, the experiment was performed at 4° C. (VIII) Excess amount of free compound 9 (0.01 µg/µl), KWET peptide (hydrophobic fragment of compound 9), or targeting ligand from compound 9 at the same amount compare to compound 9, were used as receptor mediated endocytosis competitor for compound 9. (IX) Excess amount of free compound 0 (DL) (0.01 μg/μl), K4R4 peptide (cationic fragment of compound 0 (DL)), lipoic acid or nuclear localization signal (NLS) at the same amount compare to compound 0 (DL), were used as potential receptor mediated endocytosis competitor for compound 0 (DL). In addition, incubation of ternary complexes without any treatment was used as positive control. The results are shown as relative uptake rate of different groups which normalized according to positive control group.

Cytotoxicity assay: The effect of P704, compound 9, Lipofectamine® 2000 and brPEI (25 kDa) at different concentration against cell viability of BEAS-2B and 16HBE cells was evaluated using a MTT assay known in the art. Meanwhile, the cytotoxicity of P704/compound 9/IVT-mRNA ternary complex in optimum composition against BEAS-2B and 16HBE cells were investigated and compared with that of Lipofectamine® 2000 based lipoplexes and brPEI based polyplexes in optimum composition using the same assay, 24 h after the transfection. Cell viability was calculated as a relative value (in %) compared to the control, untransfected cells.

Western Blot: The amount of CFTR protein within wild-type CFBE cells (CFBE-WT) which functionally expressing CFTR, CFTR deficient cells (CFBE-delF) and CFTR-pDNA containing ternary complexes transfected CFBE-delF cells were evaluated by Western Blot analysis. For transfected CFBE-delF cells, P704/compound 9/CFTR-pDNA ternary complexes were incubated with pre-seeded CFBE-delF cells (350,000 cells/well in 6-well plate) for 4 h at 37° C. in a humidified 5% $CO_2$-containing atmosphere. 48 h after transfection, cells were trypsinized and, after centrifugation (400 g for 5 min), pellets were resuspended in 100 μl of lysis buffer (RIPA lysis buffer, Millipore) and 1% protease inhibitor cocktail (Roche) and placed on ice for 15 min. The extracts were centrifuged at 20000 g for 10 min at 4° C. to remove nonsoluble material. The concentration of the proteins in the supernatant was measured photometrically using the Bradford test (BioRad). For the detection of CFTR protein, 25 μg of total protein was separated via sodium dodecylsulfate polyacrylamide gel electrophoresis (SDS-PAGE) (7.5% acryl amide). A tank blot apparatus (Mini Trans-Blot® Electrophoretic Transfer Cell; Bio-Rad, Munich, Germany) was used to transfer proteins to a polyvinylidene fluoride membrane (PVDF, Amersham) at 120 V for 70 min. Nonspecific binding sites were blocked for 1 h at room temperature with 5% nonfat dry milk in Trisbuffered saline/Tween (TBST, BioRad, 0.1% TWEEN20, Applichem). The CFTR was detected with a CFTR primary antibody ("217", The University of North Carolina, USA), with a concentration of 1:5000 diluted in 5% nonfat dry milk/TBST at RT for 1 h. After washing in TBST, the membrane was incubated at RT for another 1 h with the affinity donkey polyclonal anti-mouse immunoglobulin (Ig) G-H&L HRP (Abcam, ab6820) diluted 1:10 000 in 5% nonfat dry milk/TBST. After washing the membrane in TBST again, detection was carried out with Chemiluminescence (ChemiDoc, BioRad). For control experiments, we prepared whole cell protein extracts from nontransfected CFBE-delF and CFBE-WT cells. To assure comparable protein amount and expression, we use 3-actin (C4 HRP, sc-47778, Santa Cruz Biotechnology, USA) for normalization of the Western blot data. We used ImageJ (Wayne Rasband, National Institutes of Health, Bethesda, USA) for densitometric evaluation of the intensity of the CFTR bands.

Animal studies: All in vivo studies were performed according to German animal welfare law and were authorized by the local animal welfare authorities (Hannover Medical School animal care and use committee). Twenty-week-old B6cf mice were kept under specific pathogen-free conditions undergoing a 12 h/12 h light/dark cycle with free access to food and water. Animals were conceded an adaption time of at least 7 days prior to begin of experiments.

Statistical analysis: Statistical analysis was performed using Prism 7 (GraphPad software Inc, USA). Dual comparisons were made using the Student's t-test and comparisons between multiple conditions were analysed using ANOVA. Significant differences were defined as *: $p<0.05$; : $p<0.01$; *: $p<0.005$; **: $p<0.001$; ***: $p<0.0001$.

The following synthetic compositions were synthesized:

1. Compound 0 (DL):
$NH_2$-VKRKKKPKKRRRRKKWK(DL-lipoic acid)-$CONH_2$
(peptide sequence of this compound: SEQ ID NO: 1), 2. compound 0 (R):
$NH_2$-VKRKKKPKKRRRRKKWK(R-lipoic acid)-$CONH_2$
(peptide sequence of this compound: SEQ ID NO: 1), 3. compound 1:
$NH_2$-VKRKKKPKKRRRRKK-$CONH_2$
(peptide sequence: SEQ ID NO: 2), 4. comound 2:
DL-lipoic acid, 5. compound 3:
$NH_2$-VKRKTKPKKRRRRKKWK(DL-lipoic acid)-$CONH_2$
(peptide sequence of this compound: SEQ ID NO: 3), 6. compound 4:
DL-lipoic acid-WKKKKRRRRRKKKK-GACSERSMNFCG
(peptide sequence of this compound: SEQ ID NO: 4), 7. compound 5:
DL-lipoic acid-WKKKKRRRRRKKKK-GACYGLPHKFCG
(peptide sequence of this compound: SEQ ID NO: 5), 8. compound 6:
DL-lipoic acid-WKRRRRRRRRRKK-GACSERSMNFCG
(peptide sequence of this compound:
SEQ ID NO: 10), 9. compound 7:
(peptide sequence of this compound: SEQ ID NO: 6)
DL-lipoic acid-WKKRRRRRRRRKK-GACYGLPHKFCG, 10. compound 8:
DL-lipoic acid-WLHHHKKLLHHHKKL-GACSERSMNFCG
(peptide sequence of this compound: SEQ ID NO: 7), 11. compound 9:
KETWWETWWTEWWTEW-KKKKRRRRRKKKK-GACSERSMNFCG
(peptide sequence: SEQ ID NO: 8), 12. compound 10:
$C_{13}H_{27}$CONH-KKKKRRRRRKKKK-GACSERSMNFCG
(peptide sequence of this compound: SEQ ID NO: 9),
and 13. compound 11:
Cholesteryl-KKKKRRRRRKKKK-GACSERSMNFCG
(peptide sequence of this compound: SEQ ID NO: 9).

Sequences given in italics are targeting sequences. Underlined sequences represent hydrophobic moieties. Sequences given in bold represent cationic moieties, i. e. the nucleic acid binding sequences.

In compounds 0 and 3 the hydrophobic moiety in form of the lipoic acid residue is in each case covalently bound to the peptide residue via the side chain of the C-terminal lysine moiety. In compounds 4, 5, 6, 7, 8, 10 and 11 the hydrophobic moiety in form of the lipoic acid residue, the $C_{13}H_{27}CONH$-residue and the cholesteryl is in each case covalently bound to the N-terminus of the peptide residues according to SEQ ID NO: 4, SEQ ID NO: 5, SEQ ID NO: 6, SEQ ID NO: 7, SEQ ID NO: 9, and SEQ ID NO: 10.

The only difference between compound 0 (DL) and compound 0 (R) is that the lipoic acid residue is DL-lipoic acid residue in case of compound 0 (DL) and R-lipoic acid residue in case of compound 0 (R). DL-lipoic acid residue and R-lipoic acid residue are enantiomers. Transfection efficiencies of ternary complexes formed by P704, a nucleic acid and compound 0 (DL) or compound 0 (R) are similar. All experiments in which "compound 0" was used were performed by use of compound 0 (DL). When not further specified "compound 0" always means "compound 0 (DL)".

For proving those moieties which constitute pivotal roles in boosting transfection efficiency of ternary complex, three compound controls were used and their activities in transfecting airway epithelium cells were compared with compound 0 containing ternary complex. Compound 1, compound 2 and compound 3 are control compounds of compound 0. Compound 1 contains a functional NLS targeting sequence and nucleic acid binding sequence but has no hydrophobic moiety to bind the amphiphilic block copolymer. Compound 2 is a cationic moiety negative control of compound 0 (NLS sequence was simultaneously eliminated from compound 2, as there are also many positively charged amino acids within). Compound 3 shares the same hydrophobic moiety and cationic moiety with compound 0 but contains a mutated NLS targeting sequence in which the lysine at position 5 has been replaced by threonine. This mutation is known to be nuclear transport deficient. Compounds 0 and 1 are compounds containing a functional NLS targeting sequence. In compounds 4 to 11 the targeting sequence has in each case high affinity to human airway epithelium cells. The amino acids "GAC . . . FCG" provide conformational stability for the sequence having high affinity to human airway epithelium cells.

Compounds 5 and 7 have the same sequence having high affinity to human airway epithelium cells but differ in the nucleic acids binding section. Nucleic acid binding section of compound 5 has eight lysine and five arginine residues whereas the corresponding section of compound 7 contains four lysine and eight arginine residues.

In Vitro Experiments:

In vitro transfection profiles of binary complexes (P704+IVT-mRNA or pDNA) in cultured human bronchial cells (BEAS-2B and 16HBE cells):

400 ng/well MetLuc mRNA was complexed with P704 at different concentrations from 2.5 to 200 (w/w, relative to nucleic acids) in Tyrode's solution. After 30 min incubation at room temperature (RT), samples were added to 96-well plate containing pre-seeded cells and incubated with cells in opti-MEM (without serum and antibiotics) for 4 h at 37° C. in a humidified atmosphere (95% air, 5% $CO_2$). Luciferase activity in 50 μl supernatants from transfected BEAS-2B cells (FIG. 2*a*) or 16HBE cells (FIG. 2*b*) was assayed after 24 h and its activity is expressed in relative light units (RLU). MetLuc pDNA/P704 binary complexes were prepared in the same way of MetLuc mRNA counterpart, luciferase activity in transfected BEAS-2B cells (FIG. 2*c*) or 16HBE cells (FIG. 2*d*) was measured 24 h, 48 h, 72 h and 96 h after transfection and its activity is expressed in relative light units (RLU). The data are given as the mean±standard deviation (SD) of the mean (n>5).

In vitro transfection profiles of binary complexes (compound 0 (DL)+IVT-mRNA or pDNA) in cultured human bronchial cells (BEAS-2B and 16HBE cells):

400 ng/well MetLuc mRNA was complexed with compound 0 (DL) at different N/P ratios from 5 to 30 (relative to nucleic acids) in nuclease-free water. After 30 min incubation at room temperature (RT), samples were added into 96-well plate containing pre-seeded cells and incubated with cells in opti-MEM (without serum and antibiotics) for 4 h at 37° C. in a humidified atmosphere (95% air, 5% $CO_2$). Luciferase activity in 50 μl supernatants from transfected BEAS-2B cells (FIG. 3*a*) or 16HBE cells (FIG. 3*b*) was assayed after 24 h and its activity is expressed in relative light units (RLU). MetLuc pDNA/compound 0 (DL) binary complexes were prepared in the same way of IVT-mRNA counterpart, luciferase activity in transfected BEAS-2B cells (FIG. 3*c*) or 16HBE cells (FIG. 3*d*) was measured 24 h, 48 h, 72 h and 96 h after transfection and its activity is expressed in RLU. The data are given as the mean±standard deviation (SD) of the mean (n>5).

In vitro transfection profile of binary complexes (compound 9+pDNA) in cultured human bronchial cells:

400 ng/well MetLuc pDNA was complexed with compound 9 at different N/P ratios from 5 to 20 (relative to nucleic acids) in nuclease-free water. After 30 min incubation at room temperature (RT), samples were added into 96-well plate containing pre-seeded cells and incubated with cells in opti-MEM (without serum and antibiotics) for 4 h at 37° C. in a humidified atmosphere (95% air, 5% $CO_2$). Luciferase activity in 50 μl supernatants from transfected in transfected BEAS-2B cells (FIG. 4*a*) or 16HBE cells (FIG. 4*b*) was measured 24 h, 48 h, 72 h and 96 h after transfection and its activity is expressed in RLU. The data are given as the mean±standard deviation (SD) of the mean (n>5).

Agarose gel electrophoresis of IVT-mRNA and pDNA containing P704 based ternary complexes:

FIGS. 5*a*, 5*b* and 5*f* show the results of IVT-mRNA condensation studies using P704 based ternary complexes comprising different compounds at a N/P ratio range of 1-6. Binary complexes consisting of IVT-mRNA and P704 at the same concentration were used as binary control. Uncomplexed IVT-mRNA was used as a positive control (+) and NF-water as negative control (−).

FIGS. 5*c*, 5*d* and 5*e* show the results of pDNA condensation studies using P704 based ternary complexes comprising different compounds at a N/P ratio range of 1-6. Binary complexes consisting of pDNA and P704 at the same concentration were used as binary control. Uncomplexed pDNA was used as a positive control (+) and NF-water as negative control (−).

FIG. 5*g* shows the result of an experiment concerning the stability of pDNA containing P704 based binary and ternary complexes containing compound 9 in presence of increasing DNase I activity (2.5 U to 10 U). 1 kb DNA standard was used a reference (1 kb), naked pDNA was used as a positive control (DNA+0 U DNase I) and DNA+2.5 U DNase I was used as negative control.

TEM micrographs of P704 based binary complexes and ternary complexes: FIG. 6*a* is a TEM micrograph of binary complexes prepared by mixing equal volume of P704 with IVT-mRNA in Tyrode's solution. Noncomplexed IVT-mRNA was marked with arrow. FIG. 6*b* is a TEM micrograph of binary complexes prepared by mixing equal volume of P704 with pDNA in Tyrode's solution. FIG. 6*c* is a TEM micrograph of ternary complexes consisting of IVT-mRNA, P704 and compound 9 in NF-water. FIG. 6*d* is a TEM micrograph of ternary complexes consisting of pDNA, P704 and compound 9. The nucleic acids in all complexes were fixed at the concentration of 0.2 µg/µl. The concentration of P704 in both binary and ternary complexes was kept at 0.25%.

The results of physical characterizations (size and zeta potential) of P704 based binary and ternary complexes containing IVT-mRNA or pDNA are given in the following table:

| Complex | Particle size (nm) | Zeta-potential (mV) | PDI |
|---|---|---|---|
| mRNA + P704 | 65.2 ± 6.5 | −23 ± 1.6 | 0.449 |
| mRNA + P704 + Compound 0 (DL) | 54.1 ± 7.4 | 2.17 ± 0.3 | 0.249 |
| mRNA + P704 + Compound 4 | 52.1 ± 6.9 | −1.09 ± 0.3 | 0.230 |
| mRNA + P704 + Compound 9 | 46.2 ± 3.1 | −1.36 ± 0.2 | 0.329 |
| mRNA + P704 + Compound 8 | 856 ± 62 | −2.54 ± 0.3 | 0.391 |
| pDNA + P704 | 206 ± 18 | −19 ± 2.3 | 0.518 |
| pDNA + P704 + Compound 0 (DL) | 69.8 ± 4.0 | 7.21 ± 0.5 | 0.310 |
| pDNA + P704 + Compound 4 | 71.8 ± 1.4 | 1.52 ± 0.2 | 0.245 |
| pDNA + P704 + Compound 9 | 61.4 ± 5.6 | 0.17 ± 1.1 | 0.282 |
| pDNA + P704 + Compound 8 | 1100 ± 87 | −2.93 ± 0.5 | 0.332 |

Ternary complexes containing other compounds showed similar characteristics with that of compound 4 containing ternary complexes.

Optimising compositions of P704 and compound 0 (DL) components within ternary complexes:

In order to investigate the influence of P704 concentration on the transfection of IVT-mRNA containing ternary complexes, compound 0 (DL) was first mixed at N/P ratio of 10 with equal volume of P704 at different concentrations from 25 to 100 (w/w, relative to nucleic acids). After 20 min incubation at RT, equal amounts of MetLuc mRNA (400 ng/well) were added into above-mentioned solutions and mixed thoroughly. The final solutions were added to pre-seeded BEAS-2B cells (FIG. 7a) and 16HBE cells (FIG. 7b) after 20 min incubation at RT and incubated for 4 h at 37° C. in a humidified atmosphere. To evaluate the effect of concentration of compound 0 (DL) on the transfection of IVT-mRNA containing ternary complexes, P704 was first mixed at a concentration of 63 (w/w, relative to nucleic acids) with equal volume of synthetic compound 0 (DL) at different charge ratios (N/P ratios) from 1 to 60 and incubated at RT for 20 min. Then each of the resulting solutions were mixed with MetLuc mRNA (400 ng/well) and incubated for another 20 min. Samples were added to pre-seeded BEAS-2B cells (FIG. 7c) and 16HBE cells (FIG. 7d), and incubated for 4 h at 37° C. in a humidified atmosphere. Luciferase activity was measured as mentioned above. The results are given as mean±SD of three independent experiments.

In order to investigate the effect of P704 concentration on the transfection rate of pDNA containing ternary complexes, compound 0 (DL) was first mixed at N/P ratio of 30 (for BEAS-2B cell transfection) or 20 (for 16HBE cell transfection) with equal volume of P704 at different concentrations from 10 to 100 (w/w, relative to nucleic acids). After 20 min incubation at RT, equal amounts of MetLuc pDNA (400 ng/well) were added into each of the above-mentioned solutions and mixed thoroughly. The final solutions were given to pre-seeded BEAS-2B cells (FIG. 8a) and 16HBE cells (FIG. 8b) after 20 min incubation at RT and incubated for 4 h at 37° C. in a humidified atmosphere. Luciferase activity was measured on day 1, day 2 and day 3 after transfection using the same method as mentioned above. The results are given as mean±SD of three independent experiments. To evaluate the influence of concentration of compound 0 (DL) on the transfection of pDNA containing ternary complexes, P704 at concentrations of 50 (w/w, relative to nucleic acids) for BEAS-2B cell transfection or 63 (w/w, relative to nucleic acids) for 16HBE cell transfection was first mixed with equal volume of compound 0 (DL) at different N/P ratios in a range of 10 to 40 and incubated at RT for 20 min. Each of the resulting solutions was mixed with MetLuc pDNA (400 ng/well) and incubated for another 20 min. Samples were added to pre-seeded BEAS-2B cells (FIG. 8c) and 16HBE cells (FIG. 8d), and incubated for 4 h at 37° C. in a humidified atmosphere. Luciferase activity was measured on day 1, day 2 and day 3 after transfection using the same method as mentioned above. The results are given as mean±SD of three independent experiments.

Optimising other parameters influencing in vitro transfection of ternary complexes using IVT-mRNA:

Examined parameters were the effects of nucleic acids concentration, complex forming medium, method of preparation and incubation time.

Figure 9A:
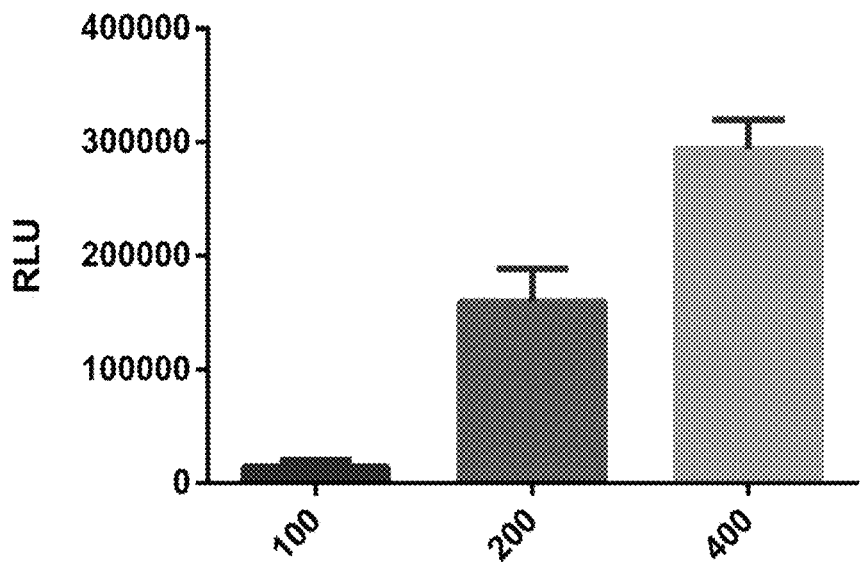

FIG. 9a: MetLuc mRNA at concentrations of 100, 200 or 400 ng/well were respectively used to form ternary complexes with P704 and compound 1 at optimum concentration using same method as described above, and their Luciferase activity 24 h after transfection was measured and compared.

Figure 9B:
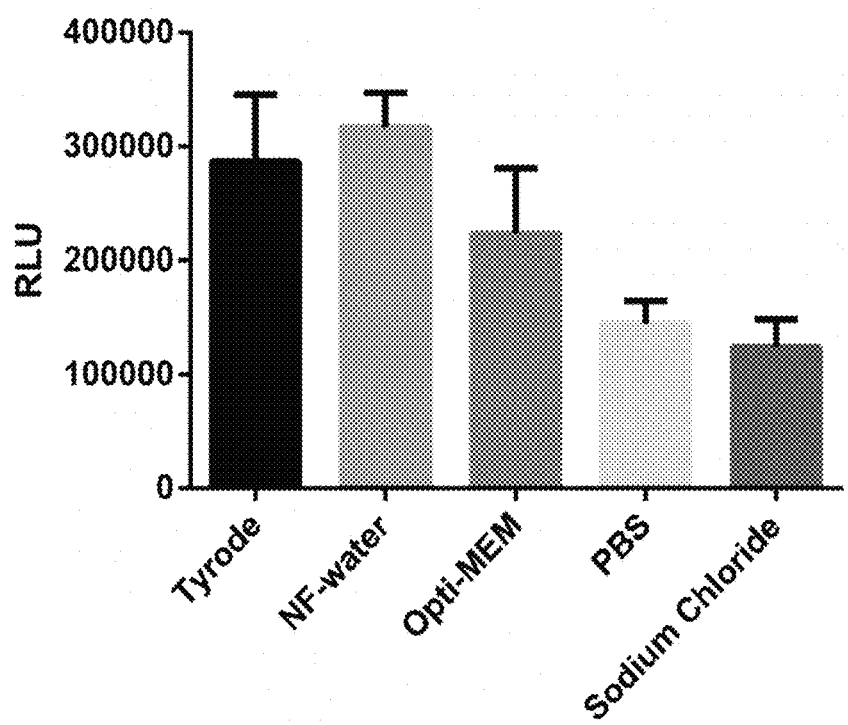

FIG. 9b: The transfection efficiencies (24 h) of MetLuc mRNA containing ternary complexes formed in Tyrode's solution, nuclease-free water (NF-water), opti-MEM, PBS and sodium chloride at optimum concentration of each component.

Figure 9C:
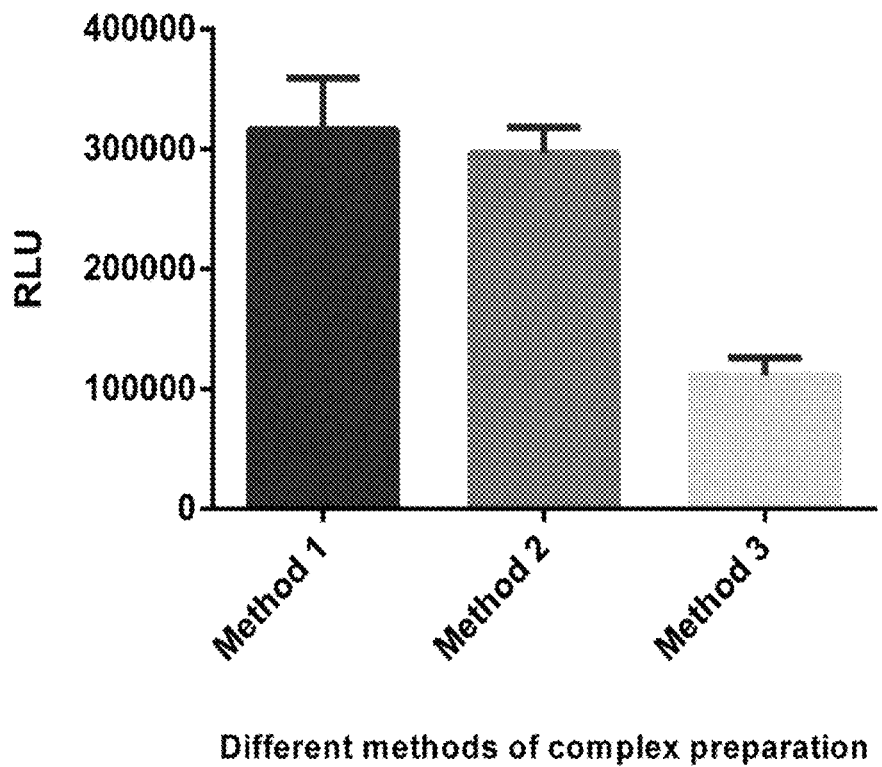

FIG. 9c: IVT-mRNA containing ternary complexes were prepared in three different ways, and their transfection rate at 24 h after transfection were compared. Method 1: P704 and compound 0 at optimum concentration were first mixed and incubate for 20 min, followed by adding of equal volume of IVT-mRNA solution with another 20 min incubation at RT. Method 2: in the first step, P704 and IVT-mRNA solution were mixed and incubate for 20 min incubation at RT, equal volume of compound 0 were added and incubated for another 20 min at RT in the second step. Method 3: Compound 0 was complexed with IVT-mRNA by 20 min incubation at RT, then equal volume of P704 solution was introduced and incubated for another 20 min to form ternary complexes.

Figure 9D:
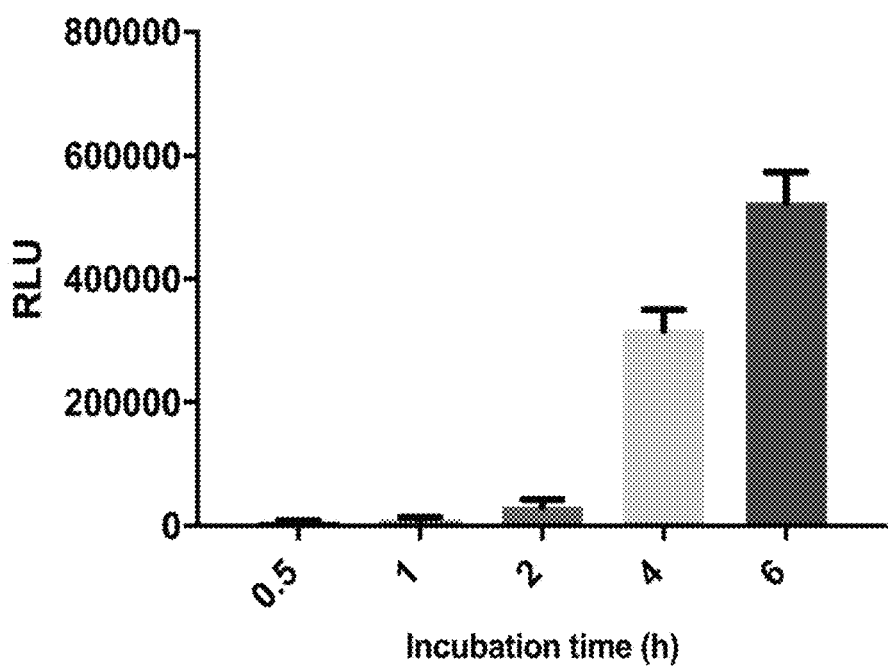

FIG. 9d: The transfection efficiencies of P704/compound 0/MetLuc mRNA ternary complexes with 30 min, 1 h, 2 h, 4 h and 6 h incubation with the 16HBE cells. 24 h after transfection, luciferase activity was measured and compared.

The data in FIGS. 9a to 9d are given as mean±SD (n>5).

Endocytic uptake of fluorescein labled pDNA (Fluo-pDNA), P704/Fluo-pDNA binary complexes, compound 9/Fluo-pDNA binary complexes, Lipofectamine® 2000 based lipoplex and compound 0 (DL), compound 8 or compound 9 containing ternary complexes in 16HBE cells:

16 HBE cells (7.0×10⁵/well) were seeded in 6-well plate 24 h before investigation. P704/Fluo-pDNA binary complexes were prepared by mixing P704 at the concentration of 63 (w/w) with Fluo-pDNA in Tyrode's solution. Compound 9/Fluo-pDNA binary complexes were prepared by mixing compound 9 at the N/P ratio of 5 with Fluo-pDNA in NF-water.

P704 based ternary complexes consisted of P704 at the concentration of 63 (w/w), compound 0 (DL) or compound 9 at optimum N/P ratio and Fluo-pDNA. P304 based ternary complexes consisted of P304 at the concentration of 2000 (w/w), compound 8 at N/P ratio of 20 and Fluo-pDNA.

P90R4 based ternary complexes consisted of P90R4 at the concentration of 1600 (w/w), compound 8 at N/P ratio of 15 and Fluo-pDNA. The amount of Fluo-pDNA in each sample was 4 µg/well. Naked Fluo-pDNA were served as negative control. After 4 h incubation, medium was removed. The cells were harvested and rinsed with cold PBS for three times followed immediately by flow cytometry analysis. The amount of 10 000 live cells was collected for each sample. Results are shown in FIG. 10.

Figure 11A:
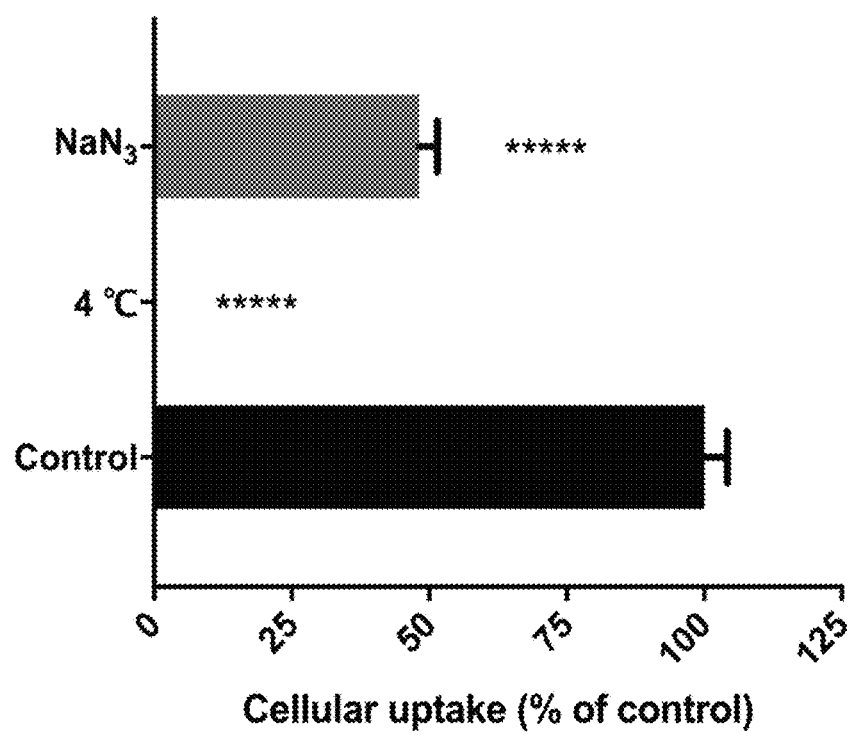

Cell endocytosis mechanism assay—the influence of low temperature and different inhibitors on the endocytosis of Fluo-pDNA containing P704 based ternary complexes in 16HBE cells:

FIG. 11a: Energy-dependent cell uptake of compound 9 containing ternary complexes at 4° C. and in the presence of $NaN_3$.

Figure 11B:
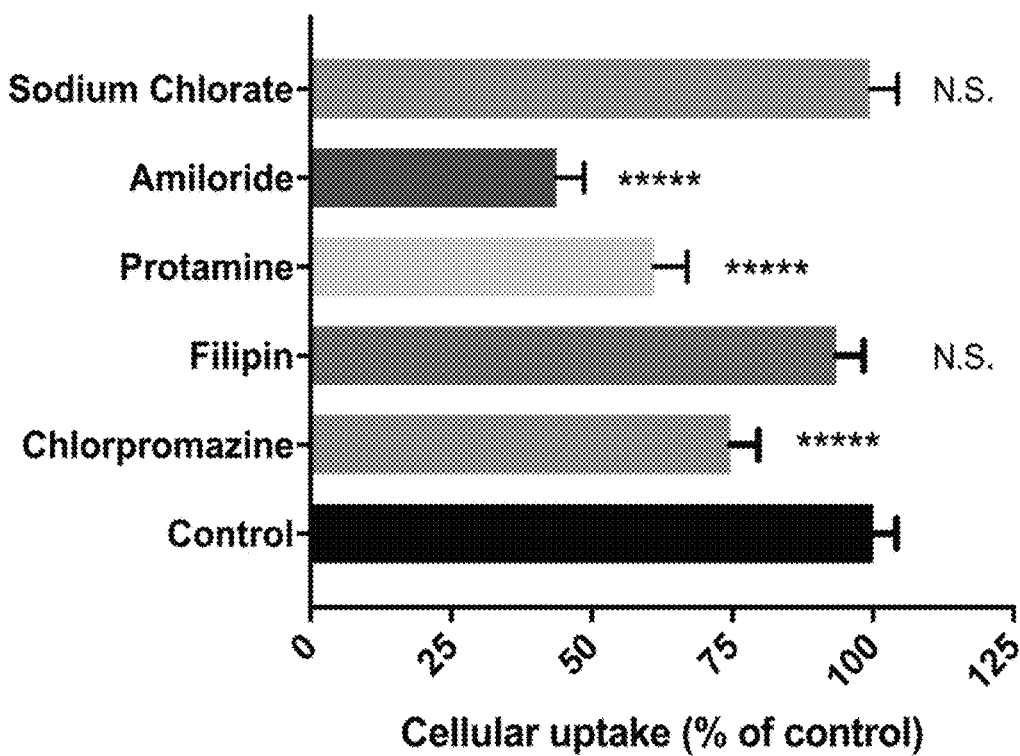

FIG. 11b: Inhibition effect of chlorpromazine, filipin, protamine, amiloride and sodium chlorate on the uptake of compound 9 containing ternary complexes.

Figure 11C:
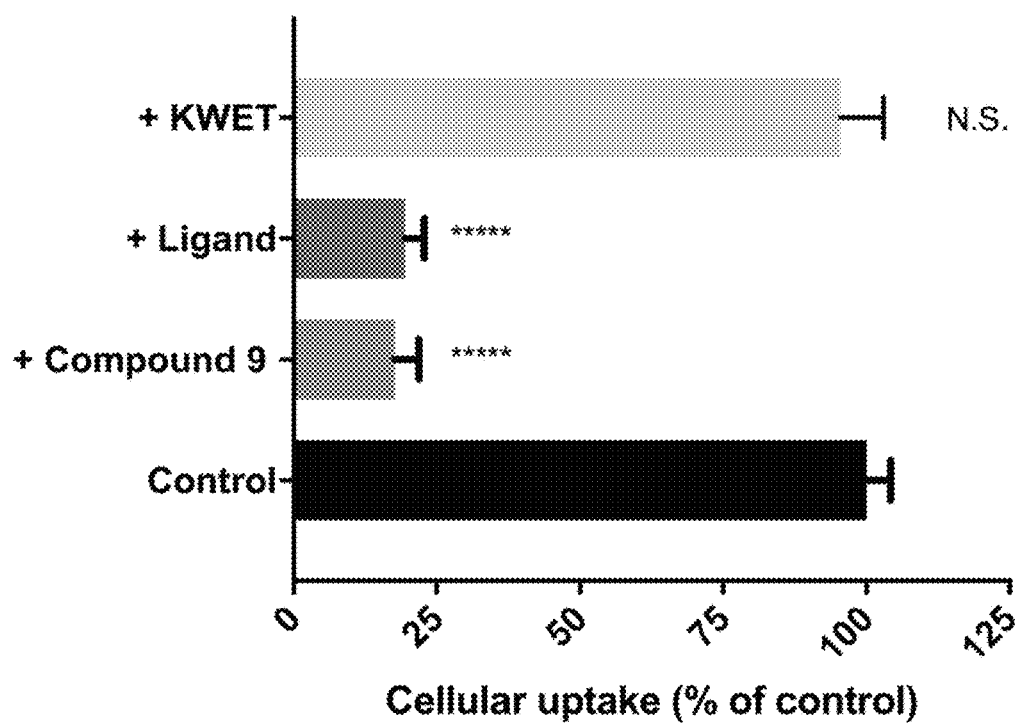

FIG. 11c: Cell-specific endocytosis of compound 9 containing ternary complexes inhibited by free compound 9 and free peptide GACSERSMNFCG (SEQ ID NO:11, designated "ligand") the sequence of which is contained in compound 9, KWET represents the peptide KETWWETWWTEWWTEW (SEQ ID NO:12).

Figure 11D:
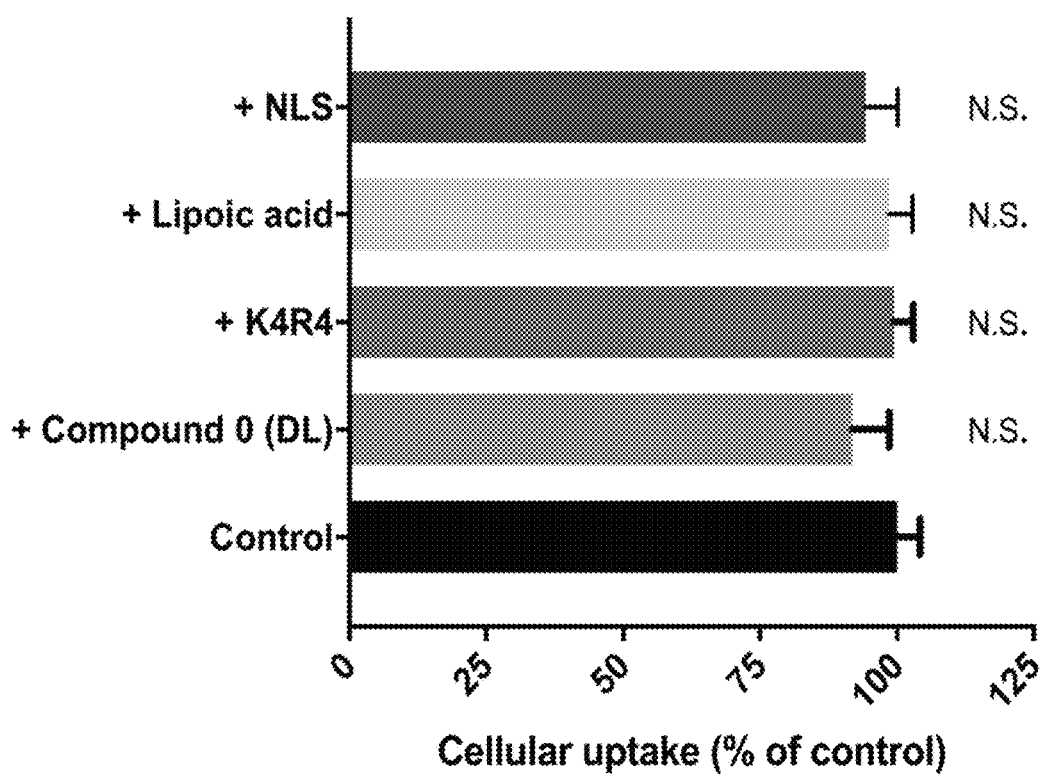
Figure 12A:
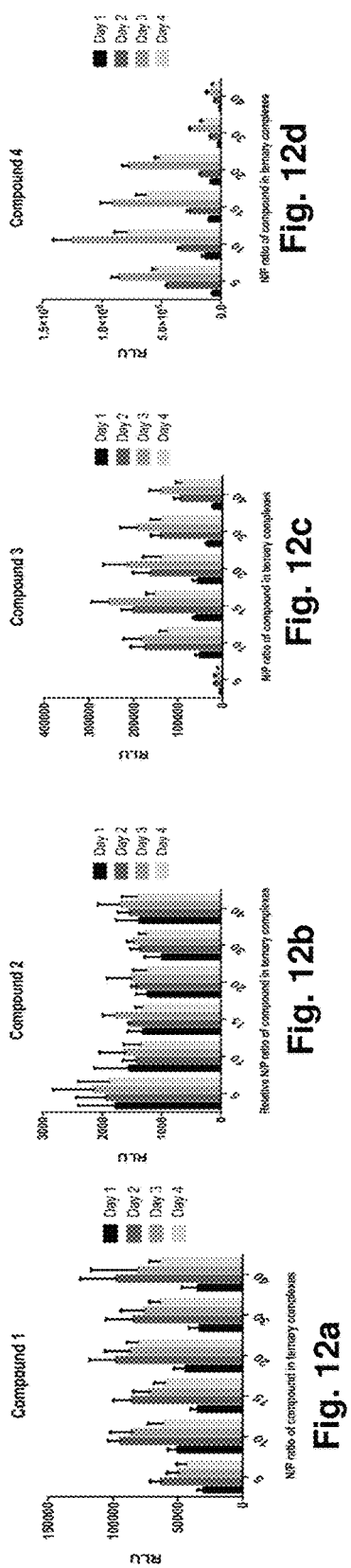
Figure 12B:
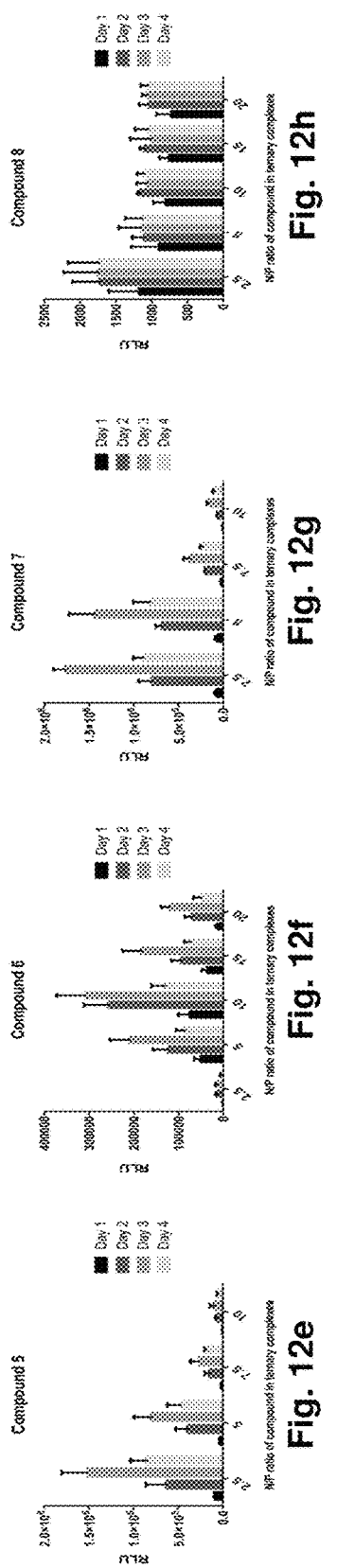
Figure 12C:
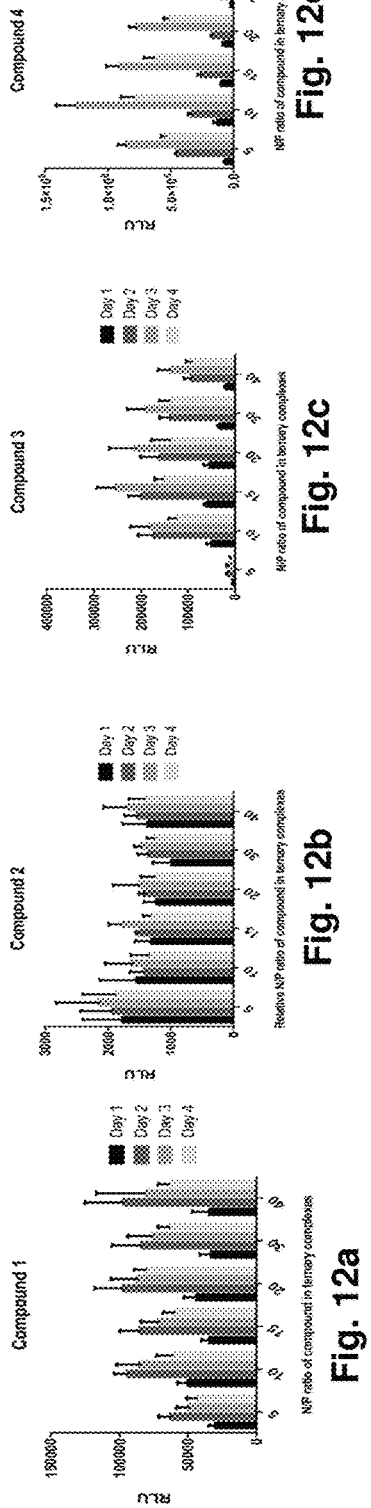
Figure 12D:
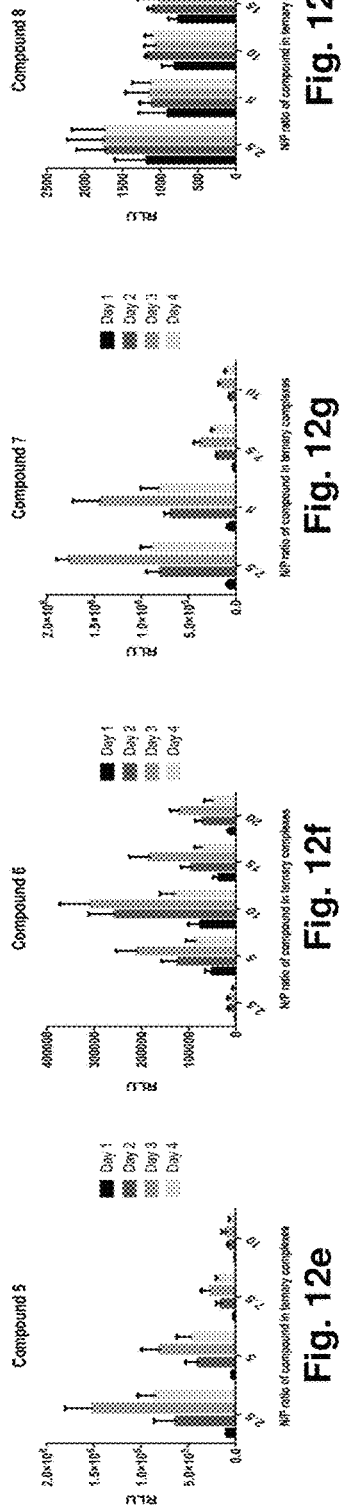
Figure 12E:
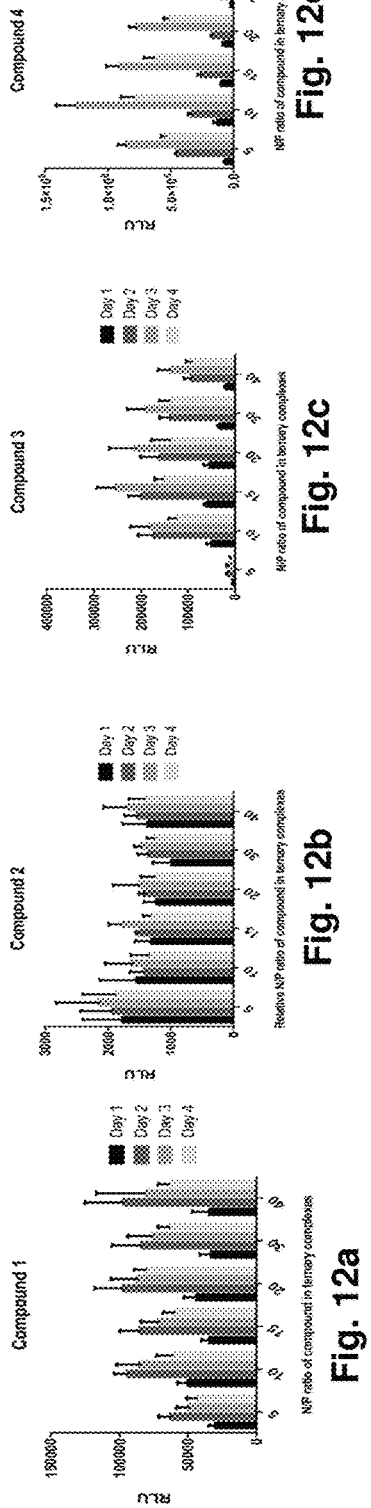
Figure 12F:
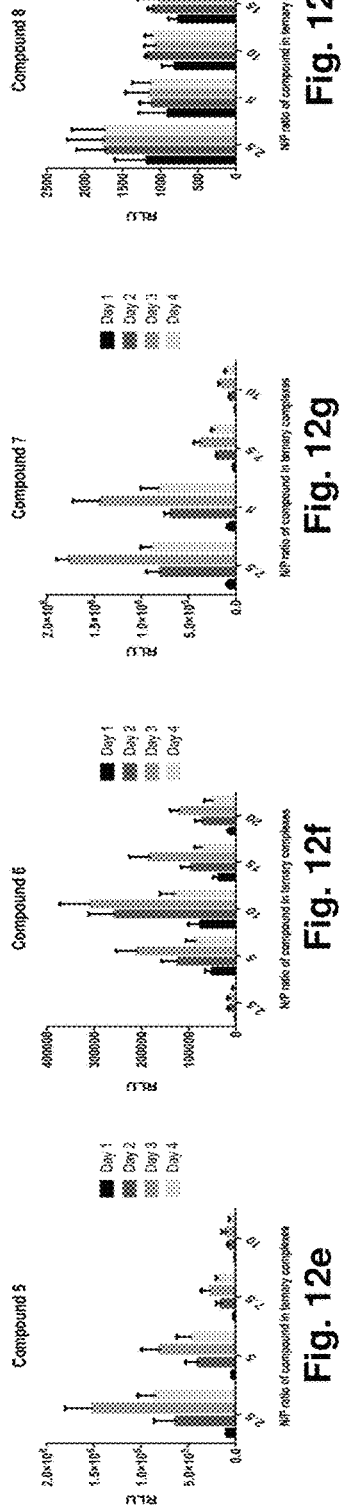
Figure 12G:
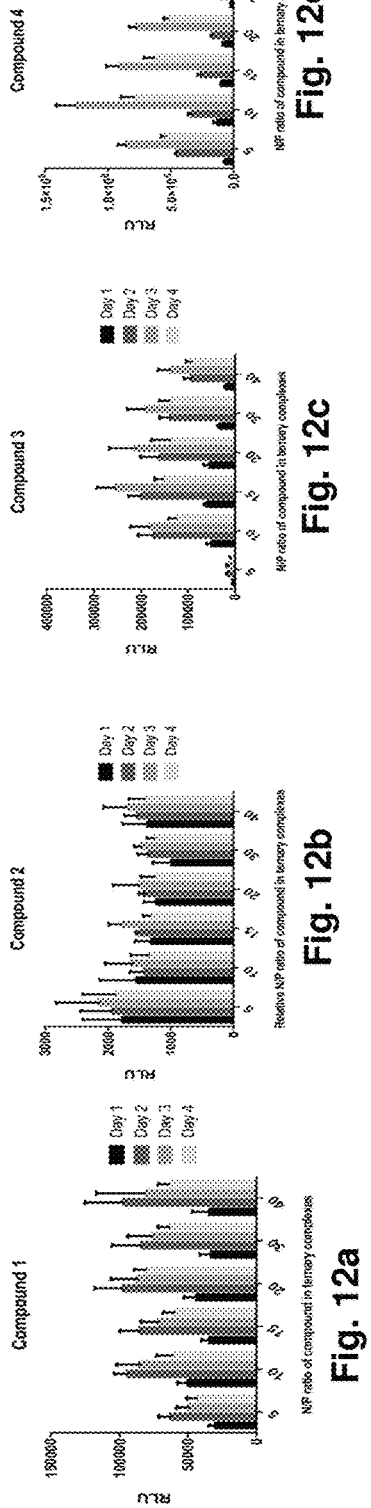
Figure 12H:
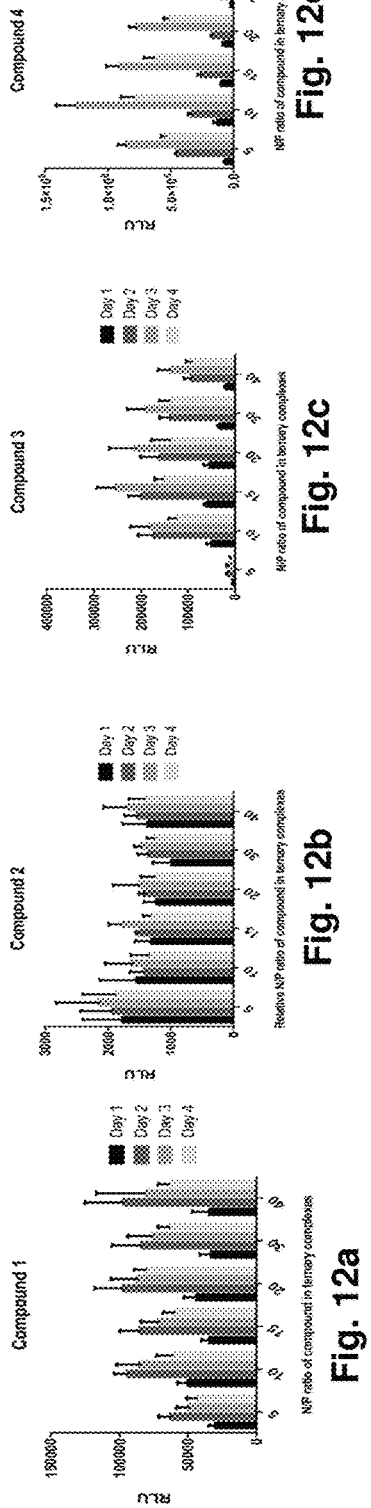
Figure 12I:
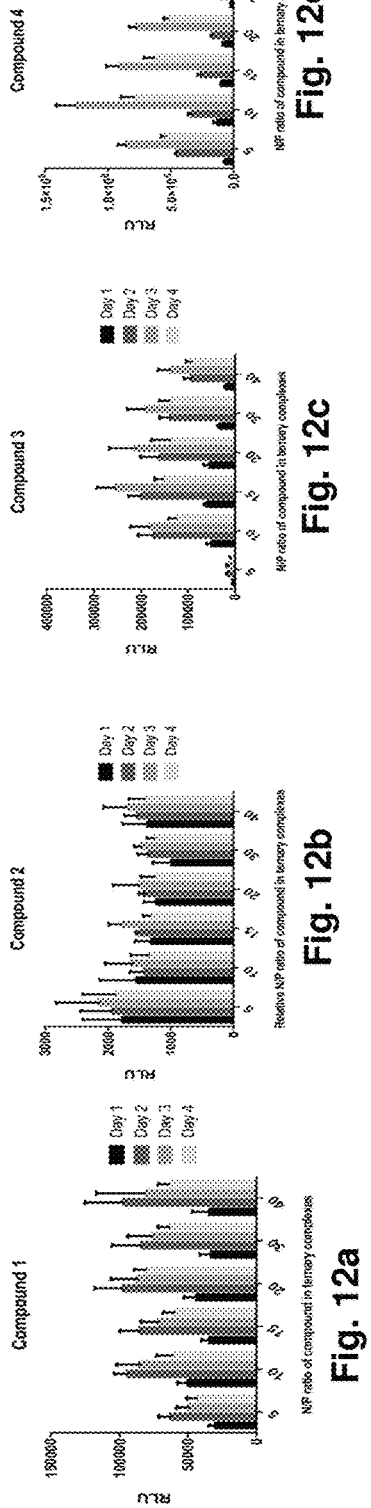
Figure 12J:
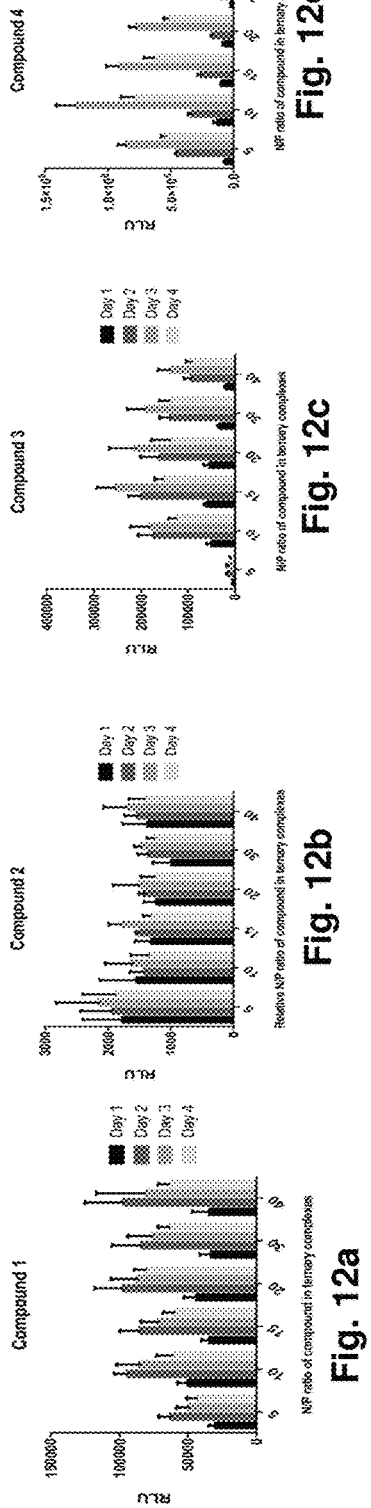
Figure 12K:
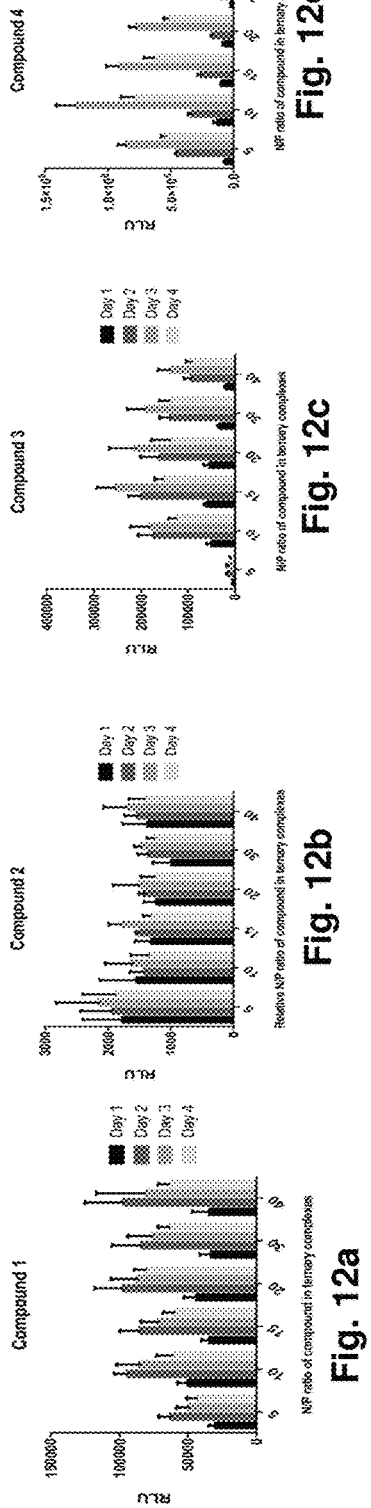

FIG. 11d: Non-cell specific endocytosis of compound 0 (DL) containing ternary complexes, which cannot be inhibited by free compound 0 (DL) and its fragment sequence (i.e. NLS, Lipoic acid and K4R4), K4R4 represents the peptide KKRRRRKK (SEQ ID NO: 13).

The cellular uptake of non-inhibited compound 9 containing ternary complexes were used as control for the experiments shown in FIGS. 11a, 11b and 11c, while the cellular uptake of non-inhibited compound 0 (DL) containing ternary complexes were set as control for the experiment shown in FIG. 11d. Significant differences were defined as *****: $p<0.0001$.

Transfection efficiencies of MetLuc pDNA containing ternary complexes (composed by different compounds) in BEAS-2B cells:

Compounds 1 to 11 at different N/P ratios (as compound 2 did not contain positively charged amino acids at neutral pH, compound 2 was applied in the same molar concentration as compound 0) were complexed with P704 at concentration of 50 (w/w) respectively, followed by adding Metluc pDNA (400 ng/well). The same transfection procedure as described above was applied. Luciferase activity was expressed in RLU. The data are given as the mean±standard deviation (SD) of the mean (n>5) in FIGS. 12a to 12k.

Transfection efficiencies of MetLuc pDNA containing ternary complexes (composed by different compounds) in 16HBE cells:

Compounds 1 to 11 at different N/P ratios (as compound 2 did not contain positively charged amino acids at neutral pH, compound 2 was applied in the same molar concentration as compound 0) were complexed with P704 at concentration of 63 (w/w) respectively, followed by adding Metluc pDNA (400 ng/well). The same transfection procedure as described above was applied. Luciferase activity was expressed in RLU. The data are given as the mean±standard deviation (SD) of the mean (n>5) in FIGS. 13a to 13k.

Comparisons of optimum transfection efficiencies of different pDNA containing ternary complexes comprising different compounds:

The concentration of P704 in ternary complexes for treatment of BEAS-2B cells was 50 (w/w) and the concentration of P704 in ternary complexes for treatment of 16HBE cells was 63 (w/w). The N/P ratios of the compounds in ternary complexes were as follows:

BEAS-2B cells: Compound 0 (DL) at 30, compound 1 at 20, compounds 3 and 11 at 15, compounds 4 and 6 at 10, compounds 2 and 9 at 5, compounds 5, 7, 8 and 10 at 2.5.

16HBE cells: Compound 0 (DL) at 20, compounds 1 and 11 at 15, compounds 2 and 3 at 10, compounds 4, 6, 8, and 9 at 5, compounds 5, 7, and 10 at 2.5.

Results are shown in FIG. 14a for BEAS-2B cells and in FIG. 14b for 16HBE cells.

Transfection efficiencies of MetLuc mRNA containing ternary complexes comprising different synthetic compositions according to the invention in BEAS-2B cells:

Compounds 1 to 11 at different N/P ratios (as compound 2 did not contain positively charged amino acids at neutral pH, compound 2 was applied in the same molar concentration as compound 0) were complexed with P704 at concentration of 63 (w/w) respectively, followed by adding Metluc mRNA (400 ng/well). The same transfection procedure as described above was applied. Luciferase activity was expressed in RLU. The data are given as the mean±standard deviation (SD) of the mean (n>5) in FIGS. 15a to 15k.

Transfection efficiencies of MetLuc mRNA containing ternary complexes comprising different synthetic compositions according to the invention in 16HBE cells:

Compounds 1 to 11 at different N/P ratios (as compound 2 did not contain positively charged amino acids at neutral pH, compound 2 was applied in the same molar concentration as compound 0) were complexed with P704 at concentration of 63 (w/w) respectively, followed by adding MetLuc mRNA (400 ng/well). The same transfection procedure as described above was applied.

Luciferase activity was expressed in RLU. The data are given as the mean±standard deviation (SD) of the mean (n>5) in FIGS. 16a to 16k.

Comparisons of optimum transfection efficiencies of different MetLuc mRNA containing ternary complexes comprising different compounds:

The concentration of P704 in ternary complexes was 63 (w/w). The N/P ratio of the compounds in certain ternary complexes was as follows:

BEAS-2B cells: Compounds 1, 2, 8, and 11 at 20; compounds 0 (DL) and 3 at 10; compound 4 at 7.5; compounds 6, 9, and 10 at 5, compounds 5 and 7 at 2.5.

16HBE cells: Compound 1, 8, and 11 at 20; compound 0 (DL) and 3 at 10; compound 2 at 7.5; compounds 4, 6, 9, and 10 at 5, compounds 5 and 7 at 2.5.

Results are shown in FIG. 17a for BEAS-2B cells and in FIG. 17b for 16HBE cells.

The optimum composition of compound 1, compound 2 and compound 3 containing ternary complexes showing maximum transfection efficiencies were evaluated (results are shown in FIGS. 12a to 13k and 15a to 16k) and compared with that of compound 0 containing ternary complex. In terms of pDNA transfection, compound 1 containing ternary complex could just reach 7% (in BEAS-2B cells) or half (in 16HBE cells) of the maximum signal intensity (on day 3) of compound 0 counterpart as illustrated in FIGS. 14a and 14b.

P704/compound 1/IVT-mRNA complex showed only one third of the transfection efficiency of P704/compound 0/IVT-mRNA complex in both BEAS-2B and 16HBE cells (FIGS. 17a and 17b). Interestingly, both pDNA and IVT-mRNA containing ternary complexes prepared with compound 2 displayed rather low transfection efficiency which was similar to binary counterparts in both cell lines (FIGS. 14a and 14b and 17a and 17b). In evaluation of the NLS function, pDNA within compound 0 containing ternary complex expressed almost 5 times better than counterpart within compound 3 containing ternary complex in BEAS-2B cells (FIG. 14a).

Although the pDNA expression from compound 0 containing ternary complex and compound 3 containing ternary complex were similar on day 2 in 16HBE cells, the former was significantly higher than the latter on other days in this cell line (FIG. 14b). These results indicated that hydrophobic moiety, cationic moiety and targeting moiety are indispensable to the efficient in vitro transfection of compound containing ternary complex.

Compound 4 and compound 5 kept the same hydrophobic moiety and cationic moiety with compound 0 (same numbers of lysine and arginine in the sequence) but contained different targeting moieties. Ligand SERSMNF (ligand S) in compound 4 and ligand YGLPHKF (ligand Y) in compound 5 were identified by phage display and showed high affinity to human airway epithelium cells. The amino acids "GAC . . . CG" provide conformational stability for the ligand component.

Compound 6 and compound 7 shared similar structure with compound 4 and compound 5 but differed in the cationic moiety. Unlike the cationic moiety of compound 4 and compound 5 wherein lysine outnumbered arginine, the cationic moiety of compound 6 and compound 7 contained more arginine than lysine. Compound 8 had same hydrophobic moiety and targeting moiety with compound 4 but contained a cationic moiety dominated by histidine. Compound 9, compound 10, and compound 11 were derived from compound 4 by substitution of different hydrophobic moiety modules. The optimum composition of compound 4 to compound 11 containing ternary complexes showing maximum transfection efficiencies was identified according to FIGS. 12a to 13k and FIGS. 15a to 16k.

The comparison of pDNA or IVT-mRNA transfection efficiencies of these compounds containing ternary complexes in optimum condition was displayed in FIGS. 14a and 14b and FIGS. 17a and 17b. As illustrated in FIG. 14a, pDNA expression from compound 4, compound 5 and compound 7 containing ternary complexes were similar (compound 5 and compound 7 were slightly better at day 3) to that from compound 0 containing ternary complexes in BEAS-2B cells. In contrast, compound 9 containing ternary complexes showed the highest transfection efficiency from day 1 to day 4 among all the tested groups in this cell line. In transfection of 16HBE cells, both compound 6/P704/pDNA and compound 9/P704/pDNA ternary complexes showed overwhelming signals at each time point compared with other compound containing complexes (FIG. 14b). In terms of IVT-mRNA transfection, compound 9 containing ternary complexes were more superior to other counterparts in both BEAS-2B (FIG. 17a) and 16HBE cells (FIG. 17b). These results revealed that compound 9 was the most promising candidate in all aspects (in cooperation with P704). Apart from the same cationic moiety and targeting moiety inherited from compound 4, compound 9 specifically contained an enlarged hydrophobic area made by a triple tryptophan-rich sequence in hydrophobic moiety.

An attractive hypothesis for the superiority of compound 9 would be that the expanded hydrophobic moiety may increases its capacity for docking the PPO groups of P704, thus resulting in a more compact and stable structure than other compounds. This could be partially confirmed via size measurement showing that the particle size of compound 9 containing ternary complex was slightly smaller than other counterparts. In the evaluation of targeting moiety, different candidates had their own advantages in different aspects, but ligand S exceeded others in transfecting 16HBE cells which better mimic the in vivo status. Another advantage of ligand S is that it was completely functional at a rather low concentration compared with NLS, thereby decreasing the positive charge and toxicity of ternary complex.

When comparing the transfection efficiency of compound 4 and compound 6 containing ternary complexes in 16HBE cells, arginine residues were more efficient in mediating mRNA and pDNA transfection compared with lysine residues, and there seemed to be an optimal number of arginine residues (>8) for them to be effective in ternary complex. Based on these results, compound 9 was selected as a leading candidate for the preparation of P704 based ternary complex in following studies.

Comparisons of in vitro transfection efficiencies of P704 based ternary complexes (P704+compound 9+IVT-mRNA or pDNA) with that of other non-viral vectors:

Luciferase activity (24 h after transfection) of MetLuc mRNA containing ternary complexes was compared with Lipofectamine® 2000 and "gold standard" 25-kDa branched polyethylenimine (brPEI) in BEAS-2B and 16HBE cells. Luciferase activity of MetLuc pDNA containing ternary complexes was measured on day 1, day 2, day 3 and day 4 after transfection in BEAS-2B cells and 16HBE cell and compared to those obtained with Lipofectamine® 2000 and brPEI. All complexes were prepared in optimum condition to ensure their best transfection rate on each cell line based on preliminary examination. Complexes comprising Lipofectamine® 2000 were prepared according to the manufacturer's instructions and used as lipoplex (lipid based non-viral vectors) control. Complexes comprising brPEI at N/P ratios of 15 (for IVT-mRNA transfection) or 20 (for pDNA) and 400 ng/well MetLuc mRNA or pDNA were formed in NF-water and served as polyplex (polymer based non-viral vectors) control. Results are given as the mean±SD of three independent experiments in FIGS. 18a to 18d. Significant differences were defined as N. S.: Not significant; *: $p<0.05$; : $p<0.01$; *: $p<0.005$; **: $p<0.001$; ***: $p<0.0001$.

Transfection rates of EGFP mRNA or EGFP pDNA containing ternary complexes (P704+compound 9+nucleic acids) in BEAS-2B and 16HBE cells:

BEAS-2B cells were pre-seeded in 6-well plate 24 h before transfection. The concentration of P704 in ternary complexes was 63 (w/w, relative to nucleic acids). The N/P ratio of compound 9 in certain ternary complexes was 5. Lipofectamine® 2000 at concentration of 6.7 µl/well was used as positive control. The amount of EGFP mRNA or EGFP pDNA in each sample was 4 µg/well. Cells were harvest and measured 24 h (for IVT-mRNA transfection) or 48 h (for pDNA transfection) after transfection by flow cytometry. Transfection rate and mean of fluoresce intensity were recorded (n>3). Results are shown in FIG. 19a for BEAS-2B cells and in FIG. 19b for 16HBE cells. Bars represent numbers of EGFP-positive cells (grey-IVT-mRNA, white-pDNA); individual dots refer to mean fluorescence intensities per cell.

Comparisons of toxicities of pDNA containing formulations prepared with P704, compound 9, Lipofectamine® 2000 and brPEI:

Compound 9 (0.5 to 40 µg/well), P704 (0.5 to 40 µg/well), Lipofectamine® 2000 (0.1 to 5 µg/well) and brPEI (0.1 to 20 µg/well) at the different concentrations given in the parentheses were incubated with BEAS-2B and 16HBE cells for 4 h at 37° C. in a humidified atmosphere, then fresh cell culture media as recommended were added to substitute above samples. An MTT assay was performed 24 h post transfection. Results are given in FIGS. 20a and 20b.

The cytotoxicity of optimized ternary complexes consisting of P704 at 63 (w/w), compound 9 at N/P ratio of 5 and pDNA against BEAS-2B cells and 16HBE cells was investigated and compared with that of lipoplex control (Lipofectamine® 2000 at 0.8 µg/well) and polyplex control (brPEI at N/P ratio of 20). The pDNA concentration in all complexes was fixed at 400 ng/well. After 4 h incubation at 37° C. in a humidified atmosphere, fresh cell culture media as recommended were added to substitute pDNA containing samples. An MTT assay was performed 24 h post transfection. Non-treat cells were served as positive control. The data are given as the mean±SD (n>5) in FIGS. 20c and 20d. Significant differences are defined as *: $p<0.05$; : $p<0.01$; *: $p<0.005$; **: $p<0.001$; ***: $p<0.0001$.

Expression kinetics of IVT-mRNA or pDNA containing ternary complexes:

Compound 9 containing ternary complexes in optimum composition were incubated with 16HBE cells for 4 h. Luciferase activity in 50 µl of supernatants was assayed every 24 h till the relative light units measured with a luminometer dropped below 500. The media were replaced daily after collecting samples for analysis. Enzyme activity is expressed in relative light units, n=5. Results obtained with IVT-mRNA are shown in FIG. 21a and results obtained with pDNA are shown in FIG. 21b.

Western Blot Analysis:

Total membrane proteins (25 µg) from CFBE-WT, CFBE-delF and transfected CFBE-delF cells were isolated by using RIPA lysis buffer and separated on a 7.5% SDS-PAGE. For identifying CFTR a monoclonal anti-CFTR antibody detecting a CFTR band in the range of 170 kDa was used. Furthermore, a 3-actin antibody detecting the protein in the range of 43 kDa was used for normalization. The western blot is shown in FIG. 22a. Lanes were loaded from the left to the right as follows: Lane 1: Precision Plus® Protein standards; lane 2: CFBE-WT; lane 3: non-transfected CFBE-delF; lane 4: transfected CFBE-delF.

FIG. 22b shows a quantitative evaluation of the relative CFTR protein amount in transfected and nontransfected epithelial cells. Non-transfected CFBE-delF cells exhibited approximately 50% less CFTR protein compared to the transfected CFBE-delF cells. Relative protein expression of the CFBE WT control protein was normalized to 100% (n=3).

Comparisons of transfection efficiencies of MetLuc mRNA containing ternary complexes comprising other poloxamines or a poloxamer at different concentration in 16HBE cells:

P304, P904 and P90R4 in the concentration range of 10-2500 (w/w) were complexed with compound 6 at N/P ratio of 5, followed by adding Metluc mRNA (400 ng/well). In terms of poloxamer containing ternary complexes, L64 in the concentration range of 10-200 (w/w) were complexed with compound 0 (DL) at N/P ratio of 10, followed by adding Metluc mRNA (400 ng/well). The same transfection procedure as described above was applied. Luciferase activity was expressed in RLU. Results are given as the mean±standard deviation (SD) of the mean (n>5) in FIGS. 23a to 23d.

Comparisons of transfection efficiencies of MetLuc mRNA containing P304 or P90R4 based ternary complexes comprising different compounds in 16HBE cells:

Compounds 6 to 10 at different N/P ratios were complexed with P304 at a concentration of 2000 (w/w) respectively, followed by addition of Metluc mRNA (400 ng/well). Compounds 6 to 10 at different N/P ratios were complexed with P90R4 at a concentration of 1600 (w/w) respectively, followed by addition of Metluc mRNA (400 ng/well). The same transfection procedure as described above was applied for P304 or P90R4 based ternary complexes. Luciferase activity was expressed in RLU. The data are given as the mean±standard deviation (SD) of the mean (n>5) in FIG. 24a for P304 based ternary complexes and in FIG. 24b for P90R4 based ternary complexes.

Comparisons of optimum transfection efficiencies of different MetLuc mRNA containing ternary complexes comprising different compounds in 16HBE cells:

The concentration of P304 in ternary complexes was 2000 (w/w). The N/P ratio of compounds in certain ternary complexes was as follows: Compound 8 at 15; compound 9 at 10; compounds 6 and 10 at 5; compound 7 at 2.5. Results are shown in FIG. 25a.

Ternary complexes of compound 8 with P304 and MetLuc mRNA showed rather high luciferase expression in 16HBE cells at high N/P ratio of compound 8, which is even higher than ternary complexes comprising compound 9 that represents the leading compound in terms of P704 based ternary complexes (FIG. 25a).

The concentration of P90R4 in ternary complexes was 1600 (w/w). The N/P ratio of compound in certain ternary complexes was as follows: Compound 8 at 10; compounds 6, 9, and 10 at 5; compound 7 at 2.5. Results are shown in FIG. 25b.

P704 based ternary complexes for BEAS-2B cell transfection comprised P704 at concentration of 50 (w/w, relative to nucleic acids) and synthetic compound 0 (DL) at N/P ratio of 30. P704 based ternary complexes for 16HBE cell transfection comprised P704 at concentration of 63 (w/w, relative to nucleic acids) and synthetic compound 0 (DL) at N/P ratio of 20. Both ternary complexes comprised 400 ng/well MetLuc pDNA and were prepared in Tyrode solution. Lipofectamine® 2000 at concentrations of 0.4 µl/well (for BEAS-2B cell transfection) and 0.5 µl/well (for 16HBE cell transfection) were mixed with 400 ng/well MetLuc pDNA in opti-MEM, respectively. A fraction of complexes was kept apart and used as a "non-nebulized" control. The rest of the solutions was aerosolized for 5 minutes by employing PARI Boy® Nebulizer. The nebulized solutions were collected in a separate tube. Non-nebulized control, Collected solution (nebulized) and solution remaining in the nebulizer (reservoir) were incubated with BEAS-2B cells (FIG. 26a) and 16HBE cells (FIG. 26b) for 4 h at 37° C. in a humidified atmosphere. Luciferase activity in 50 µl of supernatants was assayed 24 h, 48 h, and 72 h after transfection. The luciferase activity is expressed in RLU. The cell culture media was replaced each day after sampling. In the figures "T" means "P704 based ternary complexes" and "L" means Lipofectamine® 2000 based lipoplexes. The results are given as mean±SD of three independent experiments in FIGS. 26a and 26b. Significant differences are defined as N. S.: Not significant;*: $p<0.05$; : $p<0.01$; *: $p<0.005$; **: $p<0.001$; ***: $p<0.0001$.

In Vivo Experiments:

Mice were anesthetized with ketamine (70 mg/kg) and xylazine (15 mg/kg) injected intraperitoneally. After anesthesia, fLUC-CFTR pDNA pDNA formulated with DOTAP (DOTAP lipoplex), 0.25% P704 (Binary complex) or 0.25% P704/compound 9 at N/P ratio of 5 (Ternary complex) was instilled intratracheally as a bolus (50 µl/mouse) through a 22-gauge catheter. All complexes administered contained 15 µg pDNA/mouse. Mice which receive NF-water (50 µl/mouse) were studied as negative controls. Luciferase activity was determined 48 h post administration. Mice were anesthetized followed by application of the substrate D-luciferin (1.5 mg/50 ml PBS per mouse). Bioluminescence was measured 10 min later using a Xenogen IVIS In Vivo Imaging System 100 (Caliper Life Sciences, California, USA).

Visualizations of bioluminescence in the mice are shown in FIG. 27. A graphical presentation of intensity of measured bioluminescence is shown in FIG. 28a. Significant differences are defined as *: $p<0.05$; : $p<0.01$; *: $p<0.005$; **: $p<0.001$; ***: $p<0.0001$.

For white blood cells count, blood samples were taken from mice 24 h after intratracheal administration of pDNA containing binary complex or ternary complex or DOTAP-based lipoplex as described above. The concentration of white blood cells was measure by KX-21 Sysmex Automated Hematology Analyzer (Sysmex GmbH, Canada). Mice receiving NF-water were used as controls. Results are shown in FIG. 28b. Significant differences are defined as *: $p<0.005$; ***: $p<0.0001$. N.S. means "not significant".

---

The invention claimed is:

1. A synthetic compound for enabling transfection of eukaryotic cells, in combination with an amphiphilic block copolymer which synthetic compound comprises a peptide residue having at least one targeting sequence and a nucleic acid binding sequence which nucleic acid binding sequence comprises at least four consecutive amino acid residues which are positively charged at pH 7.4, wherein the peptide residue comprises SEQ ID Nos: SEQ ID NO: 1, SEQ ID NO: 2, SEQ ID NO: 4, SEQ ID NO: 5, SEQ ILS NO: 6, SEQ ID NO: 7, SEQ ID NO: 8, SEQ ID NO: 9 or SEQ ID NO: 10, wherein the synthetic compound further comprises a hydrophobic moiety covalently linked to the peptide residue, wherein the hydrophobic moiety comprises lipoic acid residue, lipoamide residue, a tetradecyl residue, a cholesteryl residue, or a further peptide residue having a sequence with more than 40% amino acid residues with hydrophobic side chains, the further peptide comprising at least four amino acid residues with hydrophobic side chains, wherein the amino acid residues with hydrophobic side chains are amino acid residues of phenylalanine, tyrosine and tryptophan and the targeting sequence comprises a nuclear localization signal (NLS) sequence, a skeletal muscle cell ligand, a myocardium ligand, and/or an epithelium ligand sequence.

2. The synthetic compound according to claim 1, wherein the epithelium ligand sequence is a human airway epithelium ligand sequence.

3. The synthetic compound according to claim 1, wherein the positively charged amino acid residues comprise histidine residue(s), arginine residue(s) and/or lysine residue(s).

4. The synthetic compound according to claim 1, wherein the hydrophobic moiety is covalently linked to the amino terminus or to the carboxy terminus or to any side chain of any amino acid residue of the peptide residue.

5. The synthetic compound according to claim 4, wherein the side chain is the side chain of lysine.

6. The synthetic compound according to claim 1, wherein the maximal length of the peptide residue, optionally together with the further peptide residue, is 45 amino acid residues.

7. A pharmaceutical composition comprising the synthetic compound according to claim 1 together with a pharmaceutically acceptable carrier.

8. The synthetic compound according to claim 1 for use in the treatment of a genetically caused disease of a human being or an animal by gene therapy, wherein the synthetic compound is used together with the amphiphilic block copolymer and a nucleic acid to be transferred into the cells of the human or an animal.

9. The synthetic compound for use in the treatment of a genetically caused disease of a human being or an animal by gene therapy or by an immunotherapy or for use in preventing an infection by vaccination according to claim 8, wherein the amphiphilic block copolymer is a poloxamer or a poloxamine.

10. The synthetic compound of claim 9, wherein the poloxamer is poloxamer 184 and/or the poloxamine is an ethylene oxide-propylene oxide copolymer with tetraether with (1,2-ethanedinitrilo)tetrakis(propanol).

11. The synthetic compound for use in the treatment of a genetically caused disease of a human being or an animal by gene therapy according to claim 8, wherein the compound is present in a nebulized form.

12. The synthetic compound for use in the treatment of a genetically caused disease of a human being or an animal by gene therapy or by an immunotherapy or for use in preventing an infection by vaccination according to claim 9, wherein the compound is present in a nebulized form.

13. Method for an in vitro transfection of eukaryotic cells in cell culture comprising the following steps:
   a1) Mixing a plurality of molecules of the synthetic compound according to claim 1 with a plurality of molecules of an amphiphilic block copolymers to allow the formation of binary complexes,
   b1) mixing the formed complexes with a plurality of molecules of a nucleic acid to be transferred into the cells to allow the formation of ternary complexes,
or
   a2) mixing a plurality of molecules of a nucleic acid to be transferred into the cells with a plurality of molecules of an amphiphilic block copolymers to allow the formation of binary complexes,
   b2) mixing the formed complexes with a plurality of molecules of the synthetic compound according to claim 1 to allow the formation of ternary complexes
and
   c) contacting the ternary complexes with the cells to be transfected.

14. Method according to claim 13, wherein the amphiphilic block copolymer is a poloxamer or a poloxamine.

15. The synthetic compound of claim 9, wherein the amphiphilic block copolymer is poloxamer 184.

16. The synthetic compound according to claim 1, wherein the further peptide residue has a sequence with more than 50% amino acid residues with hydrophobic side chains.

* * * * *

SEQUENCE LISTING

```
<160> NUMBER OF SEQ ID NOS: 13

<210> SEQ ID NO 1
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (17)..(17)
<223> OTHER INFORMATION: AMIDATION

<400> SEQUENCE: 1

Val Lys Arg Lys Lys Lys Pro Lys Lys Arg Arg Arg Arg Lys Lys Trp
1               5                   10                  15

Lys

<210> SEQ ID NO 2
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (15)..(15)
<223> OTHER INFORMATION: AMIDATION

<400> SEQUENCE: 2

Val Lys Arg Lys Lys Lys Pro Lys Lys Arg Arg Arg Arg Lys Lys
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (17)..(17)
<223> OTHER INFORMATION: AMIDATION

<400> SEQUENCE: 3

Val Lys Arg Lys Thr Lys Pro Lys Lys Arg Arg Arg Arg Lys Lys Trp
1               5                   10                  15

Lys

<210> SEQ ID NO 4
<211> LENGTH: 26
<212> TYPE: PRT
<213> ORGANISM: Artificial Sequence
<220> FEATURE:
<223> OTHER INFORMATION: Synthetic Peptide
```

<400> SEQUENCE: 4

Trp Lys Lys Lys Lys Arg Arg Arg Arg Lys Lys Lys Lys Gly Ala
1               5                   10                  15

Cys Ser Glu Arg Ser Met Asn Phe Cys Gly
            20                  25

<210> SEQ ID NO 5
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 5

Trp Lys Lys Lys Lys Arg Arg Arg Arg Lys Lys Lys Lys Gly Ala
1               5                   10                  15

Cys Tyr Gly Leu Pro His Lys Phe Cys Gly
            20                  25

<210> SEQ ID NO 6
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 6

Trp Lys Lys Arg Arg Arg Arg Arg Arg Arg Lys Lys Gly Ala Cys
1               5                   10                  15

Tyr Gly Leu Pro His Lys Phe Cys Gly
            20                  25

<210> SEQ ID NO 7
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 7

Trp Leu His His His Lys Lys Leu Leu His His His Lys Lys Leu Gly
1               5                   10                  15

Ala Cys Ser Glu Arg Ser Met Asn Phe Cys Gly
            20                  25

<210> SEQ ID NO 8
<211> LENGTH: 41
<212> TYPE: PRT
<213> ORGANISM: Artificial Sequence
<220> FEATURE:
<223> OTHER INFORMATION: Synthetic Peptide

<400> SEQUENCE: 8

Lys Glu Thr Trp Trp Glu Thr Trp Trp Thr Glu Trp Trp Thr Glu Trp
1               5                   10                  15

Lys Lys Lys Lys Arg Arg Arg Arg Arg Lys Lys Lys Lys Gly Ala Cys
            20                  25                  30

Ser Glu Arg Ser Met Asn Phe Cys Gly
            35                  40

<210> SEQ ID NO 9
<211> LENGTH: 25
<212> TYPE: PRT

```
<213> ORGANISM: Artificial Sequence
<220> FEATURE:
<223> OTHER INFORMATION: Synthetic Peptide

<400> SEQUENCE: 9

Lys Lys Lys Lys Arg Arg Arg Arg Arg Lys Lys Lys Lys Gly Ala Cys
1               5                   10                  15

Ser Glu Arg Ser Met Asn Phe Cys Gly
            20                  25

<210> SEQ ID NO 10
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 10

Trp Lys Lys Arg Arg Arg Arg Arg Arg Arg Arg Lys Lys Gly Ala
1               5                   10                  15

Cys Ser Glu Arg Ser Met Asn Phe Cys Gly
            20                  25

<210> SEQ ID NO 11
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 11

Gly Ala Cys Ser Glu Arg Ser Met Asn Phe Cys Gly
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 12

Lys Glu Thr Trp Trp Glu Thr Trp Trp Thr Glu Trp Trp Thr Glu Trp
1               5                   10                  15

<210> SEQ ID NO 13
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 13

Lys Lys Arg Arg Arg Arg Lys Lys
1               5
```